US008071321B2

(12) United States Patent
Durda et al.

(10) Patent No.: US 8,071,321 B2
(45) Date of Patent: Dec. 6, 2011

(54) METHODS FOR UP-REGULATING ANTIGEN EXPRESSION IN TUMORS

(75) Inventors: Paul Durda, Needham, MA (US); James T. Kurnick, Winchester, MA (US); Ian S. Dunn, Sydney (AU)

(73) Assignee: CytoCure LLC, Beverly, MA (US)

(*) Notice: Subject to any disclaimer, the term of this patent is extended or adjusted under 35 U.S.C. 154(b) by 1072 days.

(21) Appl. No.: 10/651,616

(22) Filed: Aug. 29, 2003

(65) Prior Publication Data
US 2004/0253235 A1 Dec. 16, 2004

Related U.S. Application Data

(60) Provisional application No. 60/407,492, filed on Aug. 29, 2002.

(51) Int. Cl.
*A61K 39/395* (2006.01)
(52) U.S. Cl. .................................. 435/7.23; 424/143.1
(58) Field of Classification Search ................. 435/7.23; 424/143.1
See application file for complete search history.

(56) References Cited

U.S. PATENT DOCUMENTS

| | | | |
|---|---|---|---|
| 4,737,462 A | 4/1988 | Mark et al. | |
| 4,738,845 A | 4/1988 | Bell et al. | |
| 4,753,795 A | 6/1988 | Bell et al. | |
| 4,793,995 A | 12/1988 | Bell et al. | |
| 6,514,729 B1 | 2/2003 | Bentzien | |
| 6,710,086 B1 | 3/2004 | Lai et al. | |
| 2001/0042551 A1 | 11/2001 | Kutzko et al. | |
| 2004/0022869 A1* | 2/2004 | Chen et al. | 424/623 |
| 2006/0228326 A1* | 10/2006 | Fidler et al. | 424/85.1 |

FOREIGN PATENT DOCUMENTS

| | | |
|---|---|---|
| EP | 0 536 520 A1 | 4/1993 |
| EP | 0 835 661 A2 | 4/1998 |
| WO | WO 2004/037182 | 5/2004 |

OTHER PUBLICATIONS

Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Mocellin et al. (Biochem. Biophys. Acta 1653:61-71 (2003)).*
American Cancer Society, Cancer reference information: "How is melanoma skin cancer staged?", pp. 1-7 (May 14, 2009).*
American Cancer Society, Cancer reference information: "How are brain and spinal tumors in adults staged?", p. 1 (Aug. 28, 2009).*
Bordignon et al (Haematologica 84:1110-1149 (1999)).*
Leitner et al., "Type I Interferons are essential for the efficacy of replicase-based DNA vaccines", Vaccine 24:24 , 5110-5118 (2006).
Zhang et al., "A novel DNA vaccine based on ubiquitin-proteasome pathway targeting 'self'-antigens expressed in melanoma/melanocyte", Gene Ther. 12:13, 1049-1057 (2005).
Shibata et al., "Induction of efficient antitumor immunity using dendritic cells activated by recombinant Sendai virus and its modulation by exogenous IFN-beta gene", J. Immunol. 177:6, 3564-3576 (2006).
Dezfouli et al., "Enhancing CTL responses to melanoma cell vaccines in vivo: synergistic increases obtained using IFNgamma primed and IFNbeta treated B7-1+ B16-F10 melanoma cells", Immunol. Cell Biol. 81 :6, 459-471 (2003).
Sterman et al., "A phase I clinical trial of single-dose intrapleural IFN-beta gene transfer for malignant pleural mesothelioma and metastatic pleural effusions: high rate of antitumor immune responses", Clin. Cancer Res. 13 :15, 4456-4466 (2007).
Kruklitis et al., "Immuno-gene therapy with interferon-beta before surgical debulking delays recurrence and improves survival in a murine model of malignant mesothelioma", J. Thorac. Cardiovasc. Surg. 127 :1, 123-130 (2004).
Saito et al., "Vaccination with tumor cell lysate-pulsed dendritic cells augments the effect of IFN-beta gene therapy for malignant glioma in an experimental mouse intracranial glioma", Int. J. Cancer 111: 5, 777-782 (2004).
Borden, "Augmentatio n of effects of interferon-stimulated genes by reversal of epigenetic silencing: potential application to melanoma", Cytokine. Growth Factor Rev. 18:5-6, 491-501 (2007).
Learman et al., "Novel growth and death related interferon-stimulated gene s (ISGs) in melanoma: greater potency of IFN-beta compared with IFN-alpha2", J. Interferon Cytokine. Res. 23: 12, 745-756 (2003).
Sarkar et al., "Defining the mechanism by which IFN-beta dowregulates c-myc expression in human melan oma cells: pivotal role of human polynucleotide phosphorylase (hPNPaseold-35)", Cell Death Differ. 13 :9, 1541-1553 (2006).
Staudt et al., "Model cell culture system for defining the molecular and biochemical events mediating terminal differentiation of human melanoma cells", J. Cell. Physiol. online (Oct. 9, 2008).
Gogas et al., "Prognostic significance of autoimmunity during treatment of melanoma with interferon", N. Engl . J. Med. 354:7, 709-718 (2006).
Moschos et al., "Present role and future potential of type I interferons in adjuvant therapy of high-risk operable melanoma", Cytokine. Growth Factor Rev. 18:5-6, 451-458 (2007).
Brown et al., "Interferon alpha and CPG oligodeoxynucleotides elicit additive immunostimulatory and antitutmor effects", Surgery 140 :2, 297-306 (2006).
Kubo et al., "Interferon-beta therapy for malignant melanoma: the dose is crucial for inhibition of proliferation and induction of apoptosis of melanoma cells", Arch. Dermatol. Res. 300:6, 297-301 (2008).
Rapprich et al., "Intralesional therapy of metastatic spreading melanoma with beta-interferon", J. Dtsch. Dermatol. Ges. 4 :9, 743-746 (2006).
Kawada et al., "Local injection of interferon beta in malignan t melanoma of the esophagus as adjuvant of systemic pre- and postoperative DAV chemotherapy: case report with 7 years of long-term survival", Gastrointest. Endosc. 66 :2, 408-410 (2007).

(Continued)

*Primary Examiner* — Lynn Bristol
(74) *Attorney, Agent, or Firm* — Clark & Elbing LLP

(57) ABSTRACT

The invention provides methods of modulating tumor antigen associated (TAA) expression, and methods of modulating TAA expression in order to treat a tumor. More particularly, the invention provides methods of increasing an immune response against a tumor cell. Methods include administering to a subject with a tumor an amount of IFN-β receptor agonist and tumor associated antigen (TAA) sufficient to increase an immune response against the tumor cell.

80 Claims, 8 Drawing Sheets

OTHER PUBLICATIONS

Voelter-Mahlknecht et al., "Phase 2 trial of the continuous IV administration of interferon-beta in patients with disseminated malignant melanoma", Skinmed. 5:6, 271-276 (2006).
Gibbs et al., "Malignant melanoma in a multiple sclerosis patient with persistent neutralizing antibodies to interferon-beta", Eur. J. Neurol. 15:1, e4-EOA (2008).
Streck et al., "Antitumor efficacy of AAV-mediated systemic delivery of interferon-beta", Cancer Gene Ther. 13:1, 99-106 (2006).
Gurguta et al., "Tongue and skin hyperpigmentation during PEG-interferon-alpha/ribavirin therapy in dark-skinned non-Caucasian patients with chronic hepatitis C", Am. J. Gastroenterol. 101:1, 197-198 (2006).
Kameyama et al., "Expression of melanocyte stimulating hormone receptors correlates with mammalian pigmentation, and can be modulated by interferons", J. Cell. Physiol. 137:1, 35-44 (1988).
Zimmerer et al., "Gene expression profiling reveals similarities between the in vitro and in vivo responses of immune effector cells to IFN-alpha", Clin. Cancer Res. 14:18, 5900-5906 (2008).
Carretero et al., "Analysis of HLA class I expression in progressing and regressing metastatic melanoma lesions after immunotherapy", Immunogenetics 60:8, 439-447 (2008).
Domingo-Domenech et al., "Serum protein s-100 predicts clinical outcome in patients with melanoma treated with adjuvant interferon—comparison with tyrosinase rt-PCR", Oncology 68:4-6, 341-349 (2005).
Terheyden et al., "Longitudinal analysis of MART-1/HLA-A2-reactive T cells over the course of melanoma progression", Scand. J. Immunol. 58:5, 566-571 (2003).
Ryuke et al., "Growth inhibition of subcutaneous mouse melanoma and induction of natural killer cells by liposome-mediated interferon-beta gene therapy", Melanoma Res. 13:4, 349-356 (2003).
Odaka et al., "Eradication of intraperitoneal and distant tumor by adenovirus-mediated interferon-beta gene therapy is attributable to induction of systemic immunity", Cancer Res. 61:16, 6201-6212 (2001).
DeLong et al., "Use of cyclooxygenase-2 inhibition to enhance the efficacy of immunotherapy", Cancer Res. 63:22, 7845-7852 (2003).
Birlea et al., "Cellular and molecular mechanisms involved in the action of vitamin D analogs targeting vitiligo depigmentation", Curr. Drug Targets 9:4, 345-359 (2008).
Fisher et al., "Effects of combined treatment with interferon and mezerein on melanogenesis and growth in human melanoma cells", J. Interferon Res. 5:1, 11-22 (1985).
Fisher et al., "Interferon inhibits melanogenesis in B-16 mouse melanoma cells", Biochem. Biophys. Res. Commun. 100:2, 823-830 (1981).
Takahashi et al., "Enhancement of antiproliferative activity of interferons by RNA interference-mediated silencing of SOCS gene expression in tumor cells", Cancer Sci. 99:8, 1650-1655 (2008).
Ekmekcioglu et al., "Killing of human melanoma cells induced by activation of class I interferon-regulated signaling pathways via MDA-7/IL-24", Cytokine. 43:1, 34-44 (2008).
Wang et al., "Impact of IFNalpha2b upon pSTAT3 and the MEK/ERK MAPK pathway in melanoma", Cancer Immunol. Immunother. 57:9, 1315-1321 (2008).
Jiang et al., "Poly I:C enhances cycloheximide-induced apoptosis of tumor cells through TLR3 pathway", BMC Cancer. 8:12, 1-8 (2008).
Domingo-Domenech et al., "Prognostic implications of protein S-100beta serum levels in the clinical outcome of high-risk melanoma patients", Tumour Biol. 28:5, 264-272 (2007).
Seya et al., "Case of rectal malignant melanoma showing immunohistochemical variability in a tumor", J. Nippon Med. Sch. 74:5, 377-381 (2007).
Kumar et al., "Raf inhibitor stabilizes receptor for the type I interferon but inhibits its anti-proliferative effects in human malignant melanoma cells", Cancer Biol. Ther. 6:9, 1437-1441 (2007).
Baker et al., "N-terminally PEGylated human interferon-beta-1a with improved pharmacokinetic properties and in vivo efficacy in a melanoma angiogenesis model", Bioconjug. Chem. 17:1, 179-188 (2006).
Kovarik et al., "Interferon-gamma, but not interferon-alpha, induces SOCS 3 expression in human melanoma cell lines", Melanoma Res. 15:6, 481-488 (2005).
Gollob et al., "Gene expression changes and signaling events associated with the direct antimelanoma effect of IFN-gamma", Cancer Res. 65:19, 8869-8877 (2005).
Jrosevic et al., "Expression of melanoma-associated antigens in melanoma cell cultures", Exp. Dermatol. 14:7, 491-497 (2005).
Zhou et al., "Persistence of multiple tumor-specific T-cell clones is associated with complete tumor regression in a melanoma patient receiving adoptive cell transfer therapy", J. Immunother. 28:1, 53-62 (2005).
Paul et al., "Treatment of locoregional metastases of malignant melanomas with radiotherapy and intralesional beta-interferon injection", Melanoma Res. 13:6, 611-617 (2003).
Sakamoto et al., "Treatment of primary malignant melanoma of the esophagus with endoscopic injection of interferon-beta combined with systemic chemotherapy: a case report", Gastrointest. Endosc. 57:6, 773-777 (2003).
Wolf et al., "Topical imiquimod in the treatment of metastatic melanoma to skin", Arch. Dermatol. 139:3, 273-276 (2003).
McCarty et al., "Evidence for the causal role of endogenous interferon-alpha/beta in the regulation of angiogenesis, tumorigenicity, and metastasis of cutaneous neoplasms", Clin. Exp. Metastasis 19:7, 609-615 (2002).
Kanther, "Erratum of "A phase I clinical trial of single-dose intrapleural IFN-beta gene transfer for malignant pleural mesothelioma and metastatic pleural effusions: high rate of antitumor immune responses"", Clin. Cancer. Res. 13:17, 5226-EOA (2007).
Koon et al., "Autoimmunity and immunotherapy for cancer", N. Engl. J. Med. 354:7, 758-760 (2006).
Slingluff et al., "Immunity to melanoma antigens: from self-tolerance to immunotherapy", Adv. Immunol. 90, 243-295 (2006).
Till et al., "Adoptive immunotherapy for indolent non-Hodgkin lymphoma and mantle cell lymphoma using genetically autologous CD20-specific T cells", Blood, 112:6, 2261-2271 (2008).
Cooper, "Test-driving CARs", Blood, 112:6, 2172-2173 (2008).
Adamina et al., "Intranodal Immunization With a Vaccinia Virus Encoding Multiple Antigenic Epitopes and Costimulatory Molecules in Metastatic Melanoma," *Mol. Ther*. 18:651-659, 2010. [Epub ahead of print: Nov. 24, 2009.]
Al-Ghoul et al., "Comparative Proteomic Analysis of Matched Primary and Metastatic Melanoma Cell Lines," *J. Proteome Res*. 7:4107-4118, 2008.
Ayyoub et al., "CD4+ T Cell Responses to SSX-4 in Melanoma Patients," *J. Immunol*. 174:5092-5099, 2005.
Bassi et al., "HMGB1 as an Autocrine Stimulus in Human T98G Glioblastoma Cells: Role in Cell Growth and Migration," *J. Neurooncol*. 87:23-33, 2008. [Epub Nov. 2, 2007.]
Bilzer et al., "Antigen Variation in a Human Glioblastoma: From the Primary Tumor to the Second Recurrence, Permanent Cell Line and Xenotransplantation Tumors," *Anticancer Res*. 11:547-553, 1991. (Abstract Only).
Bodey et al., "Immunocytochemical Detection of Prostate Specific Antigen Expression in Human Primary and Metastatic Melanomas," *Anticancer Res*. 17:2343-2346, 1997. (Abstract Only).
Boon et al., "Comparison of Medulloblastoma and Normal Neural Transcriptomes Identifies a Restricted Set of Activated Genes," *Oncogene* 22:7687-7694, 2003.
Castiglia et al., "Concomitant Activation of Wnt Pathway and Loss of Mismatch Repair Function in Human Melanoma," *Genes Chromosomes Cancer* 47:614-624, 2008. (Abstract Only).
Chi et al., "Molecular Detection of Tumor-Associated Antigens Shared by Human Cutaneous Melanomas and Gliomas," *Am. J. Pathol*. 150:2143-2152, 1997.
Clark et al., "Wilms Tumor 1 Expression in Malignant Gliomas and Correlation of +KTS Isoforms with p53 Status," *J. Neurosurg*. 107:586-592, 2007.
Cruz-Sanchez et al., "Medulloblastoma. An Immunohistological Study of 50 Cases," *Acta Neuropathol*. 79:205-210, 1989. (Abstract Only).

Dangoor et al., "Clinical and Immunological Responses in Metastatic Melanoma Patients Vaccinated with a High-Dose Poly-Epitope Vaccine," *Cancer Immunol. Immunother*. (p. 1-11) [Epub ahead of print: Dec. 31, 2009.]

Dardousis et al., "Identification of Differentially Expressed Genes Involved in the Formation of Multicellular Tumor Spheroids by HT-29 Colon Carcinoma Cells," *Mol. Ther*. 15:94-102, 2007.

De Panfilis et al., "Cytoplasmic β-Catenin is Lacking in a Subset of Melanoma-Associated Naevi, But is Detectable in Naevus-Associated Melanomas: Potential Implications for Melanoma Tumorigenesis?" *Br. J. Dermatol*. 160:600-608, 2009.

Diaz et al., "Anti-Ganglioside Anti-Idiotypic Monoclonal Antibody-Based Cancer Vaccine Induces Apoptosis and Antiangiogenic Effect in a Metastatic Lung Carcinoma," *Cancer Immunol. Immunother*. 58:1117-1128, 2009a. [Epub ahead of print: Dec. 10, 2008.]

Diaz et al., "Epidermal Growth Factor Receptor Modulates the Tumorigenic Potential of Melanoma," *Front. Biosci*. 14:159-166, 2009b.

Dissanayake et al., "Wnt5A Regulates Expression of Tumor-Associated Antigens in Melanoma via Changes in Signal Transducers and Activators of Transcription 3 Phosphorylation," *Cancer Res*. 68:10205-10214, 2008.

du Plessis et al., "Phenotypic and Genotypic Characterization of Glioblastoma Multiforme with Epithelial Differentiation and Adenoid Formations," *Clin. Neuropathol*. 23:141-148, 2004. (Abstract Only).

Dunn et al., "Enhancement of Human Melanoma Antigen Expression by IFN-β," *J. Immunol*. 179:2134-2142, 2007.

Egland et al., "Characterization of Overlapping *XAGE-1* Transcripts Encoding a Cancer Testis Antigen Expressed in Lung, Breast, and Other Types of Cancers," *Mol. Cancer Ther*. 1:441-450, 2002.

Eichmüller et al., "mRNA Expression of Tumor-Associated Antigens in Melanoma Tissues and Cell Lines," *Exp. Dermatol*. 11:292-301, 2002.

Felsberg et al., "Prognostic Significance of Molecular Markers and Extent of Resection in Primary Glioblastoma Patients," *Clin. Cancer Res*. 15:6683-6693, 2009. [Epub Oct. 27, 2009.]

Furukawa et al., "Molecules in the Signaling Pathway Activated by Gangliosides can be Targets of Therapeutics for Malignant Melanomas," *Proteomics* 8:3312-3316, 2008.

George et al., "Bcl-2 siRNA Augments Taxol Mediated Apoptotic Death in Human Glioblastoma U138MG and U251MG Cells," *Neurochem. Res*. 34:66-78, 2009. [Epub Mar. 21, 2008.]

Graner et al., "Heat Shock Protein 70-Binding Protein 1 is Highly Expressed in High-Grade Gliomas, Interacts with Multiple Heat Shock Protein 70 Family Members, and Specifically Binds Brain Tumor Cell Surfaces," *Cancer Sci*. 100:1870-1879, 2009. [Epub Jul. 1, 2009.] (Abstract Only).

Harada et al., "Growth Inhibition of Human Glioma Cells by Transfection-Induced P21 and its Effects on Telomerase Activity," *J. Neurooncol*. 47:39-46, 2000. (Abstract Only).

Heinzel et al., "The Self Peptide Annexin II (208-223) Presented by Dendritic Cells Sensitizes Autologous CD4+ T Lymphocytes to Recognize Melanoma Cells," *Cancer Immunol Immunother*. 49:671-678, 2001.

Helling et al., "$G_{M2}$-KLH Conjugate Vaccine: Increased Immunogenicity in Melanoma Patients after Administration with Immunological Adjuvant QS-21," *Cancer Res*. 55:2783-2788, 1995.

Ishiguro et al., "Identification of Genes Differentially Expressed in B16 Murine Melanoma Sublines with Different Metastatic Potentials," *Cancer Res*. 56:875-879, 1996.

Ito et al., "Inhibition of Heat Shock Protein 90 Sensitizes Melanoma Cells to Thermosensitive Ferromagnetic Particle-Mediated Hyperthermia with Low Curie Temperature," *Cancer Sci*. 100:558-564, 2009.

Janjic et al., "Spontaneous CD4+ T Cell Responses Against TRAG-3 in Patients with Melanoma and Breast Cancers," *J. Immunol*. 177:2717-2727, 2006.

Javelaud et al., "Stable Overexpression of Smad7 in Human Melanoma Cells Inhibits Their Tumorigenicity In Vitro and In Vivo," *Oncogene* 24:7624-7629, 2005.

Jouneau et al., "Plasticity of Cadherin-Catenin Expression in the Melanocyte Lineage," *Pigment Cell Res*. 13:260-272, 2000.

Kageshita et al., "Widespread Expression of Parathyroid Hormone-Related Peptide in Melanocytic Cells," *Br. J. Dermatol*. 148:533-538, 2003.

Karpusas et al., "The Crystal Structure of Human Interferon β at 2.2-Å Resolution," *Proc. Natl. Acad. Sci. USA* 94:11813-11818, 1997.

Kawakami et al., "The Use of Melanosomal Proteins in the Immunotherapy of Melanoma," *J. Immunother*. 21:237-246, 1998. (Abstract Only).

Kesavan et al., "Annexin A2 Is a Molecular Target for TM601, a Peptide with Tumor-Targeting and Anti-Angiogenic Effects," *J. Biol. Chem*. 285:4366-4374, 2010. [Epub Dec. 15, 2009.]

Kim et al., "Ubiquitin C-Terminal Hydrolase-L1 is a Key Regulator of Tumor Cell Invasion and Metastasis," *Oncogene* 28:117-127, 2009.

Kjellman et al., "Expression of TGF-β Isoforms, TGF-β Receptors, and SMAD Molecules at Different Stages of Human Glioma," *Int. J. Cancer* 89:251-258, 2000.

Korshunov et al., "Immunohistochemical Markers for Prognosis of Cerebral Glioblastomas," *J. Neurooncol*. 58:217-236, 2002.

Kreizenbeck et al., "Prognostic Significance of Cadherin-Based Adhesion Molecules in Cutaneous Malignant Melanoma," *Cancer Epidemiol. Biomarkers Prev*. 17:949-958, 2008.

Krex et al., "Identification of Uncommon Chromosomal Aberrations in the Neuroglioma Cell Line H4 by Spectral Karyotyping," *J. Neurooncol*. 52:119-128, 2001. (Abstract Only).

Kurnick et al., "A Novel Autocrine Pathway of Tumor Escape from Immune Recognition: Melanoma Cell Lines Produce a Soluble Protein that Diminishes Expression of the Gene Encoding the Melanocyte Lineage Melan-A/MART-1 Antigen Through Down-Modulation of its Promoter," *J. Immunol*. 167:1204-1211, 2001.

Lo et al., "Control Mechanisms of Differential Translation of Hsp90 Isoforms in 9L Rat Gliosarcoma Cells," *J. Cell. Biochem*. 107:418-427, 2009. (Abstract Only).

Lueth et al., "Somatic Mitochondrial Mutations in Pilocytic Astrocytoma," *Cancer Genet. Cytogenet*. 192:30-35, 2009.

Maellaro et al., "Different Effects of Interferon-α on Melanoma Cell Lines: A Study on Telomerase Reverse Transcriptase, Telomerase Activity and Apoptosis," *Br. J. Dermatol*. 148:1115-1124, 2003.

McGuinness et al., "Dipeptidyl Peptidase IV (DPPIV), A Candidate Tumor Suppressor Gene in Melanomas is Silenced by Promoter Methylation," *Front. Biosci*. 13:2435-2443, 2008.

Miracco et al., "Evaluation of MDR1, LRP, MRP, and Topoisomerase IIalpha Gene mRNA Transcripts Before and After Interferon-alpha, and Correlation with the mRNA Expression Level of the Telomerase Subunits hTERT and TEP1 in Five Unselected Human Melanoma Cell Lines," *Int. J. Oncol*. 23:213-220, 2003. (Abstract Only).

Misaki et al., "Correlation of γ-Catenin Expression with Good Prognosis in Medulloblastomas," *J. Neurosurg*. 102:197-206, 2005.

Missotten et al., "Heat Shock Protein Expression in the Eye and in Uveal Melanoma," *Invest. Ophthalmol. Vis. Sci*. 44:3059-3065, 2003.

Molina-Ortiz et al., "Overexpression of E-Cadherin on Melanoma Cells Inhibits Chemokine-Promoted Invasion Involving p190RhoGAP/p120ctn-Dependent Inactivation of RhoA," *J. Biol. Chem*. 284:15147-15157, 2009. [Epub Mar. 17, 2009.]

Moustakas, "TGF-β Targets *PAX3* to Control Melanocyte Differentiation," *Dev. Cell* 15:797-799, 2008.

Muchemwa et al., "Differential Expression of Heat Shock Protein 105 in Melanoma and Melanocytic Naevi," *Melanoma Res*. 18:166-171, 2008.

Nakabayashi et al., "Clinico-Pathological Significance of RCAS1 Expression in Gliomas: A Potential Mechanism of Tumor Immune Escape," *Cancer Lett*. 246:182-189, 2007.

Nishimura et al., "Key Roles for Transforming Growth Factor β in Melanocyte Stem Cell Maintenance," *Cell. Stem. Cell*. 6:130-140, 2010.

Novellino et al., "A Listing of Human Tumor Antigens Recognized by T Cells," *Cancer Immunol. Immunother*. 54:187-207, 2005.

Oba-Shinjo et al., "Cancer-Testis (CT) Antigen Expression in Medulloblastoma," *Cancer Immun*. 8:7, 2008. (p. 1-7).

Okada et al., "Immunotherapeutic Approaches for Glioma," *Crit. Rev. Immunol*. 29, 2009. (Submitted in final edited manuscript form, p. 1-55).

Osorio et al., "Heterophilic NeuGcGM3 Ganglioside Cancer Vaccine in Advanced Melanoma Patients: Results of a Phase Ib/IIa Study," *Cancer Biol. Ther.* 7:488-495, 2008.
Palm et al., "Expression Profiling of Ependymomas Unravels Localization and Tumor Grade-Specific Tumorigenesis," *Cancer* 115:3955-3968, 2009.
Pandya et al., "Interaction of Human Heat Shock Protein 70 with Tumor-Associated Peptides," *Biol. Chem.* 390:305-312, 2009.
Passeron et al., "Upregulation of SOX9 Inhibits the Growth of Human and Mouse Melanomas and Restores their Sensitivity to Retinoic Acid," *J. Clin. Invest.* 119:954-963, 2009.
Patel et al., "Enhanced Suppression of Melanoma Tumor Growth and Metastasis by Combined Therapy with Anti-VEGF Receptor and Anti-TYRP-1/gp75 Monoclonal Antibodies," *Anticancer Res.* 28:2679-2686, 2008.
Pavoni et al., "Selection, Affinity Maturation, and Characterization of a Human scFv Antibody Against CEA Protein," *BMC Cancer* 6:41, 2006. (p. 1-15).
Pethiyagoda et al., "Dipeptidyl Peptidase IV (DPPIV) Inhibits Cellular Invasion of Melanoma Cells," *Clin. Exp. Metastasis* 18:391-400, 2001.
Pilla et al., "A Phase II Trial of Vaccination with Autologous, Tumor-Derived Heat-Shock Protein Peptide Complexes Gp96, in Combination with GM-CSF and Interferon-α in Metastatic Melanoma Patients," *Cancer Immunol. Immunother.* 55:958-968, 2006.
Przybyto et al., "β1-6 Branching of Cell Surface Glycoproteins May Contribute to Uveal Melanoma Progression by Up-Regulating Cell Motility," *Mol. Vis.* 14:625-636, 2008.
Qi et al., "cDNA Microarray in Isolation of Novel Differentially Expressed Genes Related to Human Glioma and Clone of a Novel Full-Length Gene," *Chin. Med. J. (Engl.)* 118:799-805, 2005.
Rapanotti et al., "Melanoma-Associated Markers Expression in Blood: MUC-18 is Associated with Advanced Stages in Melanoma Patients," *Br. J. Dermatol.* 160:338-344, 2009.
Rappl et al., "EGFR-Dependent Migration of Glial Cells is Mediated by Reorganisation of N-Cadherin," *J. Cell. Sci.* 121:4089-4097, 2008. [Epub Nov. 25, 2008.]
Rivoltini et al., "Human Tumor-Derived Heat Shock Protein 96 Mediates In Vitro Activation and In Vivo Expansion of Melanoma- and Colon Carcinoma-Specific T Cells," *J. Immunol.* 171:3467-3474, 2003.
Robbins et al., "A Mutated β-Catenin Gene Encodes a Melanoma-Specific Antigen Recognized by Tumor Infiltrating Lymphocytes," *J. Exp. Med.* 183:1185-1192, 1996.
Rogers et al., "An Investigation of WNT Pathway Activation and Association with Survival in Central Nervous System Primitive Neuroectodermal Tumours (CNS PNET)," *Br. J. Cancer* 100:1292-1302, 2009.
Romero et al., "Multiple Specificities in the Repertoire of a Melanoma Patient's Cytolytic T Lymphocytes Directed Against Tumor Antigen MAGE-1.A1," *J. Exp. Med.* 182:1019-1028, 1995.
Rondepierre et al., "Proteomic Studies of B16 Lines: Involvement of Annexin A1 in Melanoma Dissemination," *Biochim. Biophys. Acta* 1794:61-69, 2009.
Rossier-Pansier et al., "Compartmentalization in Membrane Rafts Defines a Pool of N-Cadherin Associated with Catenins and not Engaged in Cell-Cell Junctions in Melanoma Cells," *J. Cell. Biochem.* 103:957-971, 2008.
Rye et al., "Invasion Potential and N-Acetylgalactosamine Expression in a Human Melanoma Model," *Int. J. Cancer* 75:609-614, 1998.
Sahin et al., "Expression of Cancer Testis Genes in Human Brain Tumors," *Clin. Cancer Res.* 6:3916-3922, 2000.
Saikali et al., "Expression of Nine Tumour Antigens in a Series of Human Glioblastoma Multiforme: Interest of EGFRvIII, IL-13Ralpha2, gp100 and TRP-2 for Immunotherapy," *J. Neurooncol.* 81:139-148, 2007. [Epub Sep. 27, 2006.]
Satoh et al., "Ubiquitin C-Terminal Hydrolase-L1 (PGP9.5) Expression in Human Neural Cell Lines Following Induction of Neuronal Differentiation and Exposure to Cytokines, Neurotrophic Factors or Heat Stress," *Neuropathol. Appl. Neurobiol.* 27:95-104, 2001. (Abstract Only).
Schanzer et al., "A Human Cytokine/Single-Chain Antibody Fusion Protein for Simultaneous Delivery of GM-CSF and IL-2 to Ep-CAM Overexpressing Tumor Cells," *Cancer Immun.* 6:4, 2006. (p. 1-11).
Schick et al., "TEL/ETV6 is a Signal Transducer and Activator of Transcription 3 (Stat3)-Induced Repressor of Stat3 Activity," *J. Biol. Chem.* 279:38787-38796, 2004.
Schittenhelm et al., "Comparative Analysis of Annexin-1 in Neuroepithelial Tumors Shows Altered Expression with the Grade of Malignancy but is not Associated with Survival," *Mod. Pathol.* 22:1600-1611, 2009.
Segal et al., "Identification of Cancer-Testis Genes Expressed by Melanoma and Soft Tissue Sarcoma Using Bioinformatics," *Cancer Immun.* 5:2, 2005. (p. 1-9).
Senda et al., "Three-Dimensional Crystal Structure of Recombinant Murine Interferon-62 ," *EMBO J.* 11:3193-3201, 1992.
Shimada et al., "Nestin Expression as a New Marker in Malignant Peripheral Nerve Sheath Tumors," *Pathol. Int.* 57:60-67, 2007.
Shinoura et al., "Expression of N-Cadherin and α-Cadherin in Astrocytomas and Glioblastomas," *Br. J. Cancer* 72:627-633, 1995.
Sigalotti et al., "Cancer Testis Antigens in Human Melanoma Stem Cells: Expression, Distribution, and Methylation Status," *J. Cell. Physiol.* 215:287-291, 2008.
Slingluff et al., "Helper T-Cell Responses and Clinical Activity of a Melanoma Vaccine with Multiple Peptides from MAGE and Melanocytic Differentiation Antigens," *J. Clin. Oncol.* 26:4973-4980, 2008.
Staib et al., "Cross-Presentation of Human Melanoma Peptide Antigen MART-1 to CTLs from In Vitro Reconstituted gp96/MART-1 Complexes," *Cancer Immun.* 4:3, 2004. (p. 1-16).
Stremenova et al., "Expression and Enzymatic Activity of Dipeptidyl Peptidase-IV in Human Astrocytic Tumours are Associated with Tumour Grade," *Int. J. Oncol.* 31:785-792, 2007.
Takata et al., "Molecular Pathogenesis of Malignant Melanoma: A Different Perspective from the Studies of Melanocytic Nevus and Acral Melanoma," *Pigment Cell Melanoma Res.* 23:64-71, 2010. [Epub Sep. 25, 2009.]
Tatenhorst et al., "Knockdown of Annexin 2 Decreases Migration of Human Glioma Cells in vitro," *Neuropathol. Appl. Neurobiol.* 32:271-277, 2006.
Teti et al., "Transforming Growth Factorβ Enhances Adhesion of Melanoma Cells to the Endothelium In Vitro," *Int. J. Cancer* 72:1013-1020, 1997.
Tuominen et al., "Non-Erythroid Spectrin (fodrin) in Cutaneous Tumours: Diminished in Cell Membranes, Increased in the Cytoplasm," *Br. J. Dermatol.* 135:576-580, 1996. (Abstract Only).
Vourc'h-Jourdain et al., "Melanoma Gene Expression and Clinical Course," *Arch. Dermatol. Res.* 301:673-679, 2009. [Epub Mar. 27, 2009.]
Vukelić et al., "Human Gliosarcoma-Associated Ganglioside Composition is Complex and Distinctive as Evidenced by High-Performance Mass Spectrometric Determination and Structural Characterization," *Glycobiology* 17:504-515, 2007. [Epub Feb. 9, 2007.]
Wagner et al., "The Wilms' Tumor Suppressor WT1 is Associated with Melanoma Proliferation," *Pflugers Arch.* 455:839-847, 2008. (Abstract Only).
Wang et al., "Cloning Genes Encoding MHC Class II-Restricted Antigens: Mutated CDC27 as a Tumor Antigen," *Science* 284:1351-1354, 1999.
Wang et al., "Targeted Immunotherapy Using Reconstituted Chaperone Complexes of Heat Shock Protein 110 and Melanoma-Associated Antigen gp100," *Cancer Res.* 63:2553-2560, 2003.
Wang et al., "Mitf-Mdel, a Novel Melanocyte/Melanoma-Specific Isoform of Microphthalmia-Associated Transcription Factor-M, as a Candidate Biomarker for Melanoma," *BMC Medicine* 8:14, 2010 (p. 1-22).
Wierzbicki et al., "Immunization with a Mimotope of GD2 Ganglioside Induces CD8+ T Cells that Recognize Cell Adhesion Molecules on Tumor Cells," *J. Immunol.* 181:6644-6653, 2008.
Wood et al., "An Adjuvant Autologous Therapeutic Vaccine (HSPPC-96; Vitespen) Versus Observation Alone for Patients at High Risk of Recurrence after Nephrectomy for Renal Cell Carcinoma: A Multicentre, Open-Label, Randomised Phase III Trial," *Lancet* 372:145-154, 2008.

Wu et al., "Identification of EGFRvIII-Derived CTL Epitopes Restricted by HLA A0201 for Dendritic Cell Based Immunotherapy of Gliomas," *J. Neurooncol.* 76:23-30, 2006.

Xia et al., "Identification of the Role of Smad Interacting Protein 1 (SIP1) in Glioma," *J. Neurooncol.* 97:225-232, 2010. [Epub ahead of print: Oct. 6, 2009.]

Yajima et al., "Immunologic Evaluation of Personalized Peptide Vaccination for Patients with Advanced Malignant Glioma," *Clin. Cancer Res.* 11:5900-5911, 2005.

Yasuda et al., "Differential Expression of ras Oncogene Products Among the Types of Human Melanomas and Melanocytic Nevi," *J. Invest. Dermatol.* 93:54-59, 1989. (Abstract Only).

Zhang et al., "Antigenic Profiling of Glioma Cells to Generate Allogeneic Vaccines or Dendritic Cell-Based Therapeutics," *Clin. Cancer Res.* 13:566-575, 2007.

Beuret et al., "Up-Regulation of MET Expression by α-Melanocyte-Stimulating Hormone and MITF Allows Hepatocyte Growth Factor to Protect Melanocytes and Melanoma Cells from Apoptosis," *J. Biol. Chem.* 282:14140-14147, 2007.

Brouwenstijn et al., "Transcription of the Gene Encoding Melanoma-Associated Antigen gp100 in Tissues and Cell Lines Other than Those of the Melanocytic Lineage," *Br. J. Cancer* 76:1562-1566, 1997.

Buscà et al., "Hypoxia-Inducible Factor 1α Is a New Target of Microphthalmia-Associated Transcription Factor (MITF) in Melanoma Cells," *J. Cell Biol.* 170:49-59, 2005.

Carreira et al., "Mitf Regulation of Dia1 Controls Melanoma Proliferation and Invasiveness," *Genes Dev.* 20:3426-3439, 2006.

Carreira et al., "Mitf Cooperates with Rb1 and Activates $p21^{Cip1}$ Expression to Regulate Cell Cycle Progression," *Nature* 433:764-769, 2005.

Carreira et al., "The Gene Encoding the T-Box Factor Tbx2 Is a Target for the Microphthalmia-Associated Transcription Factor in Melanocytes," *J. Biol. Chem.* 275:21920-21927, 2000.

Cheli et al., "Fifteen-Year Quest for Microphthalmia-Associated Transcription Factor Target Genes," *Pigment Cell Melanoma Res.* 23:27-40, 2009.

Cronin et al., "Frequent Mutations in the MITF Pathway in Melanoma," *Pigment Cell Melanoma Res.* 22:435-444, 2009. (Submitted in Author Manuscript form, pp. 1-17).

Dietrich et al., "Prevalent Role of TCR α-Chain in the Selection of the Preimmune Repertoire Specific for a Human Tumor-Associated Self-Antigen," *J. Immunol.* 170:5103-5109, 2003.

Dong et al., "Suppression of Angiogenesis, Tumorigenicity, and Metastasis by Human Prostate Cancer Cells Engineered to Produce Interferon-β," *Cancer Res.* 59:872-879, 1999.

Du et al., "Critical Role of CDK2 for Melanoma Growth Linked to Its Melanocyte-Specific Transcriptional Regulation by MITF," *Cancer Cell* 6:565-576, 2004.

Du et al., "MLANA/MART1 and SILV/PMEL17/GP100 Are Transcriptionally Regulated by MITF in Melanocytes and Melanoma," *Am. J. Pathol.* 163:333-343, 2003.

Dynek et al., "Microphthalmia-Associated Transcription Factor Is a Critical Transcriptional Regulator of Melanoma Inhibitor of Apoptosis in Melanoma," *Cancer Res.* 68:3124-3132, 2008.

Goding, "Mitf from Neural Crest to Melanoma: Signal Transduction and Transcription in the Melanocyte Lineage," *Genes Dev.* 14:1712-1728, 2000.

Hou and Pavan, "Transcriptional and Signaling Regulation in Neural Crest Stem Cell-Derived Melanocyte Development: Do All Roads Lead to Mitf?" *Cell Res.* 18:1163-1176, 2008.

Jaitin et al., "Inquiring into the Differential Action of Interferons (IFNs): An IFN-α2 Mutant with Enhanced Affinity to IFNAR1 Is Functionally Similar to IFN-β," *Mol. Cell. Biol.* 26:1888-1897, 2006.

Jorritsma et al., "Selecting Highly Affine and Well-Expressed TCRs for Gene Therapy of Melanoma," *Blood* 110:3564-3572, 2007.

Kawakami et al., "Cloning of the Gene Coding for a Shared Human Melanoma Antigen Recognized by Autologous T Cells Infiltrating Into Tumor," *Proc. Natl. Acad. Sci. USA* 91:3515-3519, 1994.

Liu et al., "MiTF Regulates Cellular Response to Reactive Oxygen Species through Transcriptional Regulation of APE-1/Ref-1," *J. Invest. Dermatol.* 129:422-431, 2009.

Loercher et al., "MITF Links Differentiation with Cell Cycle Arrest in Melanocytes by Transcriptional Activation of INK4A," *J. Cell Biol.* 168:35-40, 2005.

Ludwig et al., "Melanocyte-Specific Expression of Dopachrome Tautomerase Is Dependent on Synergistic Gene Activation by the Sox10 and MITF Transcription Factors," *FEBS Lett.* 556:236-244, 2004.

Mark et al., "Site-Specific Mutagenesis of the Human Fibroblast Interferon Gene," *Proc. Natl. Acad. Sci. USA* 81:5662-5666, 1984.

Mateo et al., "An HLA-A2 Polyepitope Vaccine for Melanoma Immunotherapy," *J. Immunol.* 163:4058-4063, 1999.

McGill et al., "Bcl2 Regulation by the Melanocyte Master Regulator Mitf Modulates Lineage Survival and Melanoma Cell Viability," *Cell* 109:707-718, 2002.

Murakami and Arnheiter, "Sumolyation Modulates Transcriptional Activity of MITF in a Promoter-Specific Manner," *Pigment Cell Res.* 18:265-277, 2005. (Submitted in Author Manuscript form, pp. 1-24).

Pestka et al., "Interferons, Interferon-Like Cytokines, and Their Receptors," *Immunol. Rev.* 202:8-32, 2004.

Ramirez-Montagut et al., "Melanoma Antigen Recognition by Tumour-Infiltrating T Lymphocytes (TIL): Effect of Differential Expression of Melan-A/MART-1," *Clin. Exp. Immunol.* 119:11-18, 2000.

Rinehart et al., "Phase I/II Trial of Interferon-β-Serine in Patients with Renal Cell Carcinoma; Immunological and Biological Effects," *Cancer Res.* 47:2481-2485, 1987.

Runkel et al., "Systematic Mutational Mapping of Sites on Human Interferon-β-1a that Are Important for Receptor Binding and Functional Activity," *Biochemistry* 39:2538-2551, 2000.

Sensi et al., "Cytotoxic T-Lymphocyte Clones from Different Patients Display Limited T-Cell-Receptor Variable-Region Gene Usage in HLA-A2-Restricted Recognition of the Melanoma Antigen Melan-A/MART-1," *Proc. Natl. Acad. Sci. USA* 92:5674-5678, 1995.

Steingrimsson et al., "Melanocytes and the *Microphthalmia* Transcription Factor Network," *Annu. Rev. Genet.* 38:365-411, Figures C-1-C-4, 2004.

Tsujimura et al., "Involvement of Transcription Factor Encoded by the mi Locus in the Expression of c-kit Receptor Tyrosine Kinase in Cultured Mast Cells of Mice," *Blood* 88:1225-1233, 1996.

Turque et al., "Characterization of a New Melanocyte-Specific Gene (*QNR-71*) Expressed in v-*myc*-Transformed Quail Neuroretina," *EMBO J.* 15:3338-3350, 1996.

International Search Report (PCT/US03/27125), completed Jun. 11, 2004, mailed Aug. 3, 2004.

Supplementary European Search Report (EP 03 74 9229), completed Jun. 18, 2010, mailed Jul. 8, 2010.

Diseases of the Colon Rectum, *Annual Meeting of the American Society of Colon and Rectal Surgeons*, Jun. 2-7, 2011, vol. 44, No. 4, pp. A1-A4.

Ahlers, et al., "Cytokine-In-Adjuvant Steering of the Immune Response Phenotype to HIV-1 Vaccine Constructs," *The J. of Immunology*, (1997) vol. 158, pp. 3947-3958.

Artursson, et al., "Molecular Cloning of a Gene Encoding Porcine Interferon-β", *J. of Interferon Research*, (1992), vol. 12, pp. 153-160.

Bada, et al., "Toxicity of a GM3 cancer vaccine in *Macaca fascicularis* monkey: a 12-month study," *Human and Experimental Toxicology*, (2002), vol. 21, pp. 263-267.

Bakker, et al., "Melanocyte Lineage-specific Antigen gp100 Is Recognized by Melanoma-derived Tumor-Infiltrating Lymphocytes," *Journal of Experimental Medicine*, (Mar. 1994), vol. 179, pp. 1005-1009.

Basu, et al., "Detection and Purification of a Novel 72 kDa Glycoprotein Male Breast Tumor Associated Antigen," *Int. J. Cancer*, 2003, vol. 105, pp. 377-383.

Baumgrass, et al., "Reversible Inhibition of Calcineurin by the Polyphenolic Aldehyde Gossypol," *Journal of Biological Chemistry*, (2001), No. 61, vol. 276, pp. 47914-47921.

Becker, et al., "Tumor escape mechanisms from Immunosurveillance: induction of unresponsiveness in a specific MCH-restricted CD4+ human T cell clone by the autologous MHC class II+ melanoma," *International Immunology*, (1993), No. 12, vol. 5, pp. 1501-1508.

Boon, et al., "Tumor Antigens Recognized by T Lymphocytes," *Annu. Rev. Immunol.*, (1994), vol. 12, pp. 337-365.
Buchsbaum, et al., "Targeting Strategies for Cancer Radiotherapy," *Clinical Cancer Research*, (Oct. 1999)(Supp.), vol. 5, pp. 3048s-3055s.
Carr, et al., "Immunotherapy of Advance Breast Cancer with a Heterophilic Ganglioside (NeuGcGM3) Cancer Vaccine, " *J. of Clinical Oncology*, (2003), vol. 21, pp. 1015-1021.
Caudill, M. and Li, Z., "HSPPC-96: a personalized cancer vaccine," *Exper. Opin. Biol. Ther.*, (2001), vol. 1, No. 3, pp. 539-547.
Chen, et al., "Expressions of TRAG-3 antigen in non-small-cell lung carcinomas," *Lung Cancer*, (2002), vol. 38, pp. 101-102.
Chen, et al., "Identification of multiple cancer/testis antigens by allogenic antibody screening of a melanoma cell line library," *Proc. Natl. Acad. Sci.*, (Jun. 1998), vol. 95, pp. 6919-6923.
Chen, et al., "Induction of ErbB-2/neu-specific protective and therapeutic antitumor immunity using genetically modified dedritic cells: enhanced efficacy by cotransduction of gene encoding IL-12," *Gene Therapy*, (2001), vol. 8, pp. 316-323.
Chen, et al., "Serological analysis of Melan-A (MART-1), a melanocyte-specific protein homogeneously expressed in human melanomas," *Proc. Natl. Acad. Sci.*, (Jun. 1995), vol. 93, pp. 5915-5919.
Chen, et al., "Tumor cell membrane-bound heat shock protein 70 elicits antitumor immunity," *Immunology Letter*, (2002), vol. 84, pp. 81-87.
Clemons, et al., "Cerulein-induced Pacratitis in the Rat is Significantly Ameliorated by Treatment With MEK 1/2 Inhibitors U0126 and PD98059" *Pancreas*, (2002), vol. 25, No. 3, pp. 2512-259.
Cormler, et al., "Enhancement of Cellular Immunity in Melanoma Patients Immunized with a peptide from MART-1/Melan A," *Cancer J. Sci. Am.*, (1997), vol. 3, pp. 37-44.
Correale, et al., "Generation of Human Cytolytic T Lymphocyte Line Directed Aainst Prostate-Specific Antigen (PSA) Employing a PSA Oligoepitope Peptide" *The Journal of Immunology*, (1998), vol. 161, pp. 3186-3194.
Daheron, et al., "Identification of Several Genes Differentially Expressed During Progression of Chronis Myelogenous Leukemia," *Leukemia*, (1998), vol. 12, pp. 326-332.
Devine, et al., "The Breast Tumor-associated Epitope Defined by Monoclonal Antibody 3E1.2 Is an O-linked Mucin Carbohydrate Containing N-Glycolylneuraminic Acid," *Cancer Research*, (1991), vol. 51, pp. 5826-5836.
Dillman, et al., "Continuous Interleukin-2 and Tumor-Infiltrating Lymphocytes as Treatment of Advanced Melanoma," *Cancer*, (1991), vol. 68, pp. 1-8.
Disis, et al., "Flt3 Ligand as a faccine adjuvant in association with HER-2/neu peptide-based vaccines in patients with HER-2/neu-overexpressing cancers," *Blood*, (Apr. 15, 2002), vol. 99, No. 8, pp. 2845-2850.
Djuric, et al., "3, 5-bis(trifluoromethyl)pyrazoles: A Novel Class of NFAT Transcription Factor Regulator," *J. Med. Chem.*, (2000), vol. 43, pp. 2975-2981.
Doronina, et al., "Development of potent monocolonal antibody auristatin conjugates for cancer therapy," *Nature Biotechnology*, (Jul. 2003), vol. 21, No. 7, pp. 778-941.
Dredge, et al., "Adjuvants and the promotion of Th1-type cytokines in tumour immunotherapy," *Cancer Immunol Immunother*, (2002), vol. 51, pp. 521-531.
Dudley, et al., "Cancer Regression and Autoimmunity in Patients After Clonal Repopulation with Antitumor Lymphocytes," *Science*, (Oct. 25, 2002), vol. 298, pp. 850-854.
Durda, et al., "Induction of "Antigen Silencing" in Melanomas by Oncostatin M: Down-Modulation of Melanocyte Antigen Expression," *Molecular Cancer Research*, (Apr. 2003), vol. 1, pp. 411-419.
Eichmuller, et al., "Tumor-Specific Antigens in Cutaneous T-Cell Lymphoma: Expression and Sero-Reactivity," *Int. J. Cancer*, (2003), vol. 104, pp. 482-487.
Elzey, et al., "Immunization with Type 5f Advenovirus Recombinant for a Tumor Antigen in Combination with Recombinant Canarypox Virus (ALVAC) Cytokine Gene Delivery Induces Destruction of Established Prostate Tumors," *Int. J. Cancer*, (2001), vol. 94, pp. 842-849.

Emmert-Buck, et al., "Laser Capture Microdissection," *Science*, (Nov. 8, 1996), vol. 274, pp. 998-1001.
Englaro, et al., "Inhibition of the Mitogen-activated Protein Kinase Pathway Triggers B16 Melanoma Cell Differentiation," *J. of Biological Chemistry*, (1998), vol. 273, No. 16, pp. 9966-9970.
Faehling, et al., "Essential role of calcium in vascular endothelial growth factor A-induced signaling: mechanism of the antiangiogenic effect of carboxyamidotriazole," *The FASFB Journal*, (Nov. 2002), vol. 16, pp. 1805-1807.
Fong, et al., "Dendritic Cell-Based Xenoantigen Vaccination for Prostate Cancer Immunotherapy," *J. of Immunology*, (2001), vol. 167, pp. 7150-7156.
Fukumure, et al., "Tumor Necrosis Factor α-induced Leukocyte Adhesion in Normal and Tumor Vessels: Effect of Tumor Type. Transplantation Site, and Host Strain." *Cancer Research*, (Nov. 1, 1995), vol. 55, pp. 4824-4829.
Gattoni-Cell, S. and Cole, D., "Melanoma-Associated Tumor Antigens and Their Clinical Relevance to Immunotherapy," *Seminars in Oncology*, (Dec. 1996), vol. 23, pp. 754-758.
Gaugler, et al., "Human Gene MAGE-3 Codes for an Antigen Recognized on a Melanoma by Autologous Cytolytic T Lymphocytes," *J. Experimental Medicine*. (Mar. 1994), vol. 179, pp. 921-930.
Gray, P. and Goeddel, D., "Structure of the Human Immune Interferon Gene," *Nature*, (Aug. 1982), vol. 298, 859-863.
Greiner, et al., "Simultaneous expression of different immunogenic antigens in acute myeloid leukemia," *Experimental Hematology*, (2000), vol, 28, pp. 1413-1422.
Guadagni, et al., "Biological Response Modifiers as Adjuvants in Monoclonal Antibody-Based Treatment (Review)," in vivo, (1993), vol. 7, pp. 591-800.
Heike, et al., "Expression of Stress Protein gp96, A Tumor Rejection Antigen, in Human Colorectal Cancer," *Int. J. Cancer*, (2000), vol. 86, 489-493.
Hishii, et al., "In vivo accumulation of the same anti-melanoma T cell clone in two different metastatic sites,"*PNAS*, (Feb. 1997), vol. 94, pp. 1378-1383.
Hishii, et al., "Studies of the mechanism of cytolysis by tumour-infiltrating lymphocytes," *Clin. Exp. Immunol*. (1999), vol. 116, pp. 388-394.
Ikeda, et al., "Characterization of an Antigen That is Recognized on a Melanoma Showing Partial HLA Loss by CTL Expressing an NK Inhibitory Receptor," *Immunity*, (Feb. 1997), vol, 6. pp. 199-208.
Jaeger, et al., "Generation of Cytotoxic T-Cell Response with Synthetic Melanoma-Associated Peptides In Vivo: Implications for Tumor Vaccines with Melanoma-Associated Antigens," *Int J. Cancer*, (1996), vol. 86, pp. 162-189.
Jager, et al., "Granulocyte-Macrophage-Colony-Stimulating Factor Enhances Immune Responses to Melanoma-Associated Peptides in vivo," *Int. J. Cancer*, (1996), vol. 67, pp. 54-62.
Jager, et al., "Identification of a Tissue-specific Putative Transcription Factor In Breast Tissue by Serological Screening of a Breast Cancer Library," *Cancer Research*, (Mar. 1, 2001), pp. 2055-2061.
Jager, et al., "Identification of tumor-restricted antigens NY-BR-1, SCP-1, and a new cancer/testis-like antigen NW-BR-3 by serological screening of a testicular library with breast cancer serum," *Cancer Immunity*, (Jun. 28, 2002), vol. 2, pp. 5 (1-12).
Jager, et al., "Immunoselection in vivo: Independent Loss of MHC Class I and Melanocyte Differentiation Antigen Expression in Metastatic Melanoma," *Int. J. Cancer*, (1997), vol. 71, pp. 142-147.
Jager, et al., "Induction of primary NY-ESO-1 immunity: CD8+ T lymphocyte and antibody responses in peptide-vaccinated patients with, NY-ESA-1+ cancers," *PNAS*, (Oct. 24, 2000), vol. 97, No. 22, pp. 12198-12203.
Kan-Mitchell, et al., "Clonal analysis of in vivo activated CD8+ cytotoxic T lymphocytes from a melanoma patient responsive to active specific immunotherapy," *Cancer Immunol Immunother*, (1993), vol. 37, pp. 15-25.
Kawakami, et al, "Immunobiology of Human Melanoma Antigens MART-1 and gp 100 and their Use for Immuno-Gene Therapy," *Intem. Rev. Immunol.*, (1997), vol. 14, pp. 173-192.
Kawakami, et al., "Cloning of the Gene Coding for a Shared Human Melanoma Antigen Recognized by Autologous T cells infiltrating into tumor," *PNAS*, (Apr. 1994), vol. 91, pp, 3515-3519.

Kawakami, et al., "Human Melanoma Antigens Recognized by T Lymphocytes." *Keio J. Medicine*, (Jun. 1996), vol. 45, No. 2, pp. 100-108.

Kawakami, et al., "Identification of the Immunodominant Peptides of the MART-1 Human Melanoma Antigen Recognized by the Majority of HLA-A2-restricted Tumor Infiltrating Lymphocytes," *The J. of Experimental Medicine*, (Jul. 1994), vol. 180, pp. 347-352.

King, et al., "Microphthalmia Transcription Factor," *American Journal of Pathology*, (Sep. 1999), vol. 155, No. 3, pp. 731-738.

Koga, et al., "Identification of ribosomal proteins S2 and L10a as tumor antigens recognized by HLA-A26-restricted CTL," *Tissue Antigens*, (2003), vol. 61, pp. 136-145.

Kradin, et al., "Tumor-derived interleukin-2-dependent lymphocytes in adoptive immunotherapy of lung cancer," *Cancer Immunol Immunother*, (1987), vol. 24, pp. 76-85.

Kradin, et al., "Tumour-Infiltrating Lymphocytes and Interleukin-2 in Treatment of Advanced Cancer" *The Lancet*, (Mar. 18, 1989), pp. 577-580.

Kurnick, et al., "A Novel Autocrine Pathway of Tumor Escape from Immune Recognition: Melanoma Cell Lines Produce a Soluble Protein That Diminishes Expression of the Gene Encoding the Melanocyte Lineage Melan-A/MART-1 Antigen Through Down-Modulation of its Promoter," *The Journal of Immunology*, (2001), vol. 167, pp. 1204-1211.

Le Poole, et al., "Interferon-γ Reduces Melanosomal Antigen Expression and Recognition of Melanoma Cells by Cyotoxic T Cells," *Am. J. Pathol.*, (2002), vol. 160, pp. 521-528.

Lindgren, et al., "N-substituted benzamides inhibit nuclear factor-kB and nuclear factor of activated T cells activity while inducing activator protein 1 activity in T lymphocytes," *Molecular Immunology*, (2001), vol. 38, pp. 267-277.

Lundin, et al., "Sialyl Tn Is a Frequently Expressed Antigen in Colorectal Cancer: No Correlation with Patient Prognosis," *Oncology*, (1999), vol. 57, pp. 70-76.

Luo, et al., "Gene expression profiles of laser-captured adjacent neuronal subtypes," *Nature Medicine*, (1999), vol. 5, No. 1, pp. 117-122.

Luo, et al., "Transcription factor Fos-related antigen 1 is an effective target for a breast cancer vaccine," *PNAS*, (2003), vol. 100, No. 15, pp. 8850-8855.

Lyakh, et al., "Expression of NFAT-Family Proteins in Normal Human T Cells," Molecular and Cellular Biology (May 1997), vol. 17, No. 5, pp. 2475-2484.

Maeurer, et al., "Tumor Escape from Immune Recognition," *J. Clin. Invest.*, (1996), vol. 98, pp. 1633-1641.

Marchand, et al, "Tumor Regressions Observed in Patients with Metastatic Melanoma Treated with an Antigenic Peptide Encoded by Gene Mage-3 and Presented by HLA-A1," *Int. J. Cancer*, (1999), vol. 80, pp. 219-230.

Marincola, et al., "Analysis of Expression of the Melanoma-Associated Antigens MART-1 and gp100 in Metastatic Melanoma Cell Lines and in Situ Lesions." *J. of Immunotherapy*, (1996), vol. 19, No. 3, pp. 192-205.

Martinez, et al.. "Blockade of T-Cell Activation by Dithiocarbamates Involves Novel Mechanisms of Inhibition of Nuclear Factor of Activated T Cells," *Molecular and Cellular Biology*, (Nov. 1997), vol. 17 No. 11, pp. 6437-6447.

Marx, et al., "Rapamycin-FKBP Inhibits Cell Cycle Regulators of Proliferation in Vascular Smooth Muscle Cells," Circulation Research, (Mar. 1995), vol. 76. No. 3. pp. 412-417.

Michne, et al,. "Novel Inhibitors of the Nuclear Factor of Activated T Cells (NFAT)-Mediated Transcription of β-Galactosidase: Potential Immunosuppressive and Antiinflammatory Agents," *J. Med. Chem.*, (1995), vol. 38, pp. 2557-2569.

Miura, et al., "Laser Capture Microdissenction and Microarray Expression Analysis of Lung Adenocarcinoma Reveals Tobacco Smoking- and Prognosis-related Molecular Profiles," *Cancer Research*, (Jun. 2002), vol. 62, pp. 3244-3250.

Miyagi, et al., "Induction of Cellular Immune Responses to Tumor Cells and Peptides in Colorectal Cancer Patients by Vaccination with SART3 Peptides," *Clinical Cancer Research*, (Dec. 2001), vol. 7, pp. 3950-4962.

Morse, M., "Technology Evaluation: Theratope, Biomira Inc.," *Current Opinion in Molecular Therapeutics*, (2000), vol. 2, No. 4, pp. 453-458.

Mukherjee, et al., "Mucin 1-Specific immunotherapy in a Mouse Model of Spontaneous Breast Cancer," *Journal of Immunotherapy*, (2003), vol. 26, No. 1, pp. 47-82.

Nellssen, et al., "Molecular analysis of the hematepolesIs supporting osteoblastic cell line U2-OS," *Experimental Hematology*, (2000), vol. 28, pp. 422-432.

Nohria, et al., "Cytokines as Potential Vaccine Adjuvants," *Biotherapy*, (1994), vol. 7, pp. 261-269.

Oka, et al., "WT1 as a Novel Target Antigen for Cancer Immunotherapy," *Current Cancer Drug Targets*, (2002), vol. 2, pp. 45-54.

Osheroff, et al., "Interferon-Like Activity in an Anti-Interferon Anti-Idlotypic Hybridoma Antibody," *The J. of Immunology*, (Jul. 1985), vol. 1, No. 135, pp. 306-313.

Pandolfi, et al., "Expression of HLA-A2 Antigen in Human Melanoma Cell Lines and Its Role in T-Cell Recognition," *Cancer Research*, (Jun. 1991), vol. 51, pp. 3164-3170.

Pardoll, Drew, "Paracrine Cytokine Adjuvants in Cancer Immunotherapy," *Annual Review Immunotherapy*, (1995), vol. 13, pp. 399-415.

Pardoll, Drew, "Spinning Molecular Immunology Into Successful Immunotherapy," *Nature Reviews, Immunology*, (Apr. 2002), vol. 2, pp. 227-238.

Plunkett, et al., "Breast Cancer and the Immune System: Opportunities and Pitfalls," *Journal of Mammary Gland Biology and Neoplasia*, (2002), vol. 6, No. 4, pp. 467-475.

Pu, et al., "NFAT Transcription Factors Are Critical Survival Factors That Inhibit Cardiamyocyte Apoptosis During Phenylephrine Stimulation In Vitro," *Circulation Research*, (2003), vol. 92, pp. 725-731.

Ramirez-Montagut, et al., "Melanoma antigen recognition by tumor-infiltrating T lymphocytes (TIL): effect of differential expression of Melan-A/MART-1," *Clinical Expre. Immunol.* (2000), vol. 110, pp. 11-18.

Reinartz, et al., "Interleukin-6 Fused to an Anti-idiotype Antibody in a Vaccine Increases the Specific Humoral Immune Response Against CA125 (MUC)-16) Ovarian Cancer," Cancer Research, (2003), vol. 63, pp. 3234-3240.

Riker, et al., "Immune selection after antigen-specific immunotherapy of melanoma," *Surgery*, (1999), vol. 128, pp. 112-120.

Rivoltini, et al., "Induction of Tumor-Reactive CTL from Peripheral Blood and Tumor-Infiltrating Lymphocytes of Melanoma Patients by In Vitro Stimulation with an Immunodominant Peptide of the Human Melanoma Antigen MART-1," *The Journal of Immunology*, (1995), vol. 154, pp. 2257-2265.

Rode, et al., "PGP9.5, a new marker for human neuroendocrine tumours," *Histopathology*, (1985), vol. 9, pp. 147-158.

Roehrborn, et al., "Variability of Repeated Serum Prostate-Specific Antigen (PSA) Measurements Within Less Than 90 Days in a Well-Defined Patient Population," *Urology*, (1998), vol. 47, No. 1, pp. 59-66.

Rosenberg, et al., "Immunologic and therapeutic evaluation of a synthetic peptide vaccine for the treatment of patients with metastatic melanoma," *Nature Medicine*, (Mar. 1998), vol. 4, No. 3, pp. 321-327.

Rosenberg, et al., "Use of Tumor-Infiltrating Lymphocytes and Interleukin-2 in the Immunotherapy of Patients with Metastatic Melanoma," *The New England Journal of Medicine*, (1988), vol. 319, No. 25, pp. 1676-1680.

Ross, et al., "Isolation and Characterization of a Carcinoma-Associated Antigen," *Biochemical and Biophysical Research Communications*, (1986), vol. 135, No. 1, pp. 297-303.

Saeterdal, et al., "Frameshift-mutation-derived peptides as tumor-specific antigens in inherited and spontaneous colorectal cancer," *PNAS*, (2001), vol. 98, No. 23, pp. 13255-13260.

Sato, et al., "A peptide mimetic of human interferon (IFN)-B," *Biochem Journal*, (2003), vol. 371, pp. 603-608.

Schelbenbogen, et al., "Identification of Known and Novel Immunogenic T-Cell Epitopes from Tumor Antigens Recognized by Peripheral Blood T-Cells From Patients Responding to IL-2-Based Treatment," *Int. J. Cancer*, (2002), vol. 98, pp. 409-414.

Schiller, et al., "A Direct Comparison, of Biological Response Modulation and Clinical Side Effects by Interferon-Beta, Interferon-Gamma, or the Combination of Interferons Beta and Gamma in Humans," *The Journal of Clinical Investigations*, (1990), vol. 85, pp. 1211-1221.

Schubert, et al., "Requirement of transcription factor NFAT in developing atrial myocardium," *The Journal of Cell Biology*, (2003), vol. 161, No. 5, pp. 861-874.

Schutze, et al., "Identification of expressed genes by laser-mediated manipulation of single cells," *Nature Biotechnology*, (1998), vol. 16, pp. 737-742.

Sendra, et al., "Three-dimensional crtystal structure of recombinant murine interferon-β," *The EMBO Journal*, (1992), vol. 11, No. 9, pp. 3193-3201.

Sensi, et al., "Cytotoxic T-lymphocyte clones from different patients display limited T-cell receptor variable-region gene usage in HLA-A2-restricted recognition of the melanoma antigen Melan-A/MART-1," *PNAS*, (1995), vol. 92, pp. 5674-5678.

Sgori, et al., "In Vivo Gene Expression Profile Analysis of Human Breast Cancer Progression," *Cancer Research*, (1999), vol. 39, pp. 5656-5661.

Shimizu, et al., "Induction of antigen specific cellular immunity by vaccination with peptides from MN/CA IX in renal cell carcinoma," *Oncology Reports*, (2003), vol. 10, 1307-1311.

Stevens, et al., "Generation of Tumor-Specific CTLs from Melanoma Patients by Using Peripheral Blood Stimulated with Allongeneic Melanoma Tumor Cell Lines," *The Journal of Immunology*, (1995), vol. 154, pp. 762-771.

Takeuchi, et al., "Nuclear Factor of Activated T Cells (NFAT) as a Molecular Target for 1α, 25-Dihydroxyvitamin D3-Mediated Effects," *The Journal of Immunology*, (1998), vol. 160, pp. 209-218.

Tamura, et al., "Identification of Cyclophilin B-derived Peptides Capable of Inducing Histocompatability Leukocyte Antigen-A2-restricted and Tumor-specific Cytotoxic T Lymphocytes," *Japan J. Cancer Research*, (Jul. 2001), vol. 92, pp. 762-767.

Tanaka, et al., "Mammaglobin-A is a tumor-associated antigen in human breast carcinoma," *Surgery*, (2003), vol. 133, pp. 74-80.

Thumer, et al., "Vaccination with Mage-3A1 Peptide-pulsed Mature, Monocyte-derived Dendritic Cells Expands Specific Cytotoxic T Cells and Induces Regression of Some Metastases in Advanced State IV Melanoma," *J. of Experimental Medicine*, (1999), vol. 190, No. 11, pp. 1669-1678.

Tso, et al., "Induction of G250-targeted and T-Cell mediated Antitumor Activity against Renal Cell Carcinoma Using a Chimeric Fusion Protein Consisting of G250 and Granulocyte/Monocyte-Colony Stimulating Factor," *Cancer Research*, (Nov. 2001), vol. 61, pp. 7925-7933.

Udono, et al., "Structural organization of the human microphthalmia-associated transcription factor gene containing four alternative promoters," *Biochimice et Biophysica Acta*, (2000), vol. 1491, pp. 205-219.

Ullenhag, et al., "Immunization of Colorectal Carcinoma Patients with a Recombinant Canarypox Virus Expressing the Tumor Antigen Ep-CAM/KSA (ALVAC-KSA) and Granulocyte Macrophage Colony-stimulating Factor Induced a Tumor-specific Cellular Immune Response," *Clinical Cancer Research*, (Jul. 2003), vol. 9, pp. 2447-2456.

van Rooij, et al., Requirement of Nuclear Factor of Activated T-cells in Calcineurin-mediated Cardiomyocyte Hypertrophy, *The Journal of Biochemical Chemistry*, (2002) vol. 277, No. 50, pp. 48617-48626.

Vega, et al., "Multiple Domains of MCIP1 Contribute to Inhibition of Calcineurin Activity," *The Journal of Biological Chemistry*, (2002), vol. 277, No. 33, pp. 30401-30407.

Wang, et al., "Morphine Negatively Regulates Interferon-γ Promoter Activity in Activated Murine T Cells through Two Distinct Cyclic AMP-dependent Pathways," *The Journal of Biological Chemistry*, (2003), vol. 278, No. 39, pp. 37622-37631.

Wang, et al., "Phase I Trail of a MART-1 Peptide Vaccine with Incomplete Freund's Adjuvant for Resected High-Risk Melanoma," *Clinical Cancer Research*, (Oct. 1999), vol. 5, pp. 2756-2765.

Yee, et al., "Adoptive T cell therapy using antigen-specific CD8+ T cell clones for the treatment of patients with metastatic melanoma: In vivo persistence, migration, and antitumor effect of transferred T cells," *PNAS*, (Dec. 10, 2002), vol. 99, No. 25, 16168-16173.

Yokoyama, et al., "Isolation and Expression of Rat Interferon β Gene and Growth-Inhibitory Effect of Its Expression on Rat Glioma Cells," *Biochemical and Biophysical Research Communications*, (1997), vol. 232. pp. 698-701, Article No. RC976359.

Zhai, et al., "Antigen-Specific Tumor Vaccines," *The Journal of Immunology*, (1996), vol. 156, pp. 700-710.

Zhou, et al., "Serological Cloning of PARIS-1: A New TBC Domain-Containing, Immunogenic Tumor Antigen from a Prostate Cancer Cell Line," *Biochemical and Biophysical Research Communications*, (2002), vol. 290. pp. 830-838.

\* cited by examiner

Figure 5
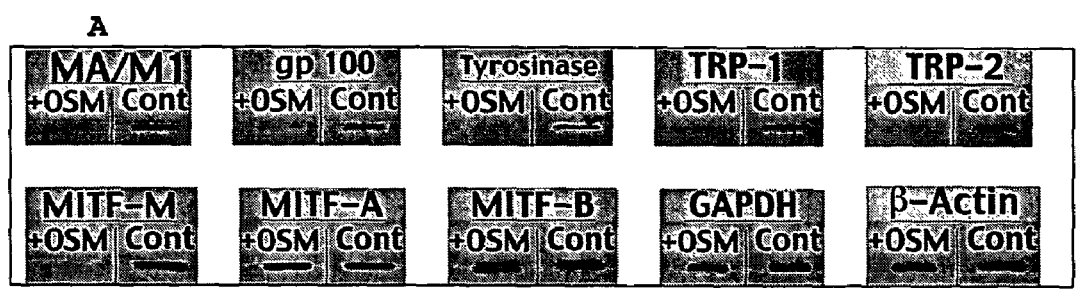
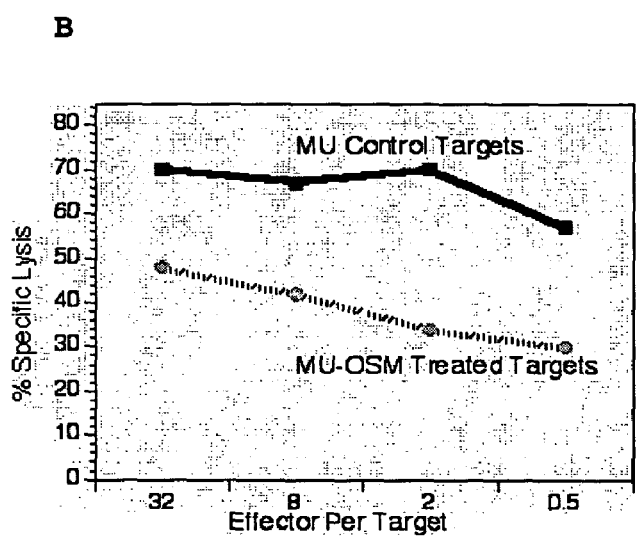

Figure 6
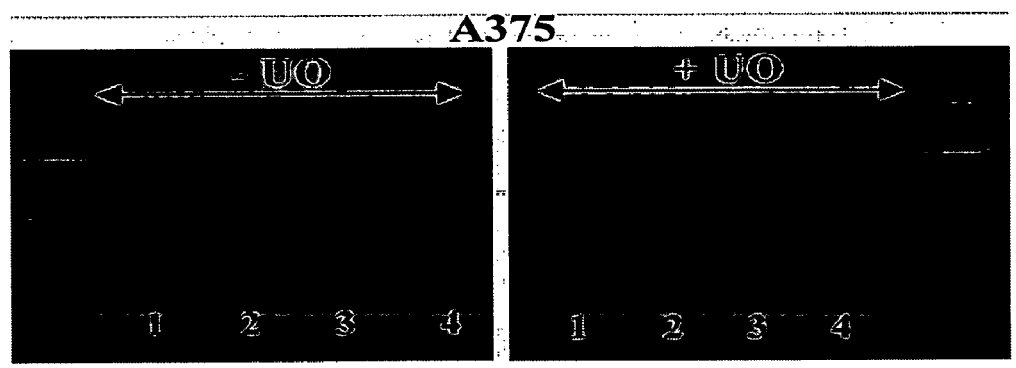
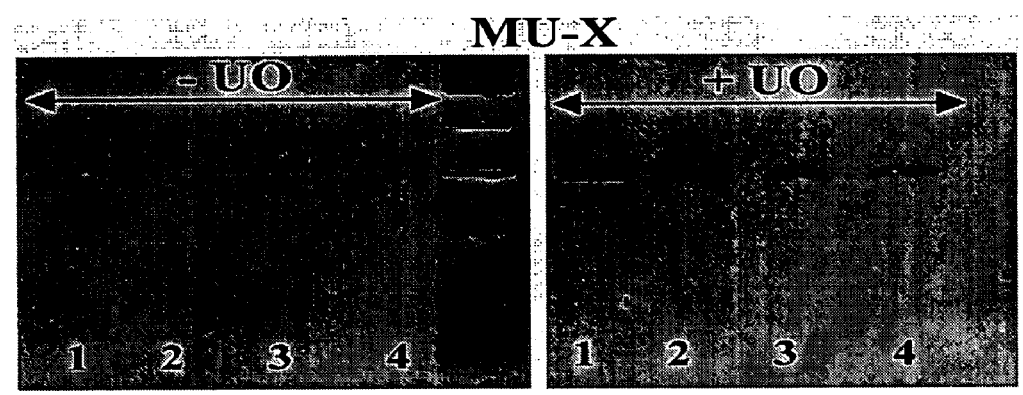

METHODS FOR UP-REGULATING ANTIGEN EXPRESSION IN TUMORS

RELATED APPLICATIONS

This application claims priority to U.S. Application Ser. No. 60/407,492, filed Aug. 29, 2002.

FIELD OF THE INVENTION

The invention relates to modulating tumor antigen associated (TAA) expression, and more particularly to methods of modulating TAA expression in order to treat a tumor.

BACKGROUND

Many solid tumors are presently known to involve the infiltration of autologous lymphocytes. These autologous lymphocytes, known as tumor-infiltrating lymphocytes (TIL), have been shown to recognize specific antigens expressed by cells of the solid tumor. Expression of such tumor-associated antigens (TAAs) in combination with appropriate accessory signals leads to a specific cytolytic (cytotoxic) reactivity of the TILs toward the solid tumors. In addition, antibodies that can recognize similar and unique antigens have also been shown to bind selectively to and facilitate killing of tumor cells.

Several tumor antigens have been identified in association with a variety of tumors (Boon, et al. (1994). Ann Rev Immunol, 12:337; Kawakami, et al. (1994). Proc Natl Acad Sci USA, 91:3515; and Bakker, et al. (1994). J Exp Med, 179: 1005). In addition to the identification of TAAs, immunodominant epitopes recognized by TILs have also been described for widely-expressed lineage-specific antigens, for example, the HLA-A2-restricted Melan-A/MART-1 in melanomas (Sensi, et al., (1995). Proc Natl Acad Sci USA, 92:5674; and Kawakami, et al., (1994). J Exp Med, 180:347).

Although there is mounting evidence that it is possible to induce cell mediated immunity against autologous melanomas, clinical immunotherapy strategies (Kradin, et al. Cancer Immunol. Immunother. (1987). 24:76); Kradin, et al. Lancet, (1989). 1:577; Rosenberg et al., (1987). N. Eng. J. Med., (1988). 25:1676; Dillman, et al. (1991). Cancer, 68:1; Gattoni, et al., (1966). Semin. Oncol, 23:754; and Kan-Mitchell, et al. (1993). Cancer Immunol. Immunother., 37:15), have failed to achieve routine efficacy. This failure has been due, at least in part, to the ability of tumors to evade immune destruction (Becker, et al., (1993). Int. Immunol., 5:1501; Jager, et al. (1997). Int. J. Cancer, 71:142; Macurer, et al., (1996). J. Clin. Invest., 98:1633; and Marincola, et al., (1996). J. Immunother. Emphasis Tumor Immunol., 9:192).

SUMMARY

The invention provides methods of increasing an immune response against a tumor cell. In one embodiment, a method includes administering to a subject with a tumor an amount of IFN-β receptor agonist and tumor associated antigen (TAA) sufficient to increase an immune response against the tumor cell. An immune response includes cell-mediated or humoral immune responses.

Also provided are methods of inhibiting silencing of a tumor associated antigen (TAA), and methods of increasing expression of a tumor associated antigen (TAA). In one embodiment, a method includes administering to a subject with a tumor an amount of IFN-β receptor agonist sufficient to inhibit silencing of the tumor associated antigen (TAA). In one aspect, the subject has been administered a tumor associated antigen (TAA) prior to, substantially contemporaneously with or following IFN-β receptor agonist administration. In another embodiment, a method includes contacting a cell capable of expressing a TAA with a compound that modulates an activity of an NFAT-motif binding protein in an amount sufficient to increase expression of a tumor associated antigen (TAA) of the cell.

Further provided are methods of treating a tumor. In one embodiment, a method includes administering to a subject with a tumor an amount of IFN-β receptor agonist and tumor associated antigen (TAA) sufficient to treat the tumor. In another embodiment, a method includes administering to a subject with a tumor an amount of IFN-β receptor agonist and an antibody or a cell that produces an antibody that specifically binds to a tumor associated antigen (TAA) sufficient to treat the tumor. In yet another embodiment, a method includes administering to a subject with a tumor an amount of IFN-β receptor agonist and an immune cell that interacts with a tumor cell sufficient to treat the tumor.

Additionally provided are methods of treating a subject having or at risk of having a tumor. In one embodiment, a method includes administering to the subject an amount of IFN-β receptor agonist and tumor associated antigen (TAA) sufficient to treat the subject. In another embodiment, a method includes administering to the subject an amount of IFN-β receptor agonist and an antibody or a cell that produces an antibody that specifically binds to a tumor associated antigen (TAA) sufficient to treat the subject. In yet another embodiment, a method includes administering to the subject an amount of IFN-β receptor agonist and an immune cell that interacts with a tumor cell sufficient to treat the subject.

Moreover provided are methods of increasing effectiveness of an anti-tumor therapy. In one embodiment, a method includes administering to a subject that is undergoing or has undergone tumor therapy, an amount of IFN-β receptor agonist and tumor associated antigen (TAA) sufficient to increase effectiveness of the anti-tumor therapy. In another embodiment, a method includes administering to a subject that is undergoing or has undergone tumor therapy, an amount of IFN-β receptor agonist and an antibody or a cell that produces an antibody that specifically binds to a tumor associated antigen (TAA) sufficient to increase effectiveness of the anti-tumor therapy. In yet another embodiment, a method includes administering to a subject that is undergoing or has undergone tumor therapy, an amount of IFN-β receptor agonist and an immune cell that interacts with a tumor cell sufficient to increase effectiveness of the anti-tumor therapy.

IFN-β receptor agonists useful in the invention include, for example, IFN-β, an IFN-β mimic, or an IFN-β receptor antibody. Compounds and agents useful in the invention also include molecules having similar activity as IFN-β (e.g., having TAA-inducing activity).

Compounds that modulate an activity of an NFAT-motif binding protein include calcium flux modulators (e.g., ionomycin and verapimil), VIVIT, gossypol, an N-substituted benzamide, rapamycin, a quinazoline-2,4-dione, 1-3, a pyrrolo[3,4-d]pyrimidine-2,4-dione, 4-8, 1alpha,25-dihydroxyvitamin D3, FK506, FK520, cyclosporin, 3,5-Bis(trifluoromethyl)pyrazoles, dithiocarbamates, Vasoactive intestinal peptide (VIP) and pituitary adenylate cyclase-activating polypeptide (PACAP), Carboxyamidotriazole, Morphine, a C32-O-arylethyl ether derivative of ascomycin, Ascomycin macrolactam derivative SDZ ASM 981, or MCIP1. Additonal compounds include, for example, an NFAT antisense nucleic acid, NFAT binding protein (e.g., an antibody) or a dominant negative NFAT polypeptide.

Tumors include any metastatic or non-metastatic, solid or liquid (e.g., hematopoetic), malignant or non-malignant neplasia or cancer in any stage, e.g., a stage I, II, III, IV or V tumor. Particular embodiments include a sarcoma, carcinoma, melanoma, myeloma, blastoma, lymphoma or leukemia.

Treatments provided include a therapeutic benefit, for example, reducing tumor volume, inhibiting an increase in tumor volume, stimulating tumor cell lysis or apoptosis, reducing tumor metastasis, or inhibiting tumor progression. Treatments provided also include reducing one or more adverse symptoms associated with the tumor, including reducing mortality or prolonging lifespan.

Treatments provided further include administering an antitumor therapy (e.g., surgical resection, radiotherapy, or chemotherapy), immune enhancing therapy (e.g., an antibody or a cell that produces an antibody that specifically binds to a tumor associated antigen (TAA); or an immune cell that interacts with a tumor cell) and an immune-enhancing agent. Cells that produce an antibody that specifically binds to a tumor associated antigen (TAA) include a plasma cell, B-cell, or a mammalian or non-mammalian cell transfected with a nucleic acid encoding the antibody. Immune cells that interact with a tumor cell include T cell, NK cell, LAK cell, monocyte or macrophage, including cells pre-selected to bind to an antigen expressed by the tumor.

Methods of identifying an agent that increases expression of a melanoma tumor associated antigen (TAA) are additionally provided. In one embodiment, a method includes contacting a cell capable of expressing a melanoma TAA (e.g., a melanoma cell) with a test agent; measuring the amount of TAA (e.g., Melan-A/MART-1, tyrosinase, gp100/pmel 17, TRP-1, TRP-2 or MITF-M) expressed in the presence of the test agent; and determining whether the amount of TAA expressed is greater in the presence than in the absence of the test agent. Increased TAA expression identifies the test agent as an agent that increases expression of a melanoma TAA.

TAAs modulated in accordance with the invention include, for example, antigens whose expression is increased in a tumor cell in comparison to a non-tumor cell (e.g., normal) counterpart; antigens whose expression is approximately the same or less in tumor cell in comparison to a non-tumor cell counterpart; and antigens whose expression changes during development, differentiation or in response to a stimulus. TAAs can be present on or in a cell (e.g., in the cytoplasm or nucleus or attached to the cell surface). TAAs can be present on any tumor, for example, a sarcoma, carcinoma, melanoma, myeloma, blastoma, lymphoma or a leukemia.

Exemplary TAAs include: Melan-A/MART-1, tyrosinase, gp100/pmel 17, TRP-1, TRP-2, an MITF, MITF-A, MITF-M, melanoma GP75, Annexin I, Annexin II, adenosine deaminase-binding protein (ADAbp), PGP 9.5, Colorectal associated antigen (CRC)—C017-1A/GA733, Ab2 BR3E4, CI17-1A/GA733, Hsp70, Hsp90, Hsp96, Hsp105, Hsp110, HSPPC-96, stress protein gp96 (a human colorectal cancer tumor rejection antigen, Heike 2000), gp96-associated cellular peptide, G250, Dipeptidyl peptidase IV (DPPIV), Mammaglobin, thyroglobulin, STn, Carcinoembryonic Antigen (CEA), Carcinoembryonic Antigen (CEA) epitope CAP-1, Carcinoembryonic Antigen (CEA) epitope CAP-2, etv6, aml1, Prostate Specific Antigen (PSA), PSA epitope PSA-1, PSA epitope PSA-2, PSA epitope PSA-3, Ad5-PSA, prostate-specific membrane antigen (PSMA), Prostatic Acid Phosphatase (PAP), Prostate epithelium-derived Ets transcription factor (PDEF), Parathyroid-hormone-related protein (PTH-rP), EGFR, PLU1, Oncofetal antigen-immature laminin receptor (OFA-iLR), MN/CA IX (CA9) (Shimizu, 2003), HP59, Cytochrome oxidase 1, sp100, msa, Ran GTPase activating protein, a Rab-GAP (Rab GTPase-activating) protein, PARIS-1, T-cell receptor/CD3-zeta chain, cTAGE-1, SCP-1, Glycolipid antigen-GM2, GD2 or GD3, GM3, FucosylGM1, Glycoprotein (mucin) antigens-Tn, Sialyl-Tn, TF and Mucin-1, CA125 (MUC-16), a MAGE family antigen, GAGE-1,2, BAGE, RAGE, LAGE-1, GnT-V, EP-CAM/KSA, CDK4, a MUC family antigen, HER2/neu, ErbB-2/neu, p21ras, RCAS1, α-fetoprotein, E-cadherin, α-catenin, β-catenin and β-catenin, NeuGcGM3, Fos related antigen, Cyclophilin B, RCAS1, S2, L10a, L10a, Telomerase rt peptide, cdc27, fodrin, p120ctn, PRAME, GA733/EoCam, NY-BR-1, NY-BR-2 NY-BR-3, NY-BR-4 NY-BR-5, NY-BR-6 NY-BR-7, NY-ESO-1, L19H1, MAZ, PINCH, PRAME, Prp1p/Zer1p, WT1, adenomatous polyposis coli protein (APC), PHF3, LAGE-1, SART3, SCP-1, SSX-1, SSX-2, SSX-4, TAG-72, TRAG-3, MBTAA, a Smad tumor antigen, lmp1, HPV-16 E7, c-erbB-2, EBV-encoded nuclear antigen (EBNA)-1, Herpes simplex thymidine kinase (HS-Vtk), alternatively spliced isoform of XAGE-1 (L552S), TGF beta RII frame shift mutation, BAX frame shift mutation, or an immunogenic fragment thereof.

BRIEF DESCRIPTION OF THE DRAWINGS

FIGS. 5A and 5B illustrate the effect of A) OSM on Melanoma Gene Expression in MU-89 cells. All shown at 0.39 ng RNA/sample except GADPH and β-Actin at 24.4 pg and TRP-1 at 15.6 ng; and B) OSM on Cytotoxic T Cell Recognition of Melan-A MART-1-expressing targets, MU.

FIG. 6 illustrates the effect of MITF-M transfection on endogenous expression of Melan-A/MART-1. Data shown for A375 and MU-X tumor cells transfected with MITF-M for 24 hours in the presence (10 μM) or absence of U0126 before PCR amplification of Melan-A/MART-1. Lane 1, MITF-M expression plasmid; 2, Empty vector control; 3, Transfection reagents only; 4, Untransfected control.

DESCRIPTION

Figure 1:
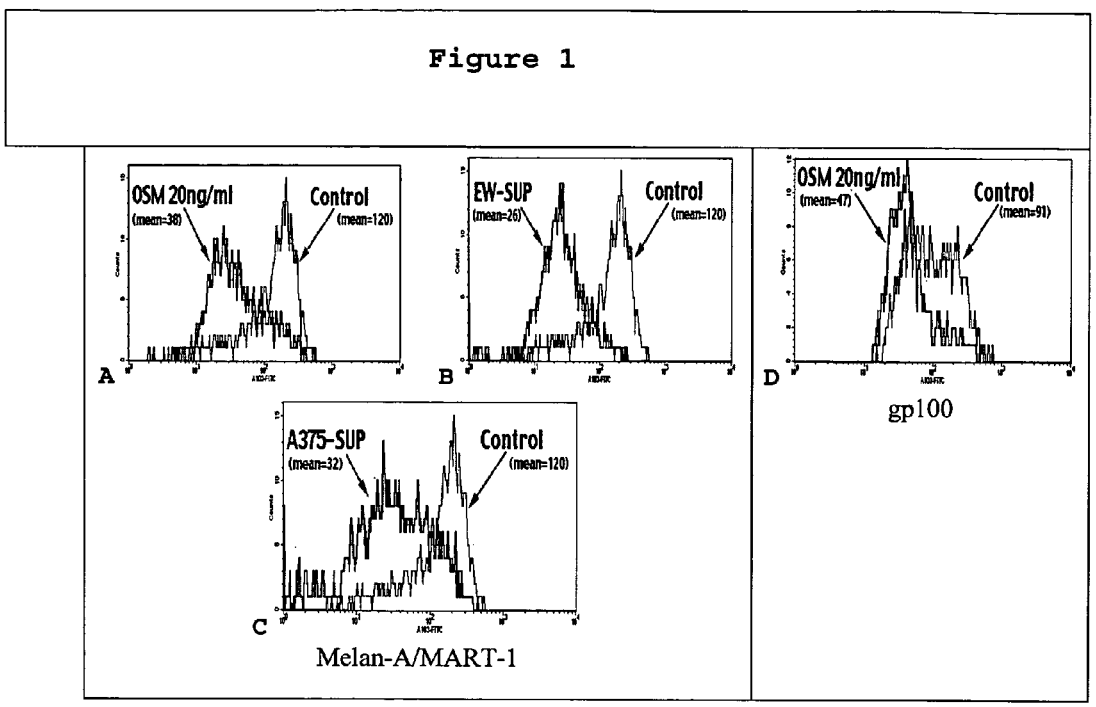
FIGS. 1A-1D illustrate data indicating the down-regulation of antigen expression in melanoma. MU tumor cells in A) control medium or D) control medium supplemented with human oncostatin M (OSM), or in B) supernatants from EW (containing EW produced OSM) or C) from A375 tumor cells (without OSM). Cells were stained for cytoplasmic expression of Melan-A/MART-1 protein (A-C) or gp100 (D) and assayed by flow cytometry. Mean channel of fluorescence is shown within each.

The invention is based at least in part on the finding that interferon-beta (IFN-β) increases expression of one or more tumor associated antigens (TAAs). Increasing expression of a tumor associated antigen of a cell, such as a tumor cell, increases recognition by the immune system. Thus, treating a tumor cell or tumor cell population with IFN-β, an IFN-β receptor agonist, or a compound or agent having a TAA-inducing activity as IFN-β, can increase antigenicity of tumor cells, thereby increasing recognition of tumor cells by T lymphocytes and antibodies. Consequently, the immune system is more likely to target the tumor cell(s) for destruction.

TAA expression on a cell can be increased with IFN-β, an IFN-β receptor agonist, or a compound or agent having similar activity as IFN-β (has TAA-inducing activity). IFN-β, an IFN-β receptor agonist, or a compound or agent having a TAA-inducing activity as IFN-β can be combined with one or more other compounds, agents, treatments or therapies having an anti-tumor effect. Thus, IFN-β, an IFN-β receptor agonist, or a compound or agent having a TAA-inducing activity as IFN-β can be used in combination with any other anti-tumor treatment or therapeutic protocol. For example, IFN-β, an IFN-β receptor agonist, or a compound or agent having a TAA-inducing activity as IFN-β can be combined with any treatment that increases an immune response against a tumor, thereby inhibiting tumor cell growth.

Thus, in accordance with the invention, methods of increasing an immune response against a tumor cell are provided. In one embodiment, a method includes administering to a subject having a tumor an amount of IFN-β receptor agonist and a tumor associated antigen (TAA) sufficient to increase an immune response against the tumor cell. In various aspects, an IFN-β receptor agonist comprises IFN-β, an IFN-β mimic (e.g., variant or modified form), or an IFN-β receptor antibody. In additional aspects, the immune response is cell-mediated or humoral. In further aspects, TAA is adminstered as full length or antigenic fragments, or with cells (e.g., cells that express TAA, such as tumor cells).

As used herein, "immune response" refers to a cell mediated or humoral (antibody mediated) response known in the art to be a function of the immune system. Stimulating, inducing or up-regulating an immune response means that either a cell mediated or humoral immune response is increased or triggered. For example, a melanoma TAA (e.g., an epitope of Melan-A/MART-1) can be administered and a CTL (cytotoxic T-lymphocyte) response to this antigen in a subject with metastatic melanoma elicited.

As used herein, an "IFN-β receptor agonist" means a molecule that binds to IFN-alpha/beta receptor (IFNAR), subunits IFNAR-1 or IFNAR-2, and which elicits a response typical of IFN-β. An exemplary response includes increasing TAA expression, i.e., a TAA inducing activity.

The invention also provides methods of increasing tumor associated antigen expression on a cell (e.g., a tumor cell). In one embodiment, a method includes administering to a subject having a tumor an amount of IFN-β receptor agonist and a tumor associated antigen (TAA) sufficient to increase tumor associated antigen expression on a tumor cell. In one aspect, an immune enhancing agent (e.g., lymphocytes or antibody or antibody expressing cells specific for TAA expressed by the tumor) is adminstered prior to, substantially contemporaneously with or following administration of IFN-β receptor agonist or a tumor associated antigen (TAA).

As used herein, the term "tumor associated antigen" or "TAA" refers to an antigen capable of expression by a tumor cell, or on cells of the same lineage as the tumor. The TAA in tumor may be expressed in amounts greater than normal relative to a non-tumor (normal) cell counterpart, or may be expressed at similar levels, or at levels less than normal cell counterparts, particularly if the gene encoding the TAA is down-modulated in the tumor cell.

Tumor associated antigens are antigenic molecules whose expression facilitates interaction of immune cells or immune molecules (e.g. antibodies) with tumor cells. TAAs are molecules or portions of the molecules that immune targeting molecules (i.e. receptors on immune cells and antibodies) bind. As discussed, TAAs may be present in or on normal cells; tumor TAA expression may but need not deviate from normal (non-tumor) counterpart cells (e.g., a normal cell not expressing TAA, expressing less of the TAA than a tumor cell, or expressing the same or more TAA than tumor.)

A tumor associated antigen can be expressed during an earlier developmental or different differentiation stage of the cell; after progressing through the developmental stage, expression of the TAA is typically altered. For example, a melanoma differentiation associated (mda) gene displaying enhanced or suppressed expression during growth inhibition and differentiation, such as MAGE and Melan-A/MART-1. As disclosed herein, TAA expression can also be induced or increased in response to a stimulus (e.g., IFN-β). In addition, kinase inhibitors can up-regulate TAA expression (Englaro et al. (1998). J Biol Chem 273:9966) of Melan-A/MART-1, gp100, tyrosinase, TRP-1 and TRP-2 on melanomas and TAA expression has been reported to up-regulated of by interferon-gamma (Gudagni et al. (1996). In Vivo 7:591). Tumor cell expression of one or more TAA's that are atypical for the cell is presumably due to aberrant gene regulation of the TAA.

Although not wishing to be bound by any theory, down-regulation of TAAs is thought to contribute to tumor cell escape from immune detection. Oncostatin M (OSM) (Durda et al. (2003). Mol Cancer Res 1:411) and IFN-γ (Le Poole et al (2002) Am J Pathol 160:521) can down-modulate Melan-A/MART-1 expression on melanoma cells.

Specific non-limiting examples of TAAs whose expression can be increased or induced in accordance with the invention include, for melanoma, tumor-associated testis-specific antigen (e.g., MAGE, BAGE, and GAGE), melanocyte differentiation antigen (e.g., tyrosinase, Melan-A/MART-1), a mutated or aberrantly expressed molecule (e.g., CDK4, MUM-1, beta-catenin), gp100/pmel 17, TRP-1, TRP-2, an MITF, MITF-A and MITF-M (King, et al. (1999). Am J Pathol 155:731). Additional specific examples of TAAs expressed by tumors include melanoma GP75, Annexin I, Annexin II, adenosine deaminase-binding protein (ADAbp), PGP 9.5 (Rode, et al. (1985). Histopathology 9:147), colorectal associated antigen (CRC)—C017-1A/GA733, Ab2 BR3E4, CI17-1A/GA733, Hsp70 (Chen, et al. (2002). Immunol Lett 84:81), Hsp90, Hsp96, Hsp105, Hsp110, HSPPC-96 (Caudill, M. M. and Z. Li (2001). Expert Opin Biol Ther 1:539), stress protein gp96 (a human colorectal cancer tumor rejection antigen, Heike et al. (2000). Int J Can 86:489), gp96-associated cellular peptides, G250, Dipeptidyl peptidase IV (DPPIV), Mammaglobin (Tanaka, et al. (2003). Surgery 133:74), thyroglobulin, STn (Morse, M. A. (2000). Curr Opin Mol Ther 2:453), Carcinoembryonic Antigen (CEA), Carcinoembryonic Antigen (CEA) epitope CAP-1, Carcinoembryonic Antigen (CEA) epitope CAP-2, etv6, aml1, Prostate Specific Antigen (PSA), PSA epitope PSA-1, PSA epitope PSA-2, PSA epitope PSA-3 (Correale, et al. (1998). J Immunol 161:3186) (Roehrbom, et al. (1996). Urology 47:59), Ad5-PSA, prostate-specific membrane antigen (PSMA), Prostatic Acid Phosphatase (PAP), Prostate epithelium-derived Ets transcription factor (PDEF), Parathyroid-hormone-related protein (PTH-rP), EGFR (P lunkett, et al. (2001). J Mammary Gland Biol Neoplasia 6:467), PLU1 (Plunkett, et al. (2001). J Mammary Gland Biol Neoplasia 6:467), Oncofetal antigen-immature laminin receptor (OFA-iLR), MN/CA IX (CA9) (Shimizu et al., (2003). Oncol. Rep. September-October; 10:1307), HP59, Cytochrome oxidase 1, sp100, msa (Devine, et al. (1991). Cancer Res 51:5826), Ran GTPase activating protein, a Rab-GAP (Rab GTPase-activating) protein, PARIS-1 (Zhou, et al. (2002). Biochem Biophys Res Commun 290:830), T-cell receptor/CD3-zeta chain, cTAGE-1, SCP-1, Glycolipid antigen-GM2, GD2 or GD3, GM3 (Bada, et al. (2002). Hum Exp Toxicol 21:263), FucosylGM1, Glycoprotein (mucin) antigens-Tn, Sialyl-Tn (Lundin, et al. (1999). Oncology 57:70), TF and Mucin-1 (Mukherjee, et al. (2003). J Immunother 26:47), CA125 (MUC-16) (Reinartz, et al. (2003). Cancer Res 63:3234), a MAGE family antigen, GAGE-1,2, BAGE, RAGE, LAGE-1 (Eichmuller, et al. (2003). Int J Cancer 104:482) (Chen, et al. (1998). Proc Natl Acad Sci USA 95:6919), GnT-V (Murata, et al. (2001). Dis Colon Rectum 44:A2-A4), MUM-1 (Kawakami, et al. (1996). Keio J Med 45:100), EP-CAM/KSA (Ullenhag, et al. (2003). Clin Cancer Res 9:2447), CDK4, a MUC family antigen, HER2/neu, ErbB-2/neu, p21ras, RCAS1, α-fetoprotein, E-cadherin, α-catenin, β-catenin and γ-catenin, NeuGcGM3 (Carr, et al. (2003). J Clin Oncol 21:1015), Fos related antigen (Luo, et al. (2003). Proc Natl Acad Sci USA 100:8850), Cyclophilin B (Tamura, et al. (2001). Jpn J Cancer Res 92:762), RCAS1, S2 (Koga, et al. (2003). Tissue Antigens 61:136), L10a (Koga, et al. (2003). supra), L10a, Telomerase rt peptide (Wang, et al. (2001). Oncogene 20:7699), cdc27, fodrin, p120ctn, PRAME, GA733/EoCam (Ross, et al. (1986). Biochem Biophys Res Commun 135:297), NY-BR-1, NY-BR-2 NY-BR-3, NY-BR-4 NY-BR-5, NY-BR-6 NY-BR-7 (Jager, et al. (2001). Cancer Res 61:2055), NY-ESO-1, L19H1, MAZ (Daheron, et al. (1998). Leukemia 12:326), PINCH (Greiner, et al (2000). Exp Hematol 28:1413), PRAME (Ikeda, et al. (1997). Immunity 6:199), Prp1p/Zer1p, WT1 (Oka, et al. (2002). Curr Cancer Drug Targets 2:45), adenomatous polyposis coli protein (APC), PHF3, LAGE-1, SART3 (Miyagi, et al. (2001). Clin Cancer Res 7:3950), SCP-1 (Jager, et al. (2002). Cancer Immun 2:5), SSX-1, SSX-2, SSX-4, TAG-72 (Buchsbaum, et al. (1999). Clin Cancer Res 5(10 Suppl): 3048s-3055s), TRAG-3 (Chen, et al. (2002). Lung Cancer 38:101), MBTAA (Basu, et al. (2003). Int J Cancer 105:377), a Smad tumor antigen, lmp-1, HPV-16 E7, c-erbB-2, EBV-encoded nuclear antigen (EBNA)-1, Herpes simplex thymidine kinase (HS-Vtk), alternatively spliced isoform of XAGE-1 (L552S; Wang, (2001). Oncogene 20:7699), TGF beta RII frame shift mutation (Saeterdal, et al. (2001). Proc Natl Acad Sci USA 98:13255), BAX frame shift mutation (Saeterdal, et al. (2001). Proc Natl Acad Sci USA 98:13255).

Immunogenic fragments (subsequences, including antigenic peptides that can be targeted) of TAAs are also included. In addition, variants and modified forms of TAA capable of eliciting, increasing or stimulating an immune response are also included.

TAAs can be delivered by a variety of methods. For example, when administering one or more TAAs with IFN-β, an IFN-β receptor agonist, or a compound or agent having a TAA-inducing activity as IFN-β, the TAA can be formulated to be presented to the immune system to stimulate an immune response towards the TAA. Thus, a TAA or antigenic fragment, or tumor or other cell having TAA can be adminstered in vivo. Tumor cells expressing TAA can optionally be treated ex vivo (e.g., with IFN-β, an IFN-β receptor agonist, or a compound or agent having similar activity as IFN-β) and transfused into a patient during therapy. Any agent that enhances antigen expression or antigenicity of the tumor can be used to treat the tumor in vivo or ex vivo. Tumor cell lysates or extracts, or irradiated or heat killed cells that renders them incapable of growth, but still able to induce an immune response, can also be administered.

TAAs can be delivered as peptides (Jäeger et al. (1996) *Int J Cancer* 66:162; Jäger et al. (2000) *Proc Natl Acad Sci USA* 97:12198; Marchand et al. (1999) *Int J Cancer*. 80:219, or as peptides in combination with adjuvants (Jäger et al. (1996). *Int J Cancer* 67:54; Rosenberg et al. (1998). *Nat Med* 4:321; Cormier et al. (1997). *Cancer J Sci Am*. 3:37; Wang et al. (1999). *Clin Cancer Res*. 5:2756).

TAAs can be delivered with other cells. For example, TAA peptides can be loaded into dendritic cells (Chen et al. (2001) Gene Ther 8:316; Fong et al. (2001). J Immunol 167:7150; Themer et al. (1999). J Exp Med 190:1669; Tso et al. (2001). Cancer Res 61:7925), or loaded into other antigen presenting cells (Pardoll (2002). Nature Rev Immunol 2:227).

Three types of DNA-based recombinant cancer vaccines have been used to deliver TAAs: DNA encoding TAAs can be used 1) to modify dendritic cells, 2) as 'naked' DNA-vaccine or 3) to construct recombinant viral vaccines. Recombinant vaccines and vaccine strategies have been developed to induce and potentiate T-cell responses of a host to TAAs. A particular example of such a strategy is recombinant poxvirus vectors in which the tumor-associated antigen (TAA) is inserted as a transgene. Recombinant vaccinia vaccines and recombinant avipox (replication-defective) vaccines have been employed to stimulate immune response towards the TAA; the use of diversified prime and boost strategies using different vaccines; and the insertion of multiple T-cell co-stimulatory molecules into recombinant poxvirus vectors, along with the TAA gene, to enhance T-cell immune response to the TAA and enhance or induce anti-tumor immunity.

The invention further provides methods of inhibiting silencing of a tumor associated antigen (TAA). In one embodiment, a method includes administering to a subject with a tumor an amount of IFN-β receptor agonist sufficient to inhibit silencing of the tumor associated antigen (TAA). In one aspect, the subject has been administered a tumor associated antigen (TAA) prior to, substantially contemporaneously with or following IFN-β receptor agonist administration.

As used herein, the term "silencing" refers to a down-regulation of TAA expression in tumor cells, a mechanism by which tumor cells reduce antigen expression to avoid immune detection and destruction. Thus, the terms "inhibiting silencing," "reversing silencing," "reducing silencing," and grammatical variations thereof, means that the down-regulation of TAAs observed in tumor cells is decreased or overcome. That is, "inhibiting silencing," means that TAA expression is increased or TAA expression is at least stabilized to the extent that little if any additional reduction in TAA expression occurs in a tumor cell.

One mechanism by which TAA silencing occurs is through suppression or inhibition of TAA gene expression at the transcriptional level, which may occur by what is referred to in the art as "gene silencing," or by a mechanism in which the gene promoter is inhibited (Kurnick et al. (2001) J Immunol 167: 1204; Durda et al. (2003) Mol Cancer Res 1:411). "Gene silencing" is believed to occur through chromatin remodeling or proteins that bind DNA and that directly or indirectly inhibit transcription of the gene. Promoter based inhibition can also occur by positive or negative influences on transcription factors required for gene transcription. An additional mechanism by which TAA silencing occurs is through increased TAA protein degradation or reduced TAA protein stability. The invention includes "inhibiting," "reversing" and "reducing" TAA silencing, regardless of the biological mechanism.

The invention additionally provides methods of treating a tumor. In one embodiment, a method includes administering to a subject with a tumor an amount of IFN-β receptor agonist and tumor associated antigen (TAA) sufficient to treat the tumor. In particular aspects, the treatment reduces tumor volume, inhibits an increase in tumor volume, stimulates tumor cell lysis or apoptosis, or reduces tumor metastasis. In another aspect, the subject is treated with or administered a further anti-tumor therapy (e.g., surgical resection, radiotherapy, immunotherapy or chemotherapy). In further aspects, the subject is administered an antibody or a cell that produces an antibody that specifically binds to a tumor associated antigen (TAA), an immune cell that interacts with a tumor cell, or an immune-enhancing agent.

The invention moreover provides methods of treating a subject having or at risk of having a tumor. In one embodiment, a method includes administering to a subject an amount of IFN-β receptor agonist and tumor associated antigen (TAA) sufficient to treat the subject. In one aspect, the subject is a candidate for, is undergoing, or has undergone anti-tumor therapy. In an additional aspect, the subject is administered an immune cell that interacts with a tumor cell.

Methods of increasing effectiveness of an anti-tumor therapy are also provided. In one embodiment, a method includes administering to a subject that is undergoing or has undergone tumor therapy, an amount of IFN-β receptor agonist and tumor associated antigen (TAA) sufficient to increase effectiveness of the anti-tumor therapy.

As used herein, the term "increase effectiveness," "promote effectiveness," or "improve effectiveness," when used in reference to a therapy, such as an anti-tumor therapy or treatment protocol in combination with IFN-β receptor agonist alone or in combination with tumor associated antigen (TAA), means that the overall therapy is improved relative to the therapy without IFN-β receptor agonist or tumor associated antigen (TAA) treatment. Thus, the detectable or measurable therapeutic benefit to a subject, as set forth herein, is greater with IFN-β receptor agonist or tumor associated antigen (TAA) treatment, than in the absence of IFN-β receptor agonist or tumor associated antigen (TAA) treatment.

Non-limiting examples of IFN-β receptor agonists include, for example, IFN-β (e.g., having the amino acid sequence of SEQ ID NO: 29). Mammalian IFN-β sequences such as human (Gray and Goeddel (1982). Nature, 298:859); rat (Yokoyama, et al., (1997). Biochem Biophys Res Commun., 232:698); canine (Iwata, et al., (1996). J Interferon Cytokine Res., 10:765); porcine (J Interferon Res., (1992). 12:153) are known in the art. Another example of IFN agonist is anti-IFN anti-idiotypic antibody (Osheroff et al. (1985). J Immunol, 135:306).

Non-limiting examples of IFN-β receptor antibodies include mammalian, human, humanized or primatized forms of heavy or light chain, $V_H$ and $V_L$, respectively, immunoglobulin (Ig) molecules. "Antibody" refers to any monoclonal or polyclonal immunoglobulin molecule, such as IgM, IgG, IgA, IgE, IgD, and any subclass thereof. The term "antibody" also includes functional fragment of immunoglobulins, such as Fab, Fab', (Fab')$_2$, Fv, Fd, scFv and sdFv, unless otherwise expressly stated.

The term "IFN-β receptor antibody" or "TAA antibody" means an antibody that specifically binds to IFN-β receptor and a TAA antibody, respectively. Specific binding is that which is selective for an epitope present in IFN-β receptor or a TAA. Selective binding can be distinguished from non-selective binding using assays known in the art (e.g., immunoprecipitation, ELISA, Western blotting).

The term "human" when used in reference to an antibody, means that the amino acid sequence of the antibody is fully human, i.e., human heavy and light chain variable and constant regions. All of the antibody amino acids are coded for in the human DNA antibody sequences or exist in a human antibody. An antibody that is non-human may be made fully human by substituting the non-human amino acid residues with amino acid residues that exist in a human antibody. Amino acid residues present in human antibodies, CDR region maps and human antibody consensus residues are known in the art (see, e.g., Kabat, *Sequences of Proteins of Immunological Interest*, 4$^{th}$ Ed. US Department of Health and Human Services. Public Health Service (1987); Chothia and Lesk (1987). J. Mol. Biol. 186:651; Padlan (1994). Mol. Immunol. 31:169; and Padlan (1991). Mol. Immunol. 28:489). Methods of producing human antibodies are known in the art (see, for example, WO 02/43478 and WO 02/092812).

The term "humanized" when used in reference to an antibody, means that the amino acid sequence of the antibody has non-human amino acid residues (e.g., mouse, rat, goat, rabbit, etc.) of one or more determining regions (CDRs) that specifically bind to the desired antigen in an acceptor human immunoglobulin molecule, and one or more human amino acid residues in the Fv framework region (FR), which are amino acid residues that flank the CDRs. Human framework region residues of the immunoglobulin can be replaced with corresponding non-human residues. Residues in the human framework regions can therefore be substituted with a corresponding residue from the non-human CDR donor antibody. A humanized antibody may include residues, which are found neither in the human antibody nor in the donor CDR or framework sequences. Methods of producing humanized antibodies are known in the art (see, for example, U.S. Pat. Nos. 5,225,539; 5,530,101, 5,565,332 and 5,585,089; Riechmann, et al., (1988). Nature 332:323; EP 239,400; WO91/09967; EP 592,106; EP 519,596; Padlan (1991). Molecular Immunol. 28:489; Studnicka et al., (1994). Protein Engineering 7:805; and Roguska. et al., (1994). Proc. Nat'l. Acad. Sci. USA 91:969).

Antibodies referred to as "primatized" in the art are within the meaning of "humanized" as used herein, except that the acceptor human immunoglobulin molecule and framework region amino acid residues may be any primate residue, in addition to any human residue.

The invention includes IFN-β peptides and mimetics, IFN-β receptor agonist peptides and mimetics, and modified (variant) forms, provided that the modified form retains, at least partial activity or function of unmodified or reference peptide or mimetic. For example, a modified IFN-β peptide or mimetic will retain at least a part of a TAA inducing activity. Modified (variant) peptides can have one or more amino acid residues substituted with another residue, added to the sequence or deleted from the sequence. Specific examples include one or more amino acid substitutions, additions or deletions (e.g., 1-3, 3-5, 5-10, 10-20, or more). A modified (variant) peptide can have a sequence with 50%, 60%, 70%, 75%, 80%, 85%, 90%, 95%, 96%, 97%, 98%, or more identity to a reference sequence (e.g., IFN-β). The crystal structure of recombinant interferon-beta (IFN-beta) can also be employed to predict the effect of IFN-β modifications (Senda, et al., (1992). EMBO J. 11:3193).

As used herein, the terms "mimetic" and "mimic" refer to a synthetic chemical compound which has substantially the same structural and/or functional characteristics as the reference molecule. The mimetic can be entirely composed of synthetic, non-natural amino acid analogues, or can be a chimeric molecule including one or more natural peptide amino acids and one or more non-natural amino acid analogs. The mimetic can also incorporate any number of natural amino acid conservative substitutions as long as such substitutions do not destroy activity. As with polypeptides which are conservative variants, routine testing can be used to determine whether a mimetic has detectable TAA inducing activity.

Peptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., induce or stabilize a secondary structure, e.g., a beta turn, gamma turn, beta sheet, alpha helix conformation, and the like. For example, a polypeptide can be characterized as a mimetic when one or more of the residues are joined by chemical means other than an amide bond. Individual peptidomimetic residues can be joined by amide bonds, non-natural and non-amide chemical bonds other chemical bonds or coupling means including, for example, glutaraldehyde, N-hydroxysuccinimide esters, bifunctional maleimides, N,N'-dicyclohexylcarbodiimide (DCC) or N,N'-diisopropylcarbodiimide (DIC). Linking groups alternative to the amide bond include, for example, ketomethylene (e.g., $-C(=O)-CH_2-$ for $-C(=O)-NH-$), aminomethylene ($CH_2-NH$), ethylene, olefin ($CH=CH$), ether ($CH_2-O$), thioether ($CH_2-S$), tetrazole ($CN_4-$), thiazole, retroamide, thioamide, or ester (see, e.g., Spatola (1983) in *Chemistry and Biochemistry of Amino Acids, Peptides and Proteins*, Vol. 7, pp 267-357, "Peptide and Backbone Modifications," Marcel Decker, N.Y.).

A "conservative substitution" is the replacement of one amino acid by a biologically, chemically or structurally similar residue. Biologically similar means that the substitution is compatible with biological activity, e.g., a TAA inducing activity. Structurally similar means that the amino acids have side chains with similar length, such as alanine, glycine and serine, or having similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

A specific example of an IFN-β variant is Betaseron (SEQ ID NO: 30), an analogue of human beta-interferon in which serine is substituted for cysteine at position 17. A specific example of a IFN-β mimetic is SYR6 (Sato and Sone, (2003). Biochem J., 371(Pt 2):603). Modified IFN-β sequence candidates for use in the invention are described, for example, in U.S. Pat. No. 6,514,729-recombinant interferon-beta muteins; U.S. Pat. No. 4,793,995-modified (1-56) beta interferons; U.S. Pat. No. 4,753,795-modified (80-113) beta interferons; and U.S. Pat. No. 4,738,845-modified (115-145) beta interferons.

Peptides and peptidomimetics can be produced and isolated using any method known in the art. Peptides can be synthesized, whole or in part, using chemical methods known in the art (see, e.g., Caruthers (1980). Nucleic Acids Res. Symp. Ser. 215; Horn (1980). Nucleic Acids Res. Symp. Ser. 225; and Banga, A. K., Therapeutic Peptides and Proteins, Formulation, Processing and Delivery Systems (1995) Technomic Publishing Co., Lancaster, Pa.). Peptide synthesis can be performed using various solid-phase techniques (see, e.g., Roberge (1995) Science 269:202; Merrifield (1997). Methods Enzymol. 289:3) and automated synthesis may be achieved, e.g., using the ABI 431A Peptide Synthesizer (Perkin Elmer) in accordance with the manufacturer's instructions.

Individual synthetic residues and polypeptides incorporating mimetics can be synthesized using a variety of procedures and methodologies known in the art (see, e.g., Organic Syntheses Collective Volumes, Gilman, et al. (Eds) John Wiley & Sons, Inc., NY). Peptides and peptide mimetics can also be synthesized using combinatorial methodologies. Techniques for generating peptide and peptidomimetic libraries are well known, and include, for example, multipin, tea bag, and split-couple-mix techniques (see, for example, al-Obeidi (1998). Mol. Biotechnol. 9:205; Hruby (1997). Curr. Opin. Chem. Biol. 1:114; Ostergaard (1997). Mol. Divers. 3:17; and Ostresh (1996). Methods Enzymol. 267:220). Modified peptides can be further produced by chemical modification methods (see, for example, Belousov (1997). Nucleic Acids Res. 25:3440; Frenkel (1995). Free Radic. Biol. Med. 19:373; and Blommers (1994). Biochemistry 33:7886).

Peptides can also be synthesized and expressed as fusion proteins with one or more additional domains linked thereto for producing a more immunogenic peptide, or to more readily isolate a recombinantly synthesized peptide. Domains facilitating isolation include, for example, metal chelating peptides such as polyhistidine tracts and histidine-tryptophan modules that allow purification on immobilized metals; protein A domains that allow purification on immobilized immunoglobulin; and the domain utilized in the FLAGS extension/affinity purification system (Immunex Corp, Seattle Wash.). The inclusion of a cleavable linker sequence such as Factor Xa or enterokinase (Invitrogen, San Diego Calif.) between a purification domain and the peptide can be used to facilitate peptide purification. For example, an expression vector can include a peptide-encoding nucleic acid sequence linked to six histidine residues followed by a thioredoxin and an enterokinase cleavage site (see e.g., Williams (1995). Biochemistry 34:1787; and Dobeli (1998). Protein Expr. Purif. 12:404). The histidine residues facilitate detection and purification of the fusion protein while the enterokinase cleavage site provides a means for purifying the peptide from the remainder of the fusion protein. Technology pertaining to vectors encoding fusion proteins and application of fusion proteins is known in the art (see e.g., Kroll (1993). DNA Cell. Biol., 12:441).

The invention includes any metastatic or non-metastatic tumor, cancer, malignancy or neoplasia of any cell or tissue origin. The tumor may be in any stage, e.g., a stage I, II, III, IV or V tumor, or in remission.

As used herein, the terms "tumor," "cancer," "malignancy," and "neoplasia" are used interchangeably and refer to a cell or population of cells whose growth, proliferation or survival is greater than growth, proliferation or survival of a normal counterpart cell, e.g. a cell proliferative or differentiative disorder. Such disorders can affect virtually any cell or tissue type, e.g., carcinoma, sarcoma, melanoma, neural, and reticuloendothelial or haematopoietic neoplastic disorders (e.g., myeloma, lymphoma or leukemia). A tumor can arise from a multitude of primary tumor types, including but not limited to breast, lung, thyroid, head and neck, brain, lymphoid, gastrointestinal (mouth, esophagus, stomach, small intestine, colon, rectum), genito-urinary tract (uterus, ovary, cervix, bladder, testicle, penis, prostate), kidney, pancreas, liver, bone, muscle, skin, and metastasize to other secondary sites.

Cells comprising a tumor may be aggregated in a cell mass or be dispersed. A "solid tumor" refers to neoplasia or metastasis that typically aggregates together and forms a mass. Specific examples include visceral tumors such as melanomas, breast, pancreatic, uterine and ovarian cancers, testicular cancer, including seminomas, gastric or colon cancer, hepatomas, adrenal, renal and bladder carcinomas, lung, head and neck cancers and brain tumors/cancers.

Carcinomas refer to malignancies of epithelial or endocrine tissue, and include respiratory system carcinomas, gastrointestinal system carcinomas, genitourinary system carcinomas, testicular carcinomas, breast carcinomas, prostatic carcinomas, endocrine system carcinomas, and melanomas. Melanoma refers to malignant tumors of melanocytes and other cells derived from pigment cell origin that may arise in the skin, the eye (including retina), or other regions of the body, including the cells derived from the neural crest that also gives rise to the melanocyte lineage. A pre-malignant form of melanoma, known as dysplastic nevus or dysplastic nevus syndrome, is associated with melanoma development.

Exemplary carcinomas include those forming from the uterine cervix, lung, prostate, breast, head and neck, colon, pancreas, testes, adrenal, kidney, esophagus, stomach, liver and ovary. The term also includes carcinosarcomas, e.g., which include malignant tumors composed of carcinomatous and sarcomatous tissues. Adenocarcinoma includes a carcinoma of a glandular tissue, or in which the tumor forms a gland like structure.

Sarcomas refer to malignant tumors of mesenchymal cell origin. Exemplary sarcomas include for example, lymphosarcoma, liposarcoma, osteosarcoma, chondrosarcoma, leiomyosarcoma, rhabdomyosarcoma and fibrosarcoma.

Neural neoplasias include glioma, glioblastoma, meningioma, neuroblastoma, retinoblastoma, astrocytoma, oligodendrocytoma A "liquid tumor" refers to neoplasia of the reticuloendothelial or haematopoetic system, such as a lymphoma, myeloma and leukemia, or neoplasia that is diffuse in nature, as they do not typically form a solid mass. Particular examples of leukemias include acute and chronic lymphoblastic, myeolblastic and multiple myeloma. Typically, such diseases arise from poorly differentiated acute leukemias, e.g., erythroblastic leukemia and acute megakaryoblastic leukemia. Specific myeloid disorders include, but are not limited to, acute promyeloid leukemia (APML), acute myelogenous leukemia (AML) and chronic myelogenous leukemia (CML); lymphoid malignancies include, but are not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Specific malignant lymphomas include, non-Hodgkin lymphoma and variants, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

As used herein, an "anti-tumor," "anti-cancer" or "anti-neoplastic" treatment, therapy, activity or effect means any compound, agent, therapy or treatment regimen or protocol that inhibits, decreases, retards, slows, reduces or prevents tumor, cancer or neoplastic growth, metastasis, proliferation or survival, in vitro or in vivo. Particular non-limiting examples of anti-tumor therapy include chemotherapy, immunotherapy, radiotherapy (ionizing or chemical), local thermal (hyperthermia) therapy and surgical resection. Any compound, agent, therapy or treatment regimen or protocol having an anti-cell proliferative activity or effect can be used in combination with an IFN-β receptor agonist, or a compound or agent having IFN-β activity in accordance with the invention.

Anti-proliferative or anti-tumor compounds, agents, therapies or treatments can operate by biological mechanisms that disrupt, interrupt, inhibit or delay cell cycle progression or cell proliferation; stimulate or enhance apoptosis or cell death, inhibit nucleic acid or protein synthesis or metabolism, inhibit cell division, or decrease, reduce or inhibit cell survival, or production or utilization of a necessary cell survival factor, growth factor or signaling pathway (extracellular or intracellular). Non-limiting examples of chemical agent classes having anti-cell proliferative and anti-tumor activities include alkylating agents, anti-metabolites, plant extracts, plant alkaloids, nitrosoureas, hormones, nucleoside and nucleotide analogues. Specific examples of drugs include cyclophosphamide, azathioprine, cyclosporin A, prednisolone, melphalan, chlorambucil, mechlorethamine, busulphan, methotrexate, 6-mercaptopurine, thioguanine, 5-fluorouracil, cytosine arabinoside, AZT, 5-azacytidine (5-AZC) and 5-azacytidine related compounds such as decitabine (5-aza-2'deoxycytidine), cytarabine, 1-beta-D-arabinofuranosyl-5-azacytosine and dihydro-5-azacytidine (Goffin et al. (2002). Ann Oncol. 13:1699; Gaubert (2000). Eur J Med Chem. 35:1011), bleomycin, actinomycin D, mithramycin, mitomycin C, carmustine, lomustine, semustine, streptozotocin, hydroxyurea, cisplatin, mitotane, procarbazine, dacarbazine, taxol, vinblastine, vincristine, doxorubicin and dibromomannitol.

Additional chemotherapeutic and biotherapeutic agents are known in the art and can be employed. For example, monoclonal antibodies that bind tumor cells or oncogene products, such as Rituxan® and Herceptin® (Trastuzumab) (anti-Her-2 neu antibody), Bevacizumab (Avastin®), Zevalin®, Bexxar®, Oncolym®, 17-1A (Edrecolomab), 3F8 (anti-neuroblastoma antibody), MDX-CTLA4, Campath®, Mylotarg®, IMC-C225 (Cetuximab), aurinstatin conjugates of cBR96 and cAC 10 (Doronina et al. (2003). Nat Biotechnol 21:778) can be used in combination with an IFN-β receptor agonist, or a compound or agent having IFN-β activity in accordance with the invention.

Compounds or agents having similar activity as IFN-β (a TAA-inducing activity) may or may not act through IFN-β receptor. For example, TAA regulatory regions are likely to include one or more genetic regulatory elements such that TAA expression is responsive to other inducers and suppressor molecules (i.e., other than IFN-β or IFN-β agonists). Thus, the invention may be practiced with compounds or agents that induce or suppress expression of a TAA via one or more genetic regulatory elements (i.e., any cis-acting nucleic acid element that can directly or indirectly alter expression of a TAA).

One example of such a molecule is nuclear factor of activated T-cells (also referred to as NFAT-motif binding protein, e.g., NFATc1, c2 c3 and c4), which is a family of transcription factors that participate in mediating signal transduction. Modulating (increasing or decreasing) an activity or function of an NFAT-motif binding protein is likely to modulate TAA expression. As used herein, the terms "activity" or "function" when used to modify "NFAT-motif binding protein," means that NFAT-motif binding protein is altered so as to alter TAA expression. For example, increased or decreased binding of an NFAT binding protein to a TAA regulatory region is one mechanism by which an NFAT-motif binding protein could regulate TAA expression.

Thus, the invention includes methods of modulating TAA expression, increasing an immune response against a tumor cell, increasing effectiveness of an anti-tumor therapy, treating a subject having or at risk of having a tumor, treating a tumor and inhibiting silencing of a tumor associated antigen (TAA), with an agent or compound that modulates an activity or function of an NFAT-motif binding protein. In respective embodiments, a method includes contacting a cell capable of expressing a TAA with a compound that modulates an activity of an NFAT-motif binding protein in an amount sufficient to increase expression of a tumor associated antigen (TAA) of the cell; increase an immune response against the tumor cell; increase effectiveness of the anti-tumor therapy; treat the subject, treat the tumor; and inhibit silencing of a tumor associated antigen (TAA).

Specific non-limiting examples of compounds that modulate an activity of an NFAT-motif binding protein include a calcium flux modulator (e.g., ionomycin or verapimil), VIVIT (Pu, et al. (2003). Circ Res 92:725), gossypol (Baumgrass, et al. (2001). J Biol Chem 276:47914), N-substituted benzamides (Lindgren, et al. (2001). Mol Immunol 38:267), rapamycin (Marx, et al. (1995). Circ Res 76:412), quinazoline-2,4-diones, 1-3, and pyrrolo[3,4-d]pyrimidine-2,4-diones, 4-8 (Michne, et al. (1995). J Med Chem 38:2557), 1alpha,25-dihydroxyvitamin D3 (Takeuchi, et al. (1998). J Immunol 160:209), FK506 (Rovira, et al. (2000). Curr Med Chem 7:673), FK520 (Marx, et al. (1995). Circ Res 76:412), cyclosporin (Rovira, et al. (2000). Curr Med Chem 7:673), 3,5-Bis(trifluoromethyl)pyrazoles (Djuric, et al. (2000). J Med Chem 43:2975), dithiocarbamates (Martinez-Martinez, et al. (1997). Mol Cell Biol 17:6437), Vasoactive intestinal peptide (VIP) and pituitary adenylate cyclase-activating polypeptide (PACAP) (Ganea and Delgado (2002). Crit Rev Oral Biol Med 13:229), carboxyamidotriazole (Faehling et al. (2002). Faseb J 16:1805), morphine (Wang, et al. (2003). J Biol Chem July 3 [Epub ahead of print]), C32-O-arylethyl ether derivatives of ascomycin (Armstrong, et al. (1999). Bioorg Med Chem Lett 9:2089), Ascomycin macrolactam derivative SDZ ASM 981 (Hultsch, et al. (1998). Arch Dermatol Res 290:501), and MCIP1 (Vega, et al. (2002). J Biol Chem 277:30401).

Additional examples of compounds that modulate an activity of an NFAT-motif binding protein include an NFAT antisense nucleic acid or RNAi, NFAT binding protein (e.g., an antibody; see, for example, Lyakh et al., Mol Cell Biol. (1997). 17:2475) or dominant negative NFAT polypeptide (see, for example, Schubert et al. (2003). J Cell Biol 161:861; van Rooij et al. (2002). J Biol Chem 277:48617).

Antisense can be designed based on NFAT nucleic acid sequences available in the database. Antisense includes single, double or triple stranded polynucleotides and peptide nucleic acids (PNAs) that bind RNA transcript or DNA. For example, a single stranded nucleic acid can target NFAT binding protein transcript (e.g., mRNA). Oligonucleotides derived from the transcription initiation site of the gene, e.g., between positions −10 and +10 from the start site, are a particular one example. Triplex forming antisense can bind to double strand DNA thereby inhibiting transcription of the gene. The use of double stranded RNA sequences (known as "RNAi") for inhibiting gene expression is known in the art (see, e.g., Kennerdell et al., (1998). Cell 95:1017; Fire et al., (1998). Nature, 391:806). Double stranded RNA sequences from an NFAT binding protein coding region may therefore be used to inhibit expression.

Compounds and agents having IFN-β activity (including IFN-β receptor agonists) may be more or less potent than IFN-β. Thus, a compound can have significantly less (e.g., 10% of the potency or activity) or more (e.g., 150-500%, or greater, potency or activity) of IFN-β.

Compounds or agents having IFN-β activity (e.g., increase or induce expression of a tumor associated antigen) may be used alone or in combination with IFN-β, IFN-β receptor agonist, or other compounds, agents, treatment or therapies having an anti-tumor effect or activity. For example, administering one or more TAA's expressed by a tumor in combination with the compound or agent having IFN-β activity can increase immune response towards a tumor that expresses or is induced to express the TAA, thereby increasing the effectiveness of the anti-tumor therapy.

In an invention method of administering one or more TAAs with IFN-β, an IFN-β receptor agonist, or a compound or agent having TAA-inducing activity as IFN-β, the two components need not be administered substantially contemporaneously with each other. In other words, a TAA may be administered to a subject within one or more hours (e.g., 1-3, 3-6, 6-12, 12-24, 24-48, 24-72 hours), days (e.g., 1-3, 3-5, 5-7, 7-10, 10-14 days, 14-30 days) or months (1-6) before or after IFN-β an IFN-β receptor agonist, or a compound or agent having TAA-inducing activity as IFN-β, administration. Accordingly, one or more TAAs can be administered prior to, substantially contemporaneous with or following administration of IFN-β, an IFN-β receptor agonist, or a compound or agent having similar activity as IFN-β in any order desired.

If a subject is first administered TAA (singly or multiple times), the subject may subsequently be administered IFN-β, an IFN-β receptor agonist, or a compound or agent having TAA-inducing activity as IFN-β, multiple times. Likewise, if a subject is first administered IFN-β, an IFN-β receptor agonist, or a compound or agent having TAA-inducing activity as IFN-β singly or multiple times, the subject may be subsequently administered TAA multiple times.

A subject may be first administered a TAA, and subsequently administered IFN-β, an IFN-β receptor agonist, or a compound or agent having TAA-inducing activity as IFN-β. Alternatively, a subject may be first administered IFN-β, an IFN-β receptor agonist, or a compound or agent having TAA-inducing activity as IFN-β, and subsequently administered a TAA. A subject may also be given multiple administrations of TAA and IFN-β, an IFN-β receptor agonist, or a compound or agent having TAA-inducing activity as IFN-β, in any sequence.

Any compound, agent, therapy or treatment having an immune-stimulating or enhancing activity or effect can be used in combination with an IFN-β receptor agonist, or a compound or agent having TAA-inducing activity as IFN-β, in accordance with the invention. As used herein, the term "immune enhancing," when used in reference to such a compound, agent, therapy or treatment, means that the compound provides an increase, stimulation, induction or promotion of an immune response, humoral or cell-mediated. Such therapies can enhance immune response generally, or enhance immune response to the specific tumor. Specific non-limiting examples of immune enhancing agents include monoclonal, polyclonal antibody and mixtures thereof (e.g., that specifically bind to a TAA).

Immune cells that interact with a tumor cell include lymphocytes, plasma cells, B-cells expressing antibody against TAA, NK cells, LAK cells and macrophages. Immune cells include cells that enhance or stimulate an immune response against TAA (e.g., dendritic cells or antigen presenting cells) are considered "immune enhancing". In addition, a mammalian or non-mammalian cell that expresses an antibody (e.g., plasma cell, B-cell or a mammalian or non-mammalian cell transfected with a nucleic acid encoding the antibody) that specifically binds to a TAA, can be used in accordance with the invention. An immune cell that targets a tumor cell can be used in accordance with the invention. For example, adoptive immunotherapy, in which tumor-infiltrating or peripheral blood lymphocytes can be infused into a tumor patient, following optional stimulation with a cytokine.

Immune stimulating molecules (Dredge et al. (2002) Cancer Immunol Immunother 51:521), such as Flt3 ligand (Disis et al. (2002) Blood 99:2845) and cytokines (e.g., cell growth, proliferation, chemotactic and survival factors) that enhance or stimulate immunogenicity of TAA are considered "immune enhancing," and can be administered prior to, substantially contemporaneously with or following administration of IFN-β receptor agonist, or a compound or agent having TAA-inducing activity as IFN-β (Nohria et al. (1994). Biotherapy 7:261; Pardoll (1995). Annu Rev Immunol 13:399; and Ahlers et al. (1997) J Immunol 158:3947). Specific non-limiting examples of cytokines include IL-2, IL-1α, IL-β, IL-3, IL-7, granulocyte-macrophage-colony stimulating factor (GMCSF), IFN-γ, IL-12, and TNF-β (Riker et al. (1999). Surgery 126:112; Scheibenbogen et al. (2002). Int J Cancer 98:409; Disis et al. (2002). Blood 99:2845; Schiller et al. (1990). J Clin Invest 86:1211; Chen et al. (2001). Gene Ther 8:316; Elzey et al. (2001). Int J Cancer 94:842). GMCSF stimulates antigen-presenting cells and exhibits anti-tumor activity, including against leukemia, melanoma, breast carcinoma, prostate carcinoma and renal cell carcinoma, can be used in accordance with the invention.

Molecules that that down-regulate the effects of TH1 immune response inhibitors are also considered as "immune enhancing." Specific non-limiting examples include antibodies to IL-10 or IL-10 receptor (Murray et al. (2003) Infect Dis 188:458), IL-4 and IL-5, thereby up-regulating the TH1 immune response Kinase inhibitors that enhance or stimulate TAA expression include Gleevec (STI571) and inhibitors of protein kinases (e.g. AKT inhibitor, H-89, PD98059, PD184352, U0126, HA1077, forskolin and Y27632). Such kinase inhibitors may synergize with other compounds (e.g., IFN-β) that stimulate, enhance or increase TAA expression.

"Gene silencing inhibitors" including DNA methyl transferase inhibitors such as 5-azacytosine and inhibitors of histone deacetylase such as trichostatin A are considered as "immune enhancing." IFN-β may also synergize with such inhibitors.

Adjuvants refer to a class of substances which when added to an antigen improve the immune response. Examples include compounds which promote uptake by accessory cells (e.g. macrophages and dendritic cells) which process antigen, such as alum (aluminum hydroxide), incomplete Freund's adjuvant, complete Freund's adjuvant, Ribi, Montanide ISA™ 51, GERBU vaccine adjuvant, CAP vaccine adjuvant, SLN (solid lipid nanoparticles), CpG DNA and RC529 adjuvant.

The invention therefore also provides methods of treating a tumor, methods of treating a subject having or at risk of having a tumor, and methods of increasing effectiveness of an anti-tumor therapy. In respective embodiments, a method includes administering to a subject with a tumor an amount of IFN-β receptor agonist and an antibody or a cell that produces an antibody that specifically binds to a tumor associated antigen (TAA) sufficient to treat the tumor; administering to the subject an amount of IFN-β receptor agonist and an antibody or a cell that produces an antibody that specifically binds to a tumor associated antigen (TAA) sufficient to treat the subject; and administering to a subject that is undergoing or has undergone tumor therapy, an amount of IFN-β receptor agonist and an antibody or a cell that produces an antibody that specifically binds to a tumor associated antigen (TAA) sufficient to increase effectiveness of the anti-tumor therapy. In various aspects, the cell producing an antibody that specifically binds to a tumor associated antigen (TAA) is selected from a plasma cell, B-cell, or a mammalian or non-mammalian cell transfected with a nucleic acid encoding the antibody.

The invention therefore further provides methods of treating a tumor, methods of treating a subject having or at risk of having a tumor, and methods of increasing effectiveness of an anti-tumor therapy. In respective embodiments, a method includes administering to a subject with a tumor an amount of IFN-β receptor agonist and an immune cell that interacts with a tumor cell sufficient to treat the tumor; administering to the subject an amount of IFN-β receptor agonist and an immune cell that interacts with a tumor cell sufficient to treat the subject; and administering to a subject that is undergoing or has undergone tumor therapy, an amount of IFN-β receptor agonist and an immune cell that interacts with a tumor cell sufficient to increase effectiveness of the anti-tumor therapy. In various aspects, the cell is selected from a T cell, NK cell, LAK cell, monocyte or macrophage. In an additional aspect, the cell has been pre-selected to bind to an antigen (e.g., a TAA) expressed by the tumor (e.g., T lymphocytes selected for strong avidity to TAA as presented on HLA molecules, Dudley et al. (2002). Science 298:850; Yee et al. (2002). PNAS 99:16168).

Methods of the invention include providing a detectable or measurable therapeutic benefit to a subject. A therapeutic benefit is any objective or subjective transient or temporary, or longer term improvement in the condition. Thus, a satisfactory clinical endpoint is achieved when there is an incremental improvement in the subjects condition or a partial reduction in the severity or duration of one or more associated adverse symptoms or complications or inhibition or reversal of one or more of the physiological, biochemical or cellular manifestations or characteristics of the disease. A therapeutic benefit or improvement ("ameliorate" is used synonymously) therefore need not be complete ablation of the tumor or any or all adverse symptoms or complications associated with the tumor. For example, inhibiting an increase in tumor cell mass (stabilization of a disease) can increase the subjects lifespan (reduce mortality) even if only for a few days, weeks or months, even though complete ablation of the tumor has not resulted.

Particular examples of therapeutic benefit or improvement include a reduction in tumor volume (size or cell mass), inhibiting an increase in tumor volume, a slowing or inhibition of tumor worsening or progression, stimulating tumor cell lysis or apoptosis, reducing or inhibiting tumor metastasis, reduced mortality, prolonging lifespan. Adverse symptoms and complications associated with tumor, neoplasia, and cancer that can be reduced or decreased include, for example, nausea, lack of appetite, and lethargy. Thus, a reduction in the severity or frequency of symptoms, an improvement in the subjects subjective feeling, such as increased energy, appetite, psychological well being, are examples of therapeutic benefit The doses or "sufficient amount" for treatment to achieve a therapeutic benefit or improvement are effective to ameliorate one, several or all adverse symptoms or complications of the condition, to a measurable extent, although reducing or inhibiting a progression or worsening of the condition or an adverse symptom, is a satisfactory outcome. The dose may be proportionally increased or reduced as indicated by the status of the disease being treated or the side effects of the treatment. Doses also considered sufficient are those that result in a reduction of the use of another therapeutic regimen or protocol. For example, an IFN-β receptor agonist and one or more TAAs is considered as having a therapeutic effect if administration results in less chemotherapeutic drug, radiation or immunotherapy being required for tumor treatment.

As is typical for treatment protocols, some subjects will exhibit greater or less response to treatment. Thus, appropriate amounts will depend upon the condition treated (e.g., the type or stage of the tumor), the therapeutic effect desired, as well as the individual subject (e.g., the bioavailability within the subject, gender, age, etc.).

Subjects appropriate for treatment include those having or at risk of having a tumor cell, those undergoing as well as those who are undergoing or have undergone anti-tumor therapy, including subjects where the tumor is in remission. The invention is therefore applicable to treating a subject who is at risk of a tumor or a complication associated with a tumor. Prophylactic methods are therefore included.

Subjects include those who have risk factors associated with tumor development. For example, subjects at risk for developing melanoma include fair skin, high numbers of naevi (dysplastic nevus), sun exposure (ultraviolet radiation), patient phenotype, family history, and history of a previous melanoma. Subjects at risk for developing cancer can be identified with genetic screens for tumor associated genes, gene deletions or gene mutations. Subjects at risk for developing breast cancer lack Brca1, for example. Subjects at risk for developing colon cancer have deleted or mutated tumor suppressor genes, such as adenomatous polyposis coli (APC), for example.

The term "subject" refers to animals, typically mammalian animals, such as a non human primate (apes, gibbons, chimpanzees, orangutans, macaques), a domestic animal (dogs and cats), a farm animal (horses, cows, goats, sheep, pigs), experimental animal (mouse, rat, rabbit, guinea pig) and humans. Subjects include animal disease models, for example, a rodent model for testing in vivo efficacy of IFN-β receptor agonist and one or more TAAs (e.g., a tumor animal model).

IFN-β receptor agonist, compounds and agents having a TAA-inducing activity as IFN-β can be administered in a conventional dosage form prepared by combining IFN-β receptor agonist, or a compound or agent having TAA-inducing activity as IFN-β with a conventional pharmaceutically acceptable carrier or diluent according to known techniques. The pharmaceutically acceptable carrier or diluent is dictated by the amount of active ingredient with which it is to be combined, the route of administration and other known variables.

Pharmaceutical compositions include "pharmaceutically acceptable" and "physiologically acceptable" carriers, diluents or excipients. As used herein, the term "pharmaceutically acceptable" and "physiologically acceptable," when referring to carriers, diluents or excipients includes solvents (aqueous or non-aqueous), detergents, solutions, emulsions, dispersion media, coatings, isotonic and absorption promoting or delaying agents, compatible with pharmaceutical administration and with the other components of the formulation. Such formulations can be contained in a tablet (coated or uncoated), capsule (hard or soft), microbead, emulsion, powder, granule, crystal, suspension, syrup or elixir.

Pharmaceutical compositions can be formulated to be compatible with a particular route of administration. Compositions for parenteral, intradermal, or subcutaneous administration can include a sterile diluent, such as water, saline solution, fixed oils, polyethylene glycols, glycerine, propylene glycol or other synthetic solvents. The preparation may contain one or more preservatives to prevent microorganism growth (e.g., antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose).

Pharmaceutical compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (e.g., glycerol, propylene glycol, and polyethylene glycol), and suitable mixtures thereof Fluidity can be maintained, for example, by the use of a coating such as lecithin, or by the use of surfactants. Antibacterial and antifungal agents include, for example, parabens, chlorobutanol, phenol, ascorbic acid and thimerosal. Including an agent that delays absorption, for example, aluminum monostearate and gelatin can prolonged absorption of injectable compositions.

For transmucosal or transdermal administration, penetrants appropriate to the barrier to be permeated are used in the formulation. Such penetrants are known in the art, and include, for example, for transmucosal administration, detergents, bile salts, and fusidic acid derivatives; for transdermal administration, ointments, salves, gels, or creams.

Additional pharmaceutical formulations and delivery systems are known in the art and are applicable in the methods of the invention (see, e.g., *Remington's Pharmaceutical Sciences* (1990) 18th ed., Mack Publishing Co., Easton, Pa.; *The Merck Index* (1996) 12th ed., Merck Publishing Group, Whitehouse, N.J.; *Pharmaceutical Principles of Solid Dosage Forms*, Technonic Publishing Co., Inc., Lancaster, Pa., (1993); and Poznansky, et al, *Drug Delivery Systems*, R. L. Juliano, ed., Oxford, N.Y. (1980), pp. 253-315)

Methods of identifying an agent that increases expression of a melanoma tumor associated antigen (TAA) are also provided. In one embodiment, a method includes contacting a cell capable of expressing a melanoma TAA with a test agent (e.g., a melanoma cell); measuring the amount of TAA expressed in the presence of the test agent; and determining whether the amount of TAA expressed is greater in the presence than in the absence of the test agent, wherein increased TAA expression identifies the test agent as an agent that increases expression of a melanoma TAA. In one aspect, the TAA is a differentiation antigen, e.g., Melan-A/MART-1, tyrosinase, gp100/pmel 17, TRP-1, TRP-2 or MITF-M, or an antigenic fragment thereof.

Kits that include one or more of IFN-β and IFN-β receptor agonist, or a compound or agent having a TAA-inducing activity as IFN-β packaged into suitable packaging material, are also provided. A kit typically includes a label or packaging insert including a description of the components or instructions for use in vitro, in vivo, or ex vivo, of the components therein. A kit can contain a collection of such components, e.g., IFN-β an IFN-β receptor agonist, or a compound or agent having a TAA-inducing activity as IFN-β, and one or more TAAs.

In one embodiment, a kit includes IFN-β, an IFN-β receptor agonist, or a compound or agent having a TAA-inducing activity as IFN-β, and instructions for treating (prophylaxis or therapeutic), a tumor of a subject. In another embodiment, the container includes one or more TAAs. In yet another embodiment, the kit or container includes an anti-tumor agent (e.g., a drug or antibody, such as an anti-TAA antibody).

The term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions.

Kits of the invention therefore can additionally include labels or instructions for using the kit components in a method of the invention. Instructions can include instructions for practicing any of the methods of the invention described herein including treatment methods. Thus, for example, a kit can include IFN-β and one or more TAAs, together with instructions for administering to a subject in a treatment method of the invention.

The instructions may be on "printed matter," e.g., on paper or cardboard within or affixed to the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described herein.

All publications, patents and other references cited herein are incorporated by reference in their entirety. In case of conflict, the specification, including definitions, controls.

As used herein, the singular forms "a", "and," and "the" include plural referents unless the context clearly indicates otherwise. Thus, for example, reference to an "IFN-beta agonist" includes a plurality of IFN-beta agonists and reference to "a tumor associated antigen" includes reference to one or more tumor associated antigens.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example I

This example describes exemplary materials, methods and procedures.

Cell Lines: All cell lines have been previously described. Melanoma tumor cells lines, MU, MU-X, EW, were established at the Massachusetts General Hospital (Ramirez-Montagut, et al. (2000). Clin. Exp. Immunol. 119:11). A375 was purchased from American Type Culture Collection, (Manassas, Va.). IGR-39D, 453A and 136.2 were provided by Dr. Peter Schrier, Leiden University, Leiden, The Netherlands. MM96L was provided by Dr. P. G. Parsons, Queensland Institute of Medical Research, Herston, Australia; (+) and (−) varieties (i.e. high and low expressors of Melan-A/MART-1 antigen) were derived by Dr. James Kurnick. The U937 myelomonocytic cell line was isolated by Dr. Kenneth Nilsson, Uppsala University, Uppsala, Sweden. U2-OS, a human osteosarcoma cell line as described by Nelissen (Nelissen et al. (2000). Exp Hematol 28:422.).

Reagents: Antibodies against Melan-A/MART-1 (clone A103) (Chen, et al. (1996) Proc Natl Acad Sci U S A 93:5915) were purchased from Vector Laboratories/NoivoCastra Laboratories (Burlingame, Cailf.). Anti-gp100 (clone HMB45) antibodies were obtained from Lab Vision Corp. (Fremont, Calif.). Recombinant human oncostatin M (rhOSM) was obtained from R&D Systems, (Minneapolis Minn.). Chemicals and other reagents were Analytical Grade and obtained from Sigma-Aldrich, (St. Louis, Mo.). Recombinant human beta-interferon-1a (Avonex®) and interferon-1b (Betaseron®) were products of Biogen (Cambridge, Mass.) and Berlex Laboratories Inc. (Montville, N.J.), respectively.

Conditioned Medium: Conditioned medium from Melan-A/MART-1 deficient melanoma tumor cell lines was generated by culturing cells at a starting concentration of $5 \times 10^5$ cells/ml in DMEM medium supplemented with between 1 and 10% FBS. Supernatants were collected after 72 hours by centrifugation of the cell cultures and filtration of the medium through a 0.2 micron filter (Millipore, Bedford, Mass.). Conditioned medium containing 1% FBS was concentrated between 10 and 20 fold by collecting the retentate from a nominal 30kD YM membrane (Centriprep, Millipore, Bedford, Mass.). In addition to tumor cell lines MU-X, EW and IGR39D, three non-melanoma cell lines were also used to generate conditioned medium under similar conditions. These human tumor cell lines were: Daudi (B cell lymphoma); Jurkat (T cell lymphoma; MCF-7 (breast carcinoma), which were obtained from the ATCC (American Type Culture Collection, Bethesda, Md.).

Determination of protein Antigen in Tumor Cells via Flow Cytometric Analysis: To evaluate expression of cytoplasmic Melan-A/MART-1 antigen in melanoma tumor cell lines, cells were first fixed for 10' in 1% paraformaldehyde; the cells are pelleted and incubated for 5' in 0.1% saponin prior to washing and addition of monoclonal antibody specific for Melan-A/MART-1, A-103 (Ramirez-Montagut, et al., supra) for 45' at 22° C. Following two washes, the cells were stained for 30' with FITC-conjugated goat-anti-mouse Ig antibody (DAKO, Carpenteria, Calif.) prior to fixation in 1% paraformaldehyde and analysis by flow cytometry (FACScan, Becton-Dickinson, Mt. View, Calif.). Histograms of fluorescence staining were generated for comparison of anti-Melan-A/MART-1 staining of various cell populations. Mean channel fluorescence was calculated using the "LYSIS" software provided by the manufacturer. Gp100 expression was determined similarly using the HMB45 monoclonal antibody.

Cytotoxicity Assays: TIL were assayed for the ability to lyse melanoma target cells in 4 hours via a $^{51}$Cr-release assay, as previously described (Ramirez-Montagut, et al., supra). The melanoma target cells with high constitutive expression of Melan-A/MART-1 were generated by low density culture (1-2×10$^5$/ml). These Melan-A/MART-1 expressing cells were compared with respect to their susceptibility to cytolysis to the same cells cultured for 3 to 6 days in the presence of conditioned medium from the Melan-A/MART-1 negative variant, MU-X, to derive target cells with low Melan-A/MART-1 expression. Low Melan-A/MART-1 expressing cells were further assayed after pulsing with Melan-A/MART-1 peptide amino acids 27-35 (AAGIGILTV; SEQ ID NO:1); (Zhai, et al. (1996). J Immunol. 156:700; Stevens, et al. (1995). J Immunol. 154:762; Rivoltini, et al. (1995). J Immunol. 154:2257; Kawakami, Y. and S. A. Rosenberg. (1997). Int Rev Immunol. 14:173, by culturing these target cells at 37° C. for 2 hours in 1 ml of medium containing 5 mg of peptide prior to labeling with $^{51}$Cr for use in cytolytic assays to demonstrate renewed susceptibility to specific T cell recognition.

In further instances, bulk and cloned TIL progeny were also assayed against autologous tumor (MU), allogeneic melanomas, as well as NK (K562), and LAK (Daudi), and EBV-transformed B lymphocyte targets: EBV-3 (HLA-A1, B8, DR3), EBV-19 (HLA-A2, B18, DR5), using the foregoing $^{51}$Cr-release assay. Pulsing included the following melanocyte lineage-derived peptides: Tyrosinase (Rivoltini, et al., supra): MLLAVLYCL (SEQ ID NO:2) or YMNGTMSQV (SEQ ID NO:3), MAGE-3 (Gaugler, et al. (1994). J Exp Med 179:921): EBDPIGHLY (SEQ ID NO:4). Clones were screened for cytotoxic activity at effector to target ratios of 50:1 and below.

PCR Analysis: Equal quantities of oligo-dT18 reverse-transcribed RNAs were subjected to RT-PCR analyses, as previously described (Kurnick, et al. (2001) J Immunol 167: 1204), using multiple dilutions to establish conditions where initial amounts of control mRNAs resulted in sub-saturating amounts of products, with representative template concentrations shown. Primers were designed from appropriate GenBank mRNA and genomic entries and designed to be intron-spanning to prevent simultaneous amplification of traces of genomic DNAs. Where this was not possible RNAs were treated with RNase-free DNase I and repurified.

Primer sequences: (Forward {sense}/reverse{anti-sense} pairs) (SEQ ID NOs:5-22)

```
Melan-A/MART-1:
CAAGATGCCAAGAGAAGATGCTCACT/GCTTGCATTTTTCCTACACC
ATTCCA;

β-Actin:
GAGATCACTGCCCTGGCACCCA/GCTCCAACCGACTGCTGTCACCTT
CAC;

gp100/Pmel17:
CTGATTGGTGCAAATGCCTCCTTCT/AGGAAGTGCTTGTTCCCTCCA
TCCA;

tyrosinase:
CAGCCCAGCATCATTCTTCTCCTCT/GCAGTGAGGACGGCCCCTACC
A;

TRP-1:
TGTTGCCCAGACCTGTCCCCT/GCAACATTTCCTGCATGTCTTTCTC
CA;
```

-continued

```
TRP-2:
CCTAGTGAACAAGGAGTGCTGCCC/CGCTGGAGATCTCTTTCCAGAC
ACAAC;

MITF-M:
TCTCTCACTGGATTGGTGCCACCT/CATGCCTGGGCACTCGCTCTCT

MITF-A:
CCAAGCCTCCGATAAGCTCCTCCA/CATGCCTGGGCACTCGCTCTCT

GAPDH:
TGAAGGTCGGAGTCAACGGATTTGGT/CTGCAAATGAGCCCCAGCCT
TCT
```

MITF-M and MITF-A share a common reverse primer owing to their shared mRNA 3' regions. PCR product identities were confirmed by automated sequencing.

Example II

This example describes expression data of melanocyte-associated antigens and transcription factors.

Melan-A/MART-1 deficient cells, such as MU-X and EW, produce soluble factors that down-modulate antigen expression in otherwise constitutively positive cells (Kurnick, et al., supra); Ramirez-Montagut, et al., supra). To determine the natural repertoire of gene expression of related proteins in a series of antigen-positive and deficient cell lines, four Melan-A/MART-1-expressing melanoma cell lines, 136.2, 453A, MM96L (an antigen-expressing variant, designated MM96L+, and an Melan-A/MART-1 deficient variant designated MM96L–) and MU (an antigen-expressing variant, designated MU, and an Melan-A/MART-1 deficient variant designated MU-X), and an additional five cell lines that have weak or deficient Melan-A/MART-1 expression, MU-X, EW, IGR-39D, MM976L– and A375, as well as the Burkitt lymphoma-derived RAMOS cell line, were studied (Table 1). Antigen expression of Melan-A/MART-1 (MA/M1), gp100 and tyrosinase was assessed by cytoplasmic staining with appropriate monoclonal antibodies. In addition, assessment of gross differences in the relative mRNA steady-state levels for these markers between different cell lines was made following PCR amplification.

As shown in Table 1A, below, low expression of Melan-A/MART-1 is generally associated with low gp100 and tyrosinase expression. Among the melanomas, only EW secretes measurable amounts of protein (as determined in ELISA), but an additional 5 cell lines show detectable OSM mRNA levels, albeit weaker than EW (and non-melanoma RAMOS). Only MM96 and A375 appear to be deficient for OSM mRNA. Tyrosinase related proteins TRP-1 and TRP-2 parallel the expression of the other melanocyte markers.

A series of transcription factors related to melanocyte differentiation were also examined. As shown in Table 1B, the melanocyte-associated allele of MITF, namely MITF-M, was expressed strongly on the Melan-A/MART-1 expressing tumors, but not on the antigen deficient cell lines, except for A375. In contrast, the MITF-A isoform was expressed on all but the RAMOS cell line. Sox 10 showed a pattern similar to MITF-M, although it was detectable in MU-X as well as A375. Pax 3, brn2 and tbx2 were widely expressed among all of the melanomas, although tbx2 was only weakly expressed in EW.

TABLE 1

Antigen and Transcription Factor mRNA Levels in Melanoma Cell Lines.
The (++++) designation indicates easily detectable (relatively high level) product formation.
Where the designation of +/− is assigned, product levels were reproducibly low, often
requiring a second round of nested PCR for unequivocal detection. (Comparison of the relative
levels between separate markers is not feasible with these assays).

1A. Melanocyte Lineage Antigen Expression (Protein and mRNA)

| TUMOR | 136.2 | 453A | MM96L | MU-89 | MU-X | EW | IGR-39D | A375 | RAMOS |
|---|---|---|---|---|---|---|---|---|---|
| OSM | ++ | + | − | ++ | +/− | ++++ | ++ | − | ++++ |
| MA/M1 | ++++ | ++++ | ++++ | ++++ | +/− | +/− | +/− | +/−* | − |
| gp100 | ++++ | ++++ | ++++ | ++++ | + | + | + | + | − |
| tyrosinase | ++++ | ++++ | ++++ | ++++ | − | − | +/− | +/− | − |
| TRP-1 | ++++ | ++++ | ++++ | +++ | ++ | − | ++ | ++ | − |
| TRP-2 | +++ | ++++ | ++++ | ++ | +/− | − | − | ++ | − |

*A375 have detectable mRNA for Melan-A/MART-1, but are relatively deficient in cytoplasmic protein expression.

1B. Transcription Factor Expression (mRNA)

| TUMOR | 136.2 | 453A | MM96L | MU-89 | MU-X | EW | IGR-39D | A375 | RAMOS |
|---|---|---|---|---|---|---|---|---|---|
| MITF-M | ++++ | ++++ | ++++ | ++++ | +/− | +/− | +/− | ++ | − |
| MITF-A | ++++ | ++++ | ++++ | ++++ | ++++ | ++++ | ++++ | ++++ | − |
| BRN2 | ++++ | ++++ | ++++ | ++++ | ++++ | ++++ | ++++ | ++++ | − |
| STAT3 | ++++ | ++++ | ++++ | ++++ | ++++ | ++++ | ++++ | ++++ | ++++ |
| Pax3 | ++++ | ++++ | ++++ | ++++ | ++++ | ++++ | ++++ | ++++ | + |
| SOX 10 | ++++ | ++++ | ++++ | ++++ | + | − | +/− | ++++ | − |
| Tbx2 | ++++ | ++++ | ++++ | ++++ | +++ | + | +++ | ++++ | − |

Example III

This example describes down-regulation of melanocyte-associated antigens Melan-A/MART-1 and gp100. This example also describes data indicating that IFN-beta up-regulates melanocyte-associated antigens Melan-A/MART-1 and gp100.

Expression of Melan-A/MART-1 can be down-regulated by culture with supernatants from Melan-A/MART-1-negative tumors such as EW and A375 (Ramirez-Montagut, et al., supra). In brief, MU tumor cells were cultured for 3 days in control medium or in 20 ng/ml of OSM (FIGS. 1A and 1D), or in supernatants from EW (contains OSM) (FIG. 1B) or A375 tumor cells (does not contain OSM) (FIG. 1C). Cells were stained for cytoplasmic expression of Melan-A/MART-1 protein (FIGS. 1A-1C) or gp100 (FIG. 1D) and assayed by flow cytometry.

The data indicate that Melanoma Antigen Silencing Activity (MASA) produced by EW cells includes OSM and at least one additional soluble factor, designated MASA2, that is present in EW supernatants following removal of OSM, and is also present in A375 cells that do not produce OSM.

The loss of Melan-A/MART-1 is associated with a marked diminution in the ability of T cells to lyse tumor cells which have been treated with MASA-containing supernatants (Ramirez-Montagut, et al., supra). The loss of T cell-mediated lysis can be overcome by the addition of the Melan-A/MART-1-derived peptide, AAGIGILTV (SEQ ID NO:1), which restores cytolytic susceptibility. Loss of Melan-A/MART-1 is generally accompanied by diminished gp100 and tyrosinase, as well as other melanocyte lineage proteins, indicating that there is a "global" change in the tumor cells. However, the down-modulation of antigen expression appears to be somewhat selective as the HLA Class I antigen needed for presentation of the melanoma peptide is not down-modulated (Kurnick, et al., supra). When MASA-containing conditioned medium was removed from the Melan-A/MART-1 expressing tumor cells, there was renewed expression of this antigen. These antigen positive cells are again lysed by Melan-A/MART-1-specific cytotoxic T cells.

Oncostatin M and other melanoma cell line derived factors can down modulate melanocyte lineage antigen expression in various melanoma cell lines (Kurnick, et al., supra). A number of cytokines for up and down-modulating activity of melanocyte lineage antigens were evaluated.

Figure 2:
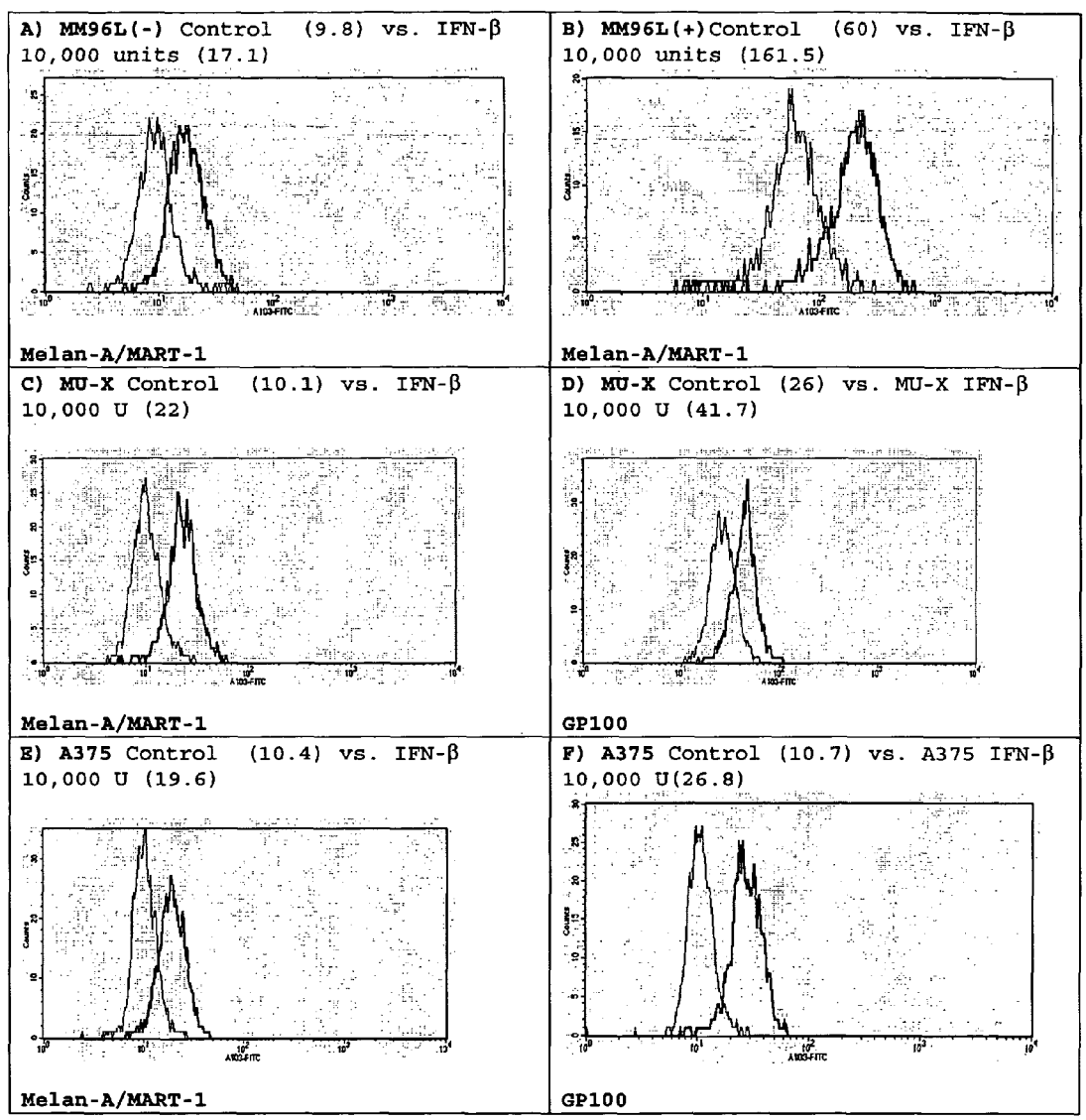
FIGS. 2A-2I illustrate data indicating that interferon-beta (IFN-β) increases expression of melanocyte lineage antigens (Melan-A/MART-1 and GP100) in melanoma cell lines 453A, A375, MU-X, MU-89, MM96L(−), and MM96L(+). Numbers in parentheses indicate the mean channel number. In each set, the curve to the right (stronger fluorescence) indicates increased expression following IFN-β treatment.
Figure 2:
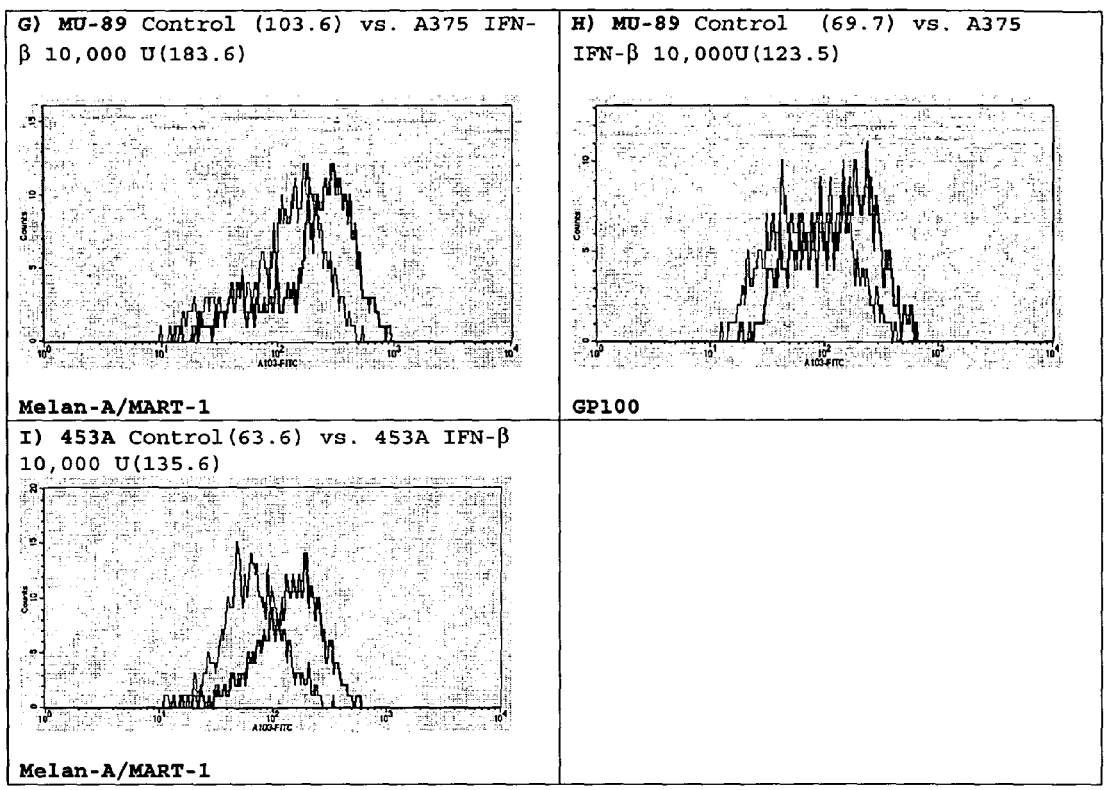
Figure 3:
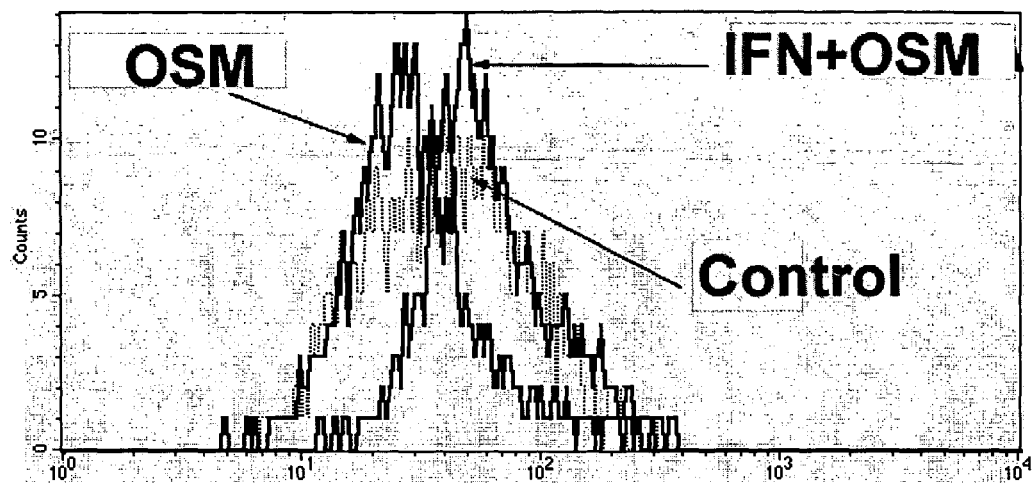
FIG. 3 illustrates data indicating that interferon-beta overcomes down-regulation of gp100 antigen by OSM. Control MU-89 (41.6) vs. MU-89 plus OSM (29.5) vs MU-89 plus IFN-beta+OSM (63.3).
Figure 4:
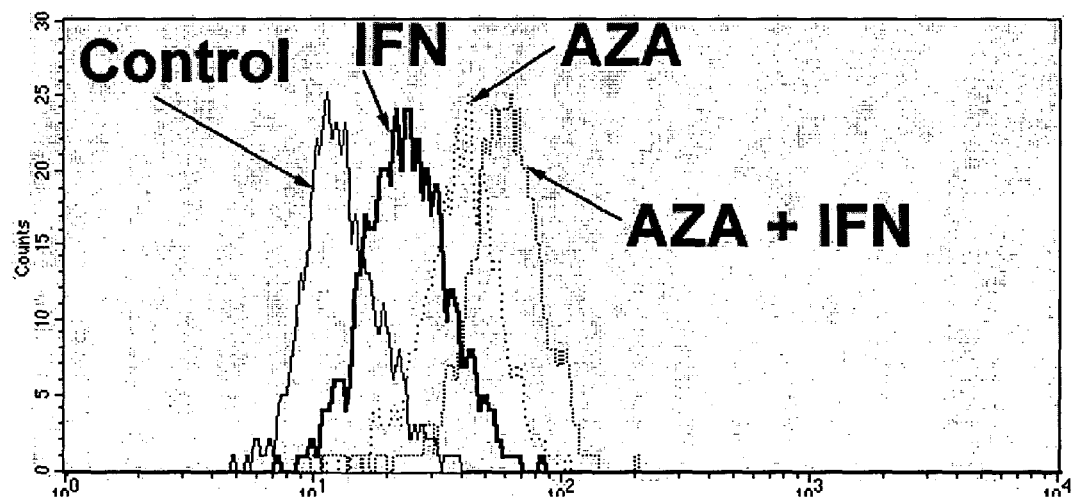
FIG. 4 illustrates data indicating that interferon-beta with 5-azacytidine (AZA) or trichostatin induces high levels of antigen expression in constitutive low antigen-expressing cells, MU-X. MU-X Control (12.8) vs. MU-X+Interferon-Beta 5,000 IU/mL (23.2) vs. MU-X+5-AZA 40uM (39.0) vs. AZA 40uM+Interferon-Beta 5,000 IU/mL (57.3)

Surprisingly, interferon-beta had up-modulating activity on all melanoma cell lines, both low and high expressors of Melan-A/MART-1 (FIG. 2). Furthermore, interferon-beta could reverse the down modulating effect of Oncostatin M on gp100 (FIG. 3—HMB 45 staining), and the effect of interferon-beta was augmented by treating the cells with a DNA methylase inhibitor such as 5 azadeoxycytidine (FIG. 4—gp100 (HMB) staining).

In sum, the foregoing data indicate that interferon-beta can inhibit the antigen down-modulating effect of Oncostatin-M, a known cytokine capable of mediating antigen-silencing in the melanoma system, as well as down-modulation induced by an additional molecule or molecules produced by melanoma cells (MASA) that manifest antigen silencing. Interferon-beta can up-regulate Melan-A MART-1 antigen expression on all melanoma cell lines studied to date regardless of the mechanism controlling antigen expression down-modulation.

IFN-β also enhances expression of MHC class I antigens (HLA-A, B and C), and IFN-γ enhances both class I and class II MHC antigens, thus increasing production of antigen-presenting molecules on tumor cells. Expression of new TAA and new HLA is therefore a doubly-effective treatment for enhancing T cell recognition of tumor cells, making it more likely that a cytotoxic T lymphocyte (CTL) will bind and kill tumor cells treated with IFN-β.

Example IV

This example describes down-regulation of melanocyte-associated antigens MITF, tyrosinase, TRP-1 and TRP-2. This example also describes data indicating that transfection of MITF-M up-regulated Melan-A/MART-1 antigen expression.

Tumors with low or absent Melan-A/MART-1 are also relatively deficient in tyrosinase and gp100; 3 of 4 low-Melan-A MART-1 melanomas have low MITF-M, including the MU-X line derived from Melan-A/MART-1+MU cells. The sox10 regulator of MITF-M expression is deficient in 2 of 4 of the low-Melan-A/MART-1 melanomas, while another melanocyte-lineage transcription factor, tbx2, was deficient at the mRNA level only in the Melan-A/MART-1-low EW cell line (Table 1).

OSM induces down-modulation of various melanocyte-related genes, including Melan-A/MART-1, tyrosinase, gp100, TRP-1 and TRP-2 (FIG. 5). While OSM also down-modulates MITF-M expression, the MITF-A isoform is not detectably responsive to OSM. Expression of the microphthalmia gene variants is dependent on different promoters and with different N-termini in their respective translated proteins (Udono, et al. (2000). Biochim Biophys Acta 1491:205). The differential action can provide clues to the promoter elements responsive to OSM; for example, only the MITF-M isoform promoter has a perfect CRE site.

All four of the Melan-A/MART-1 deficient melanoma cell lines studied produce strong antigen-silencing activity. This suggests a correlation between antigen expression and the production of an antigen-silencing factor. Melanocytes, which normally express this antigen, must be down-regulated in order to shut off transcription of this protein. If a tumor mutant had lost the Melan-A/MART-1 gene, or its promoter, there would be no selective advantage for the cell to continue to produce an "antigen-silencing" factor. The simultaneous loss of tyrosinase and gp100 suggest that any mutations in these cells would be targeting some gene regulatory molecules, as it would be less likely that all of these chromosomally distinct genes would be deleted or mutated simultaneously in several different tumor lines. Whether such a gene is involved in differentiation of the melanocyte lineage, or perhaps maintenance of a less mature phenotype, active production of MASA seems to be characteristic of antigen-negative melanomas.

To express MITF-M in cell lines expressing low levels of Melan-A/MART-1, MITF-M coding sequence was amplified from MITF-M-positive cells and cloned in an SV40-promoter expression vector (pSV21ink); translation of the MITF-M insert uses optimal Kozak initiation signals (Kozak (1999). Gene 234:187). Constructs were transfected into low-Melan-A/MART-1 expressor melanoma (MU-X and A375). In all studies controls comprised empty vector, transfection reagents in the absence of added DNA, and corresponding untransfected cells. Data shown in FIG. 6 for A375 and MU-X tumor cells transfected with MITF-M for 24 hours in the presence (10 µM) or absence of U0126 before PCR amplification of Melan-A/MART-1.

MUX and A375 cell lines exhibited up-regulation of endogenous Melan-A/MART-1 after transfection with the MITF-M expression construct (FIG. 6). A MEK inhibitor (U0126) was then added to determine whether it could synergize with ectopically introduced MITF-M. In this regard, plasmid-encoded MITF-M gene is not subject to the normal MITF-M transcriptional controls, since U0126 down-modulates native MITF-M message.

U0126 addition augmented enhancement of Melan-A/MART-1 expression in both MITF-M transfected A375 and MU-X tumor cell lines. These results indicate that controlling MITF-M expression would also control Melan-A/MART-1 expression.

Example V

This example describes data indicating that IFN-β up-regulation of melanocyte-associated antigen expression increases T cell killing of melanoma cells.

In brief, A375 cells were treated with 100,000 units of IFN-β for three days. The cells were subsequently labeled with $^{51}Cr$ and tested as targets in a cytotoxicity assay using bulk anti-melanoma T lymphocytes as the effector cells (Example I).

Figure 7:
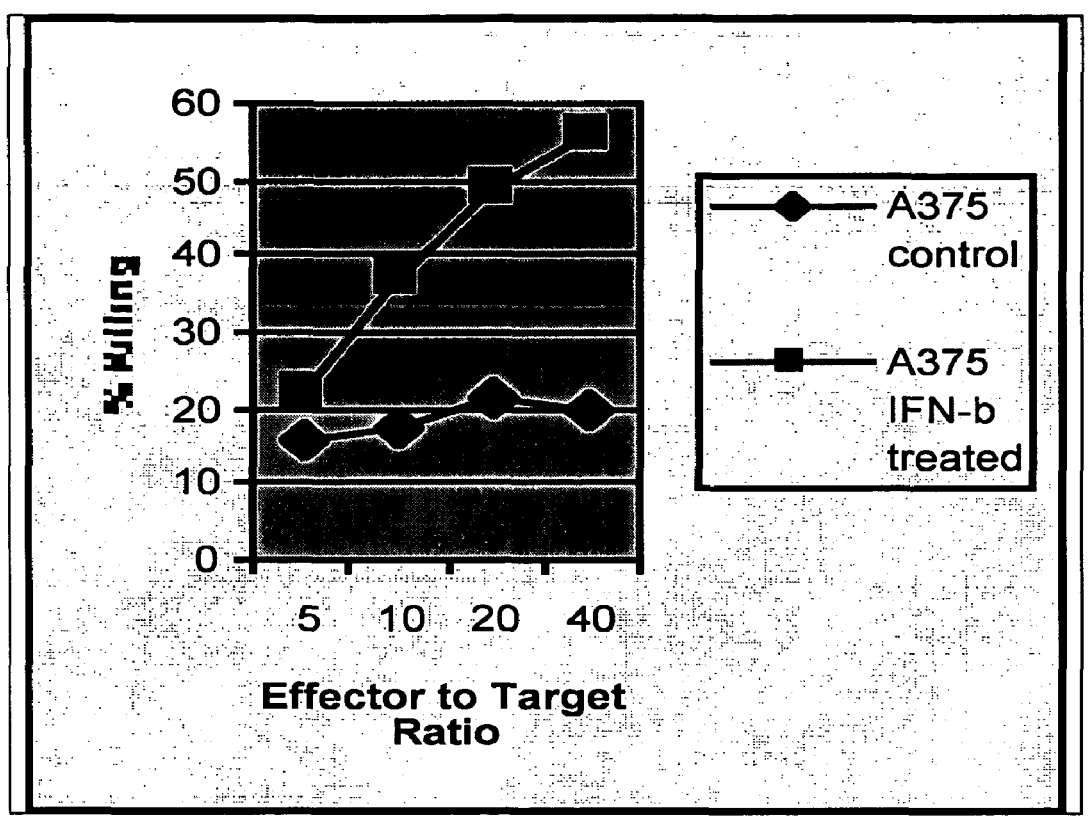
FIG. 7 illustrates increased killing by T lymphocytes following IFN-β treatment of melanoma cells.

As shown in FIG. 7, up-regulation of antigen expression induced by IFN-β results in melanoma cells that can be killed by T lymphocytes. These results demonstrate that IFN-β can increase targeting of tumor cells by the immune system.

Example VI

This example describes recombinant constructs used for screening compounds which effect tumor-antigen expression.

To identify other compounds having the same effect as interferon-beta, recombinant DNA constructs which contain a sequence tag (e.g. luciferase, or green fluorescent protein (GFP) or an enzyme activity) linked to a Melan-A/MART-1 regulatory element (e.g., promoter) can be constructed and inserted into Melan-A/MART-1 melanoma cells (e.g., a low expressor cell line). Transfected cell lines can then used for screening of small organic compounds and larger compounds having biological activity, e.g., compounds that up-regulate expression of Melan-A/MART-1, and other antigens.

Figure 8:
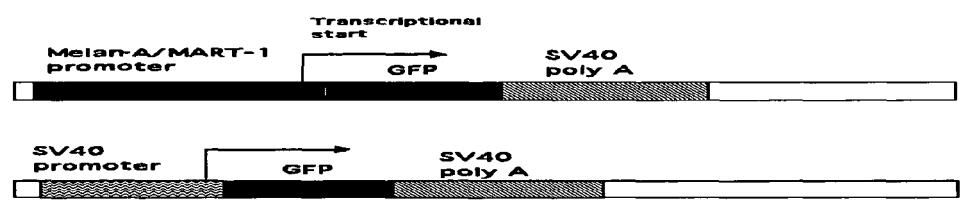
FIG. 8 illustrates an exemplary reporter construct to identify compounds having an activity of IFN-β. GFP reporter gene driven by the 1176-bp Melan-A/MART-1 promoter.

For identification of TAA modulating agents, a reporter that incorporates the promoter region from the Melan-A/MART-1 melanocyte lineage differentiation antigen and tag sequence was constructed. The exemplary construct including green fluorescent protein (GFP) is illustrated in FIG. 8. GFP reporter systems have been previously described (Haseloff, (1999). Methods Cell Biol 58:139; Tsien (1998). Annu Rev Biochem 67:509; Chiesa et al. (2001). Biochem J 355:1; Belmont (2001). Trends Cell Biol 11:250).

Figure 9:
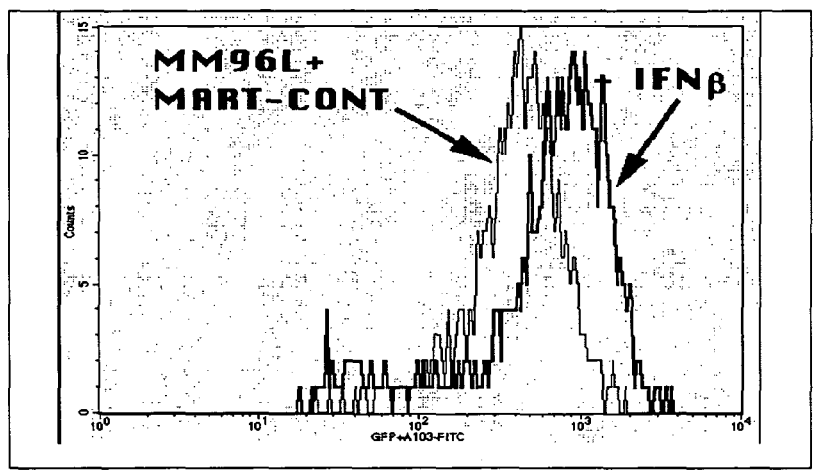
FIG. 9 illustrates augmentation of GFP fluorescence following exposure of transfected cells to IFN-β.

A number of melanoma cells have been transfected with linearized constructs expressing GFP from an extended Melan-A/MART-1 promoter (1176 bp) and separately with a construct expressing GFP by means of the SV40 promoter (depicted in FIG. 8). Stable transfectants were selected by co-transfection with a plasmid conferring resistance to Geneticin (G418). The expression results of such constructs are shown in FIG. 9.

(SEQ ID NO: 26)
Melan-A/MART-1 promoter
AGATCCTGCCACTGCACTCCAGCCTGGGCGACAGAG

TGAGTCTCCATCTCAGAAAAAAAAAATGTGTTTGAG

CCTAGTTATAATGATTTAAAATTCATGGTCCGACAC

CGCAATTACTTTTGCACCAACCTAATTGATGTCTAA

GTAGGTCATATTCTACCTGCAAAAAGAAAATTTCAT

CTATCCCTTTCACATAGATGGAAACCCACTATCTCC

```
AGTGGACAGTTAACACCAAAGGCATCACAGAGAACT

CATGGAGCTCAGCTGAGGAGGTTTCAGGGATTTTTC

TATTTCCTTTTCTTGATTATGAGAGTCTGGGACTAG

ATGCTCTCCAGACCTGTGCCTAAAGACTCTTCAACC

CTTTGAGATGGAGATGAGGGAGGGAATAGGGAACCC

AGTTTAGTTTGGATTTCAGATCCTTTTGTGGGTCAT

AAGCGTGATGATTGGGTTTCCATGTTCACGTGTGAG

ATATGCCTCCCTCAAACCTTGTTACAATGACATGGG

CACCTTACCTATCTGACATGAGAAAAACAAATGTGG

ATTTCAGATAAACAAAAAATAACTCTTTTAGTGTAT

ATGTCCCATAGAATATGTGGACATATTTATCCTAAA

AATATTGTATGGGACATAGTTGTATTAAGAAACTGT

TCATTGTTTATCTGAAGTTCAAATTTAACTGGGCAT

CCTCCTCAGCTGAGCTCCATGAGTTCTCTGTGATGC

CTTTGGTGTTAACTGTCCACTGGAGATAGTGGGTTT

CCATCTATGTGAAAGGGATAGATGAAATTTTCTTTT

TGCAGGTAGAATATGACCTACTTAGACATCAATTAG

GTTGGTGCAAAAGTAATTGTGGTGTCGGACCATGAA

TTTTAAATCATTATAACTAGGCTCATGTCATATTTT

ATGTGACATGGCAATCCTATGGAGGAGGGACCAACA

TTTAAAATAAATGGCTTCCCTAGGATAGAGCACTGG

GACTGGGGAAAACAGAGGCCACAGTCAGCTGTGACT

TTTTGAAGGAAGGAATAAAGTTGGTTTCTTTCATGC

CAATTTAGCAATTACAGACGACCCCGTCAGAAATCT

AAACCCGTGACTATCATGGGACTCAAAACCAGGAAA

AAAAATAAGTCAAAACGATTAAGAGCCAGAGAAGCA

GTCTTCATACACGCGGCCAGCCA (SEQ ID NO: 27)
GFP coding sequence
ATGGTGAGCAAGGGCGAGGAGCTGTTCACCGGGGTG

GTGCCCATCCTGGTCGAGCTGGACGGCGACGTAAAC

GGCCACAAGTTCAGCGTGTCCGGCGAGGGCGAGGGC

GATGCCACCTACGGCAAGCTGACCCTGAAGTTCATC

TGCACCACCGGCAAGCTGCCCGTGCCCTGGCCCACC

CTCGTGACCACCCTGACCTACGGCGTGCAGTGCTTC

AGCCGCTACCCCGACCACATGAAGCAGCACGACTTC

TTCAAGTCCGCCATGCCCGAAGGCTACGTCCAGGAG

CGCACCATCTTCTTCAAGGACGACGGCAACTACAAG

ACCCGCGCCGAGGTGAAGTTCGAGGGCGACACCCTG

GTGAACCGCATCGAGCTGAAGGGCATCGACTTCAAG

GAGGACGGCAACATCCTGGGGCACAAGCTGGAGTAC

AACTACAACAGCCACAACGTCTATATCATGGCCGAC

AAGCAGAAGAACGGCATCAAGGTGAACTTCAAGATC

CGCCACAACATCGAGGACGGCAGCGTGCAGCTCGCC

GACCACTACCAGCAGAACACCCCCATCGGCGACGGC

CCCGTGCTGCTGCCCGACAACCACTACCTGAGCACC

CAGTCCGCCCTGAGCAAAGACCCCAACGAGAAGCGC

GATCACATGGTCCTGCTGGAGTTCGTGACCGCCGCC

GGGATCACTCTCGGCATGGACGAGCTGTACAAGTAA
                                    (SEQ ID NO: 28)
SV40 late polyA signal
CAGACATGATAAGATACATTGATGAGTTTGGACAAA

CCACAACTAGAATGCAGTGAAAAAAATGCTTTATTT

GTGAAATTTGTGATGCTATTGCTTTATTTGTAACCA

TTATAAGCTGCAATAAACAAGTTAACAACAACAATT

GCATTCATTTTATGTTTCAGGTTCAGGGGAGGTGT

GGGAGGTTTTTAAAGCAAGTAAAACCTCTACAAAT

GTGGTA
```

The above sequences are the relevant functional portions of reporter transfected into the appropriate cell lines such that GFP can be expressed from the Melan-A/MART-1 promoter (in cells with the right transcriptional apparatus; i.e. "high" Melan-A/MART-1 cells). An "extended" MART promoter (1176 bp) was derived from amplification of human genomic DNA with primers corresponding to the 5' and 3' ends of the sequence as shown. GFP sequence ("EGFP") is from a Clontech vector. Initiation codon is underlined; termination TAA codon at end of this segment. SV40 late poly A signal: SV40 sequences are widely used and are known in the art. No intronic sequences are present in the construct.

In brief, both high and low antigen expressing cells, MM96L and A375, respectively, were transfected with the exemplary Melan-A/MART-1-GFP recombinant reporter construct (FIG. 8). After cloning out cells containing the construct, the effect of interferon-β was studied.

The MM96L-Melan-A/MART-1-GFP reporter cells treated with IFN-β for 72 hours showed augmentation of GFP fluorescence (GFP emission is shown in FIG. 9), in common with its endogenous Melan-A/MART-1 gene. A375 reporter cells treated with IFN-β also showed augmentation of GFP fluorescence. In contrast, SV40 promoter-driven GFP exhibited no such response. This data therefore demonstrated that the GFP reporter systems recapitulated the regulation of native Melan-A/MART-1 gene. A reporter driven by Melan-A/MART-1 regulatory region cellular system is therefore useful for screening and identifying compounds, agents and drugs that up-regulate antigen expression.

These reporter constructs can be employed in vivo. For example, tumor cells can be propagated subcutaneously in immunodeficient mice, and induced with IFN-β in vivo. The tumors can be injected directly with antigen-up-regulators (e.g., IFN-β, assuring that there is local drug available. Mice can also be treated with IFN-β subcutaneously following establishment of antigen negative tumor cells (such as MU-X and A375). By biopsying subcutaneous tumor sites at regular intervals following IFN-β therapy, a time-course for induction of antigen will be developed. Any reversion of tumor cells to antigen-negative status following termination of drug therapy can also be studied. Also, since human T cells that are able to recognize and lyse antigen positive tumors are available, tumor biopsies stained with antibody to human CD3 can demonstrate altered infiltrating of adoptively transferred human CTL following antigen-induction therapy. In particular, observing the recruitment of T cells to tumors that are expressing GFP, as opposed to those that are GFP negative, as a demonstration of induced tumor antigen (Melan-A/MART-1). The studies using GFP-transfected tumor cells will parallel those for the un-transfected cells described below.

Example VII

This example describes in vivo applications of IFN-β and tumor associated antigens (TAAs). This example also describes exemplary assays for monitoring the effect of IFN-β alone and in combination with TAAs.

IFN-β is safe and well-tolerated in ambulatory patients, thus providing an agent with relatively well-described in vivo toxicities and tolerances. By combining IFN-β therapy with tumor-associated antigens, both enhanced immunity and enhanced tumor antigen expression leading to more effective tumor killing in vivo are expected. T cell immunity and tumor antigen expression during in vivo administration, and correlating clinical responses with the induction of T cells specific for tumor antigens, as well as with antigen expression by the tumors, before, during and after therapy has been instituted will be analyzed.

Human tumor xenografts in mice will enable evaluation of the in vivo induction of tumor (e.g., melanocyte) antigens. Both antigen-positive and antigen-negative tumor cells can co-exist in human tumors that have developed spontaneously over a period of months to years. Tumor heterogeneity is not readily demonstrable in tumor transplant models where the tumor-injected animals are inherently short-lived, and generally the tumors are clonally homogeneous during the course of the studies. Thus, although tumors in animal models may not absolutely reflect tumors in humans, there are compelling reasons to develop animal models employing low antigen expressing xenografts. For example, prognosis for a melanoma patient with established metastatic disease is quite poor even with aggressive current therapies, and the use of immunotherapies alone have shown limited success even when rather innovative treatment regimes have been employed.

Animal treatments include combining multi-epitope tumor (e.g., melanocyte) antigen with IFN-β therapy to induce enhanced host immunity against the tumors, or to maintain and increase tumor antigen expression to enhance recognition of tumor cells which might otherwise escape immune destruction. Clinical endpoints include assessment of both host immunity and expression of tumor antigens, achieving improved host immunity (systemic and intra-tumoral cellular and huimoral immunity; Melan-A, MAGE-10, and NY-ESO-1b specific CD8$^+$ T cells—measured by tetramer method, Melan-A, MAGE-10, and NY-ESO-1b specific activated (interferon gamma releasing) CD8$^+$ T cells—measured by ELISPOT; DTH to tyrosinase leader, Melan-A, MAGE-10, and NY-ESO-1b peptide; NY-ESO-1 reactive antibodies, etc.) or inhibition of tumor growth or tumor destruction (measurement of tumor size) in patients with tumors, such as melanoma; and toxicities and adverse events (as defined by National Cancer Institute Common Toxicity Criteria (CTC) Scale).

TAAs used are components of proteins recognized by the autologous immune system on tumors such as melanomas. One of more TAAs could be expressed in the tumor. Expression of tyrosinase, Melan-A, NY-ESO-1, LAGE, and MAGE-10 in tumor tissue can be tested by reverse transcription-polymerase chain reaction (RT-PCR) analysis or immunohistochemistry. As all study peptides are presented by HLA-A2, patients expressing HLA-A2 are treatment candidates.

Enhanced immunity to the antigen Melan-A has been observed when Montanide ISA™ 51 is used as an adjuvant with Melan-A peptide. The addition of Montanide ISA™ 51 to TAAs given with or without IFN-β is likely to lead to enhanced immunological and clinically beneficial effects in melanoma patients.

Exemplary TAAs, formulations and routes of administration are as follows:

Tyrosinase leader: HLA-A2 binding peptide encoded by tyrosinase gene; sequence MLLAVLYCL (SEQ ID NO:2); position 1-9
  Formulation: 333 μg/mL tyrosinase leader in 100% DMSO
  Intended dose: 100 μg
  Vial size: 1-mL vial with 0.45 mL peptide solution
  Route of administration: intradermal
  Source: LICR Melan-A ELA: Analog of HLA-A2 binding peptide encoded by Melan-A gene; sequence ELAGIGILTV (SEQ ID NO:23); position 26-35 (E27L)
  Formulation: 333 μg/mL peptide in 30% DMSO in phosphate buffered saline
  Intended dose: 100 μg
  Vial size: 1-mL vial with 0.45 mL peptide solution
  Route of administration: intradermal
  Source: LICR MAGE-10.A: HLA-A2 binding peptide encoded by MAGE gene; sequence GLYDGMEHL (SEQ ID NO:24); position 254-262
  Formulation: lyophilized powder
  Intended dose: 300 μg
  Vial size: 1-mL vial with 400 μg peptide
  Route of administration: intradermal
  Source: LICR NY-ESO-1b: HLA-A2 binding peptide encoded by NY-ESO-1 gene; sequence SLLMWITQC (SEQ ID NO:25); position 157-165
  Formulation: 2 mg/mL NY-ESO-1b in 100% DMSO
  Intended dose: 100 μg
  Vial size: 1-mL vial with 0.3 mL peptide solution
  Route of administration: intradermal
  Source: LICR Montanide ISA-51
  Formulation: montanide oleate (Montanide 80) in mineral oil solution (Drakeol 6VR)
  Intended dose: 1.0 mL
  Vial size: 3 ML
  Route of administration: subcutaneous
  Source: SEPPIC, Paris, France Interferon β
  Rebif® 22 ug (6×10$^6$ IU)/vial Serono, Rockland, Mass.

Exemplary patient inclusion criteria include one or more of the following, for example, confirmation of metastatic melanoma; HLA-A2 positive; Relapsed Stage IV melanoma with lesions that are resectable or accessible to biopsy; at least 4 weeks since surgery before initiating protocol; at least 4 weeks since the last chemotherapy, biologic therapy, or immunotherapy; no concurrent biologic therapy or immunotherapy; performance status >70 (Karnofsky Scale); and life expectancy ≧4 months.

Exemplary laboratory values of candidate patients can be within the following limits:

| | |
|---|---|
| Hemoglobin | $\geq 9.0$ g/dL |
| | $\geq 10.0$ g/dL (if <50 kg) |
| Neutrophil count | $\geq 1.5 \times 10^9$/L |
| Lymphocyte count | $\geq 0.5 \times 10^9$/L |
| Platelet count | $\geq 100 \times 10^9$/L |
| Serum creatinine | $\leq 1.8$ mg/dL |
| Serum bilirubin | $\leq 2$ mg/dL |

Optional exemplary patient exclusion criteria include one or more of the following, for example, clinically significant heart disease (NYHA Class III or IV); serious illnesses, eg, serious infections requiring antibiotics, bleeding disorders; prior bone marrow or stem cell transplant; history of immunodeficiency disease or autoimmune disease; metastatic disease to the central nervous system, unless treated and stable; HIV positive; chemotherapy, radiation therapy, or immunotherapy within 4 weeks before study entry (6 weeks for nitrosoureas); concomitant treatment with steroids, antihistaminic drugs, or nonsteroidal anti-inflammatory drugs (unless used in low doses for prevention of an acute cardiovascular event or for pain control)—topical or inhalational steroids are permitted; participation in another clinical trial within 4 weeks prior to enrollment; pregnancy or lactation; women of childbearing potential not using a medically acceptable means of contraception; unavailability of the patient for immunological and clinical follow-up assessment.

For melanoma, an exemplary protocol employs one or more of four TAA peptides (melanoma peptide vaccine) comprising a tyrosinase leader, Melan-A ELA, MAGE-10.A2 and NY-ESO-1b. Peptide(s) will be administered by subcutaneous injection every 3 weeks for six vaccinations. Peptides will be mixed together with Montanide ISA-51 and given at separate injection sites. In addition, patients will be randomized to receive or not to receive IFN-β by subcutaneous injection, 3 times weekly (M, W F) (6 million units per injection of IFN-β) for each of the three weeks between the vaccine boosts, beginning at week 7 (i.e. with the third vaccine injection). This protocol will allow for primary and early secondary immune responses to be initiated prior to introducing an agent that is unlikely to alter effector phase immune responses, but might alter the cytokine repertoire during initial vaccine induction of anti-tumor immunity. Waiting for an early immune response to develop minimizes the time for IFN-resistant tumors to be selected before the immune response has been sufficiently enhanced to destroy tumors having up-regulated antigen expression.

Patients can be monitored for toxicity after each vaccine and IFN-β injection. Systemic immunity can be assayed using blood samples to be obtained at baseline and at specified time points, for the assessment of peptide-specific antibodies by ELISA, as well as peptide-specific CD8$^+$ T cells by tetramer analysis and ELISPOT. Peptide-specific delayed-type hypersensitivity (DTH) skin reaction will be measured at baseline and after the third and sixth set of peptide injections. If DTH reactions occur at other time points, they will be measured. Tissue samples from one metastatic lesion will be obtained at baseline and at least one time after two cycles of interferon β treatment for evaluation of antigen expression. Additional tests for peptide-specific cellular and humoral immunity will be done two weeks after the sixth set of peptide injections. Clinical hematology and biochemistry measurements will be taken at baseline, and as specified in the protocol schema. Disease status will be assessed at baseline and two weeks after the sixth set of peptide injections.

Whenever accessible tumor deposits are available, and can be biopsied, or excised with minimal risk to the patients being treated, both intra-tumor immunity and histology and antigen expression on tumor cells will be investigated. 3 types of tests will be performed whenever sufficient tissue is available to allow for the following assays:

Histology and antigen expression on tumor cells: Routine histology will be performed to evaluate tumor necrosis and the status of infiltrating lymphocytes. Frozen sections of tumor tissue will also be stained for expression of the antigens to determine both intensity and heterogeneity in antigen expression, particularly with respect to any regressing or progressing lesions. In addition to evaluation of tumor and host immune responses, image analysis of tumor antigen expression and micro-dissection specimens for amplification of mRNA for quantitative PCR analysis on tumors before and after therapy will be conducted.

Image Analysis: In order to evaluate enhanced MHC and melanocyte antigen expression, biopsies will be stained with antibodies to HLA Class I and II antigens, as there should be an increase in MHC expression if the tumor cells are responsive to IFN-β. In parallel, the tissues will be stained with antibodies to the tumor-associated antigens (Melan-A, Tyrosinase, NY-ESO and MAGE-10). Both immunoperoxidase staining and FITC-fluorescent-tagged antibody staining will be performed to acquire quantitative data on the levels of antigen expression in the tissue as a whole, and tumor cells individually.

Molecular Analysis of single tumor cells present in biopsies post therapy: In addition to conventional histological techniques, using laser capture micro-dissection technology, individual tumor cells will be evaluated for expression of a larger series of melanocyte associated antigens and transcription factors to determine not only which of the vaccine antigens are expressed, but also to determine if there is more consistent expression of additional melanocyte lineage antigens that is more amenable to targeting in subsequent treatments. Inclusion of the following genes (Table 2) will allow evaluation of improved immunotherapy protocols should additional antigens prove to be more amenable to homogeneous expression either with or without additional induction by IFN-β. In addition to the choice of genes encoding the vaccine antigens and HLA-A2, selection of the panel genes is made on the basis of their relevance to the melanocytic lineage, known role in controlling melanocytic gene expression, relevance to the IFN-β response, and as control markers.

At the single cell level correlations between levels of mRNAs expressed from antigen genes and those expressed from chosen transcription factor genes during the course of the treatment can be evaluated. MITF-M is strongly associated with the control of expression of a number of melanocytic antigens including tyrosinase and Melan-A/MART-1. SOX10 is one transcription factor in turn regulating MITF-M, and which is not expressed in some of the low antigen-expressing cell lines. Type I interferons (including IFN-α and IFN-β) use a common receptor composed of two subunits. Examining expression of other antigen genes in addition to those included in the vaccine preparation will be performed as expression of melanocytic antigens is regulated coordinately. Up- or down-regulation of Melan-A/MART-1, for example, is often correlated with a corresponding change in TRP-1, TRP-2, and gp100 expression.

Evaluation of biopsy material from treated patients to determine which antigens are still expressed, and which are enhanced by IFN-β will to help evaluate tumor heterogeneity, and more importantly, homogeneity of antigen expression that can be utilized for identification of targets that will make immunotherapy a more successful approach.

TABLE 2

Exemplary genes to be evaluated for expression in tumor cells.

| Gene Classification | Gene Name |
|---|---|
| Antigens in vaccine | Melan-A, tyrosinase, MAGE1-A2, NY-ESO-1b |
| HLA | HLA-A2 |
| Other Melanoma-Associated Antigens | TRP1, TRP2, gp100 (pmel 17) |
| Melanoma Associated Transcription Factors | MITF-M, SOX10 |
| IFN-Type I Receptor | IFNAR-1, IFNAR-2 |
| Other Markers | MITF-A, β-Actin |

TaqMan chemistry and appropriate instrumentation allows rigorous quantitative PCR analysis of mRNA levels of desired molecular targets, and has been applied towards single-cell analyses. To obtain information regarding expression of a panel of markers, some of which may be at low copy number per individual cell, an amplification step from each single-cell mRNA source will be performed, where it is critical that such a step faithfully preserves the relative abundance of each species within the mRNA transcriptome. With single or low numbers of cells, T7 RNA polymerase-mediated amplification via the generation of complementary RNA transcripts (cRNAs) (Eberwine. (1996). Biotechniques, 20:584; Luo, et al., (1999). Nat Med, 5:117; and Abe, et al., (2003). J Hum Genet, 48:142) can generate long in vitro transcripts (Riechmann, et al., (1990). Virology, 177:710; Puurand, et al., Virus Res, 40:135, 1996; and Shi, et al., (2002). J Virol, 76:5847), well in excess of the MITF mRNAs. Following T7 polymerase-mediated amplification, the resulting cRNAs are reverse-transcribed with random hexamers for subsequent TaqMan Q-PCR analysis.

The "housekeeping" genes commonly used for normalization purposes in a variety of expression-based studies (β-actin, GAPDH) have been noted as problematic for tissue-based and single-cell studies. Thus, a presynthesized internal spiked standard in the assays, in the form of a surrogate non-mammalian mRNA (luciferase) generated by in vitro transcription, will be added. This is achieved by cloning luciferase coding sequence into Promega Corp. vector pSP64polyA, and preparing polyA+ run-off in vitro transcripts with SP6 polymerase. The plasmid template is digested with RNase-free DNAse, the RNA transcripts purified by three cycles of ammonium acetate precipitation, quantitated spectrophotometrically and gel tested for full-length integrity. If necessary, full-length species will be purified by excision of the correct gel band and extraction from agarose. A quantity equivalent to 100 copies of polyA+ luciferase RNA will be added to each cell lysate prior to initial reverse-transcription, second-strand cDNA synthesis and subsequent T7 polymerase amplification of cRNA. In consequence, detection of the internal introduced standard (with its own specific primer/probe TaqMan system) will have identical enzymatic requirements as for the cellular mRNAs themselves. Levels of each target gene in the above panel will then be expressed as ratios to the levels of the introduced standard. β-actin (high abundance mRNA) and MITF-A (moderate to low abundance mRNA) is included in the gene panel for single-cell analysis (Table 2) as widely-expressed controls for confirming that the endogenous mRNAs themselves from each cellular isolate are intact. Normalization will more accurately use the introduced surrogate mRNA standard.

In addition to analyzing immunity represented in the circulating lymphocytes in the blood, intra-tumoral lymphocytes with tetramers will be stained to determine the frequency of peptide-specific CD8+ T cells present within the tumor tissue. Furthermore, by culturing small tumor fragments in the presence of Interleukin-2, large numbers of in vivo-activated tumor-infiltrating lymphocytes can be further studied for cytotoxic activity against tumor targets (Hishii, et al., (1997). Proc. Natl. Acad Sci (USA), 94:1378; Ramirez-Montagut, et al., (2000). 119:11; Kradin, et al., (1989). Lancet, 1:577; Hishii, et al., (1999). Clin Exp Immunol, 116:388; and Pandolfi, et al., (1991). Cancer Res., 51:3164) from the same patient when available, and from HLA-A2 matched cell lines if autologous tumor target is unavailable. Functional assessment of cytotoxic activity will complement the tetramer assays, which will give an indication of the frequency of T-cell receptor positive cells with specificity for the tumor vaccine antigens. These studies will indicate whether TAAs administered with IFN-β, increase local tumor immunity for successful tumor immunotherapy.

Although it is anticipated that there will be a measure of tumor antigen heterogeneity in tumor biopsies, both antigen positive and antigen-deficient tumor cells can show enhanced tumor antigen expression following treatment with IFN-β. Evaluating the ability of tumor to up-regulate both melanocyte lineage antigens and HLA antigens will reveal whether individual tumor deposits contain IFN-responsive tumor cells. In the event tumor cells show no antigen induction, the possibility of lost IFN-receptors, or lost IFN-response elements would be expected to limit the efficacy of antigen-upregulation therapy.

The combined therapy (e.g, IFN-beta and TAAs) will enhance clinical responses in tumor (e.g., melanoma) patients via enhanced antigen expression, improved cell-mediated immunity and destruction of tumor cells with antigen expression. To the extent that tumor remains after therapy, evaluation of tumor antigen expression and host immune response in situ will allow refinements in the treatment protocol. For example, if there is loss of TAA expression that is present in the vaccine, but retention of other TAAs on the tumor cells, a follow-up administration could be performed using different TAAs to which T cells can be targeted. Also, if TAAs not represented in the original vaccine are up-regulated with IFN-β, future administrations can include such TAAs responsive to up-regulation.

Tissue Processing and Analysis: For tissue sample processing, laser capture microdissection (LCM) has emerged as a revolutionary technique for genetic analysis, combining precise microscopy with molecular expression profiling at the single cell level (Emmert-Buck, et al., (1996). Science, 274: 921; Schutze and Lahr, (1998). Nat Biotechnol, 16:737; Sgroi, et al., (1999). Cancer Res, 59:5656; Miura, et al., (2002). Cancer Res, 62:3244; De Preter, et al., (2003). Cancer Lett, 197:53; and Fend and Raffeld, (2000). J Clin Pathol, 53:666). The same processing scheme towards single-cell analysis of archived samples of primary resected tumor samples from each of the patients in the study will be applied. Preserved paraffin-embedded materials can be used as sources of such material by means of laser-capture microdissection.

For each patient biopsy sample LCM 20 single cell isolates with morphological characteristics of melanoma tumor cells will be obtained. Subsequently, with the procedure described above, quantitative fluorogenic PCR with the TaqMan chemistry as described (Xiang, et al., (2001). Immunol Cell Biol, 79:472) will be performed using triplicate determinations in each case. To improve the screening rate and for reasons of economy, the 384-well plate format now available with the TaqMan instrumentation will be employed. Primers and probes will be designed with PrimerExpress software, with the primers positioned such that they span large introns if possible (this is feasible in all cases). In any case, owing to the cRNA amplification step, it is unlikely that the minimal amount of genomic DNA contributed by the original target cell will be a confounding factor for expression analysis. Preliminary studies will define optimal probe concentrations for each primer/probe combination. Also, preliminary work will be performed to determine the assay sensitivity achievable with the cRNA amplification under the conditions. In practical terms, this means the amount of total reverse-transcribed cRNA needed for accurate Q-PCR. Since >1000-fold amplification with the T7 RNA polymerase is readily achievable in even a single round (Eberwine, (1996), supra), limitations from the amounts of amplified target cRNA is unlikely.

Mouse Models: Murine tumor models, developed in an immunodeficient mouse, will provide a system to develop or evaluate assays for monitoring the human clinical trial as well as testing the efficacy of IFN-β to up-regulate antigen expression in vivo. This work will afford an opportunity for comparison of the responses in both human clinical trial and the in vivo mouse model.

Human tumor cell lines will be propagated in culture and implanted into rag 2-deficient (rag-2$^{-/-}$) mice. When rag2$^{-/-}$ mice are challenged with 1×10$^6$ melanoma cells, palpable tumors are apparent within 2 weeks and these tumors reach an approximate area of 200 mm$^2$ within 4 weeks. In brief, rag$^{-/-}$ mice will be injected in the s.c space with 1×10$^6$ melanoma cells. When tumors reach a size of 100 mm$^2$, mice will be randomly assigned to groups of 5 for treatment. "Control" animals will be treated with an injection of compound diluent. 'Protocol' animals will be treated with compounds using escalating doses reflective of previous reports (Clemons, et al., (2002). Pancreas, 25:251) (serum levels of IFN-β will be monitored by ELISA). Treatments will be continued every other day for one week. Every other day for 7 days, mice will be sacrificed and tumors excised and evaluated. Each tumor will be dissociated using collagenase and dispase solutions. The resulting single cell suspension will be used for flow cytometric or PCR analysis of antigen expression as with in vitro cultured cells. Each set of studies will be repeated twice.

High and low antigen expressing tumor cells, MU and MU-X, cultured in individual mice will be subjected to fine needle biopsies to provide cells for single cell PCR and immunohistochemical experimentation. Expression of mRNA for the genes listed in Table 2 will be evaluated by the same single-cell Q-PCR procedure as described above.

Immunodeficient mouse models will be used to evaluate the ability of antigen-enhancing agents to up-regulate tumor antigen expression in vivo. Multiple antigen induction observed in human melanoma cells in vitro will be evaluated in vivo. Bio-availability of IFN-β in animal tumor models, using doses of antigen up-regulatory agents that will be sub-lethal to the mouse, will be determined. Both MU and MU-X tumor cells can be grown in immunodeficient mice in subcutaneous sites (Fukumura, et al., (1995). Cancer Res, 55:4824). These studies will allow refinements to human clinical trial described above, as regards immunohistochemistry and single cell rtPCR evaluation of antigen expression.

A typical dosing efficacy protocol is described below for comparing the response of antigen positive (MU) and antigen negative (MU-X) tumor cells. In each case tumors will be stained with antibodies to Melan-A/MART-1 (A103), gp100/pmel17 (HMB45) and HLA Class I antigen (W6/32). In addition, RNA will be extracted for PCR assessment of induction of mRNA for these and other melanocyte lineage antigens.

120 animals total per study:

15 animals receiving only MU-X tumor and injected with saline only on day 0. Tumor will be excised daily from 5 animals for in vitro assay of antigen expression at days 1, 3 and 7.

*45 animals receiving MU-X tumor followed by intravenous injection of IFN-β on day 0 at 3 dosage levels (10, 100, and 1000 IU/g animal weight). Tumor will be excised from 5 animals in each dosage group for in vitro assay of antigen expression at days days 1, 3 and 7.

15 animals receiving only MU tumor and injected with saline only on day 0. Tumor will be excised daily from 5 animals for in vitro assay of antigen expression at days days 1, 3 and 7.

*45 animals receiving MU tumor followed by intralesional injection of human IFN-β on day 0 at 3 dosage levels (10, 100, and 1000 IU/g animal weight). Tumor will be excised from 5 animals in each dosage group for in vitro assay of antigen expression at days days 1, 3 and 7.

What is claimed:

1. A method of treating a melanoma comprising administering to a subject with a melanoma an amount of interferon-β (IFN-β) receptor agonist to up-regulate expression of a tumor associated antigen (TAA) on the melanoma followed by administering an autologous immune cell that interacts with a melanoma cell of the melanoma, wherein the IFN-β receptor agonist comprises a polypeptide comprising the amino acid sequence of SEQ ID NO: 29 or SEQ ID NO: 30, and wherein the TAA is selected from the group consisting of Melan-A/MART-1, gp100, tyrosinase, NY-ESO-1, MAGE, MITF, and SOX-10, thereby treating the melanoma.

2. The method of claim 1, wherein the immune cell is a lymphocyte.

3. The method of claim 2, wherein the lymphocyte is a T lymphocyte.

4. The method of claim 1, wherein the amino acid sequence of the polypeptide comprises the amino acid sequence set forth in SEQ ID NO: 29.

5. The method of claim 4, wherein the amino acid sequence of the polypeptide consists of the amino acid sequence set forth in SEQ ID NO: 29.

6. The method of claim 1, wherein the amino acid sequence of the polypeptide comprises the amino acid sequence set forth in SEQ ID NO: 30.

7. The method of claim 6, wherein the amino acid sequence of the polypeptide consists of the amino acid sequence set forth in SEQ ID NO: 30.

8. The method of claim 1, wherein the melanoma is metastatic.

9. The method of claim 1, wherein the treatment reduces melanoma volume, inhibits an increase in melanoma volume, stimulates melanoma cell lysis or apoptosis, or reduces melanoma metastasis.

10. The method of claim 1, further comprising administering an anti-tumor therapy.

11. The method of claim 10, wherein the anti-tumor therapy comprises surgical resection, radiotherapy, or chemotherapy.

12. The method of claim 1, wherein the TAA is Melan-A/MART-1.

13. The method of claim 1, wherein the TAA is gp100.

14. The method of claim 1, wherein the TAA is tyrosinase.

15. The method of claim 1, wherein the TAA is NY-ESO-1.

16. The method of claim 1, wherein the TAA is MAGE.

17. The method of claim 1, wherein the TAA is MITF.

18. The method of claim 1, wherein the TAA is SOX-10.

19. A method of treating a glioma comprising administering to a subject with a glioma an amount of interferon-β (IFN-β) receptor agonist to up-regulate expression of a tumor associated antigen (TAA) on the glioma followed by administering an autologous immune cell that interacts with a glioma cell of the glioma, wherein the IFN-β receptor agonist comprises a polypeptide comprising the amino acid sequence of SEQ ID NO: 29 or SEQ ID NO: 30, and wherein the TAA is selected from the group consisting of Melan-A/MART-1 and gp100, thereby treating the glioma.

20. The method of claim 19, wherein the immune cell is a lymphocyte.

21. The method of claim 20, wherein the lymphocyte is a T lymphocyte.

22. The method of claim 19, wherein the amino acid sequence of the polypeptide comprises the amino acid sequence set forth in SEQ ID NO: 29.

23. The method of claim 22, wherein the amino acid sequence of the polypeptide consists of the amino acid sequence set forth in SEQ ID NO: 29.

24. The method of claim 19, wherein the amino acid sequence of the polypeptide comprises the amino acid sequence set forth in SEQ ID NO: 30.

25. The method of claim 24, wherein the amino acid sequence of the polypeptide consists of the amino acid sequence set forth in SEQ ID NO: 30.

26. The method of claim 19, wherein the treatment reduces glioma volume, inhibits an increase in glioma volume, stimulates glioma cell lysis or apoptosis, or reduces glioma metastasis.

27. The method of claim 19, further comprising administering an anti-tumor therapy.

28. The method of claim 27, wherein the anti-tumor therapy comprises surgical resection, radiotherapy, or chemotherapy.

29. The method of claim 19, wherein the glioma comprises glioblastoma, astrocytoma, or oligodendrocytoma.

30. The method of claim 19, wherein the TAA is Melan-A/MART-1.

31. The method of claim 19, wherein the TAA is gp100.

32. A method of treating a subject having or at risk of having a melanoma comprising administering to the subject
  a) an amount of interferon-β (IFN-β) receptor agonist that up-regulates expression of a tumor associated antigen (TAA) on the melanoma and
  b) the TAA, wherein the TAA is selected from the group consisting of Melan-A/MART-1, gp100, tyrosinase, NY-ESO-1, MAGE, MITF, and SOX-10, wherein the TAA is administered singly or multiple times to the subject 1 day to 6 months before administering the IFN-β receptor agonist, and wherein the IFN-β receptor agonist comprises a polypeptide comprising the amino acid sequence of SEQ ID NO: 29 or SEQ ID NO: 30, thereby treating the subject.

33. The method of claim 32, wherein the amino acid sequence of the polypeptide comprises the amino acid sequence set forth in SEQ ID NO: 29.

34. The method of claim 33, wherein the amino acid sequence of the polypeptide consists of the amino acid sequence set forth in SEQ ID NO: 29.

35. The method of claim 32, wherein the amino acid sequence of the polypeptide comprises the amino acid sequence set forth in SEQ ID NO: 30.

36. The method of claim 35, wherein the amino acid sequence of the polypeptide consists of the amino acid sequence set forth in SEQ ID NO: 30.

37. The method of claim 32, wherein the IFN-β receptor agonist is administered singly or multiple times.

38. The method of claim 32, wherein the TAA is administered singly or multiple times to the subject 1 to 14 days before administering the IFN-β receptor agonist.

39. The method of claim 32, wherein the TAA is administered singly or multiple times to the subject 14 to 30 days before administering the IFN-β receptor agonist.

40. The method of claim 32, wherein the TAA is administered singly or multiple times to the subject 1 to 6 months before administering the IFN-β receptor agonist.

41. The method of claim 32, wherein the melanoma is metastatic.

42. The method of claim 32, wherein the treatment reduces melanoma volume, inhibits an increase in melanoma volume, stimulates melanoma cell lysis or apoptosis, or reduces melanoma metastasis.

43. The method of claim 32, wherein the treatment reduces one or more adverse symptoms associated with the melanoma.

44. The method of claim 32, wherein the treatment inhibits progression of the melanoma.

45. The method of claim 32, wherein the subject is a candidate for, is undergoing, or has undergone anti-tumor therapy.

46. The method of claim 45, wherein the anti-tumor therapy comprises surgical resection, radiotherapy, or chemotherapy.

47. The method of claim 32, further comprising administering an autologous immune cell that interacts with a cell of the melanoma.

48. The method of claim 47, wherein the immune cell is a lymphocyte.

49. The method of claim 48, wherein the lymphocyte is a T lymphocyte.

50. The method of claim 32, wherein the TAA is Melan-A/MART-1.

51. The method of claim 32, wherein the TAA is gp100.

52. The method of claim 32, wherein the TAA is tyrosinase.

53. The method of claim 32, wherein the TAA is NY-ESO-1.

54. The method of claim 32, wherein the TAA is MAGE.

55. The method of claim 32, wherein the TAA is MITF.

56. The method of claim 32, wherein the TAA is SOX-10.

57. A method of treating a subject having or at risk of having a glioma comprising administering to the subject
a) an amount of interferon-β (IFN-β) receptor agonist that up-regulates expression of a tumor associated antigen (TAA) on the glioma and b) the TAA, wherein the TAA is selected from the group consisting of Melan-A/MART-1 and gp100,
wherein the TAA is administered singly or multiple times to the subject 1 day to 6 months before administering the IFN-β receptor agonist, and wherein the IFN-β receptor agonist comprises a polypeptide comprising the amino acid sequence of SEQ ID NO: 29 or SEQ ID NO: 30, thereby treating the subject.

58. The method of claim 57, wherein the amino acid sequence of the polypeptide comprises the amino acid sequence set forth in SEQ ID NO: 29.

59. The method of claim 58, wherein the amino acid sequence of the polypeptide consists of the amino acid sequence set forth in SEQ ID NO: 29.

60. The method of claim 57, wherein the amino acid sequence of the polypeptide comprises the amino acid sequence set forth in SEQ ID NO: 30.

61. The method of claim 60, wherein the amino acid sequence of the polypeptide consists of the amino acid sequence set forth in SEQ ID NO: 30.

62. The method of claim 57, wherein the IFN-β receptor agonist is administered singly or multiple times.

63. The method of claim 57, wherein the TAA is administered singly or multiple times to the subject 1 to 14 days before administering the IFN-β receptor agonist.

64. The method of claim 57, wherein the TAA is administered singly or multiple times to the subject 14 to 30 days before administering the IFN-receptor agonist.

65. The method of claim 57, wherein the TAA is administered singly or multiple times to the subject 1 to 6 months before administering the IFN-β receptor agonist.

66. The method of claim 57, wherein the treatment reduces glioma volume, inhibits an increase in glioma volume, stimulates glioma cell lysis or apoptosis, or reduces glioma metastasis.

67. The method of claim 57, wherein the treatment reduces one or more adverse symptoms associated with the glioma.

68. The method of claim 57, wherein the treatment inhibits progression of the glioma.

69. The method of claim 57, wherein the subject is a candidate for, is undergoing, or has undergone anti-tumor therapy.

70. The method of claim 69, wherein the anti-tumor therapy comprises surgical resection, radiotherapy, or chemotherapy.

71. The method of claim 57, wherein the glioma comprises glioblastoma, astrocytoma, or oligodendrocytoma.

72. The method of claim 57, further comprising administering an autologous immune cell that interacts with a cell of the glioma.

73. The method of claim 72, wherein the immune cell is a lymphocyte.

74. The method of claim 73, wherein the lymphocyte is a T lymphocyte.

75. The method of claim 57, wherein the TAA is Melan-A/MART-1.

76. The method of claim 57, wherein the TAA is gp100.

77. The method of claim 1, wherein the subject is human.

78. The method of claim 19, wherein the subject is human.

79. The method of claim 32, wherein the subject is human.

80. The method of claim 57, wherein the subject is human.

* * * * *

SEQUENCE LISTING

```
<160> NUMBER OF SEQ ID NOS: 30

<210> SEQ ID NO 1
<211> LENGTH: 9
<212> TYPE: PRT
<213> ORGANISM: Homo sapiens
<220> FEATURE:
<221> NAME/KEY: misc_feature
<223> OTHER INFORMATION: Melan-A/MART-1 peptide amino acids

<400> SEQUENCE: 1

Ala Ala Gly Ile Gly Ile Leu Thr Val
1               5

<210> SEQ ID NO 2
<211> LENGTH: 9
<212> TYPE: PRT
<213> ORGANISM: Homo sapiens
<220> FEATURE:
```

```
<221> NAME/KEY: misc_feature
<223> OTHER INFORMATION: HLA-A2 binding peptide encoded by tyrosinase
      gene

<400> SEQUENCE: 2

Met Leu Leu Ala Val Leu Tyr Cys Leu
1               5

<210> SEQ ID NO 3
<211> LENGTH: 9
<212> TYPE: PRT
<213> ORGANISM: Homo sapiens
<220> FEATURE:
<221> NAME/KEY: misc_feature
<223> OTHER INFORMATION: Tyrosinase derived peptide

<400> SEQUENCE: 3

Tyr Met Asn Gly Thr Met Ser Gln Val
1               5

<210> SEQ ID NO 4
<211> LENGTH: 9
<212> TYPE: PRT
<213> ORGANISM: Homo sapiens
<220> FEATURE:
<221> NAME/KEY: misc_feature
<223> OTHER INFORMATION: MAGE-3 derived peptide

<400> SEQUENCE: 4

Glu Asx Asp Pro Ile Gly His Leu Tyr
1               5

<210> SEQ ID NO 5
<211> LENGTH: 26
<212> TYPE: DNA
<213> ORGANISM: Homo sapiens
<220> FEATURE:
<221> NAME/KEY: misc_feature
<223> OTHER INFORMATION: Forward sense primer

<400> SEQUENCE: 5
caagatgcca agagaagatg ctcact                                          26

<210> SEQ ID NO 6
<211> LENGTH: 26
<212> TYPE: DNA
<213> ORGANISM: Homo sapiens
<220> FEATURE:
<221> NAME/KEY: misc_feature
<223> OTHER INFORMATION: Reverse anti-sense primer

<400> SEQUENCE: 6
gcttgcattt ttcctacacc attcca                                          26

<210> SEQ ID NO 7
<211> LENGTH: 22
<212> TYPE: DNA
<213> ORGANISM: Homo sapiens
<220> FEATURE:
<221> NAME/KEY: misc_feature
<223> OTHER INFORMATION: Forward sense  primer

<400> SEQUENCE: 7
gagatcactg ccctggcacc ca                                              22

<210> SEQ ID NO 8
<211> LENGTH: 27
<212> TYPE: DNA
```

```
<213> ORGANISM: Homo sapiens
<220> FEATURE:
<221> NAME/KEY: misc_feature
<223> OTHER INFORMATION: Reverse anti-sense primer

<400> SEQUENCE: 8
gctccaaccg actgctgtca ccttcac                                          27

<210> SEQ ID NO 9
<211> LENGTH: 25
<212> TYPE: DNA
<213> ORGANISM: Homo sapiens
<220> FEATURE:
<221> NAME/KEY: misc_feature
<223> OTHER INFORMATION: Forward sense primer

<400> SEQUENCE: 9
ctgattggtg caaatgcctc cttct                                            25

<210> SEQ ID NO 10
<211> LENGTH: 25
<212> TYPE: DNA
<213> ORGANISM: Homo sapiens
<220> FEATURE:
<221> NAME/KEY: misc_feature
<223> OTHER INFORMATION: Reverse anti-sense primer

<400> SEQUENCE: 10
aggaagtgct tgttccctcc atcca                                            25

<210> SEQ ID NO 11
<211> LENGTH: 25
<212> TYPE: DNA
<213> ORGANISM: Homo sapiens
<220> FEATURE:
<221> NAME/KEY: misc_feature
<223> OTHER INFORMATION: Forward sense primer

<400> SEQUENCE: 11
cagcccagca tcattcttct cctct                                            25

<210> SEQ ID NO 12
<211> LENGTH: 22
<212> TYPE: DNA
<213> ORGANISM: Homo sapiens
<220> FEATURE:
<221> NAME/KEY: misc_feature
<223> OTHER INFORMATION: Reverse anti-sense

<400> SEQUENCE: 12
gcagtgagga cggcccctac ca                                               22

<210> SEQ ID NO 13
<211> LENGTH: 21
<212> TYPE: DNA
<213> ORGANISM: Homo sapiens
<220> FEATURE:
<221> NAME/KEY: misc_feature
<223> OTHER INFORMATION: Forward sense primer

<400> SEQUENCE: 13
tgttgcccag acctgtcccc t                                                21

<210> SEQ ID NO 14
<211> LENGTH: 27
<212> TYPE: DNA
<213> ORGANISM: Homo sapiens
<220> FEATURE:
```

```
<221> NAME/KEY: misc_feature
<223> OTHER INFORMATION: Reverse anti-sense primer

<400> SEQUENCE: 14
gcaacatttc ctgcatgtct ttctcca                                              27

<210> SEQ ID NO 15
<211> LENGTH: 24
<212> TYPE: DNA
<213> ORGANISM: Homo sapiens
<220> FEATURE:
<221> NAME/KEY: misc_feature
<223> OTHER INFORMATION: Forward sense primer

<400> SEQUENCE: 15
cctagtgaac aaggagtgct gccc                                                 24

<210> SEQ ID NO 16
<211> LENGTH: 27
<212> TYPE: DNA
<213> ORGANISM: Homo sapiens
<220> FEATURE:
<221> NAME/KEY: misc_feature
<223> OTHER INFORMATION: Reverse anti-sense primer

<400> SEQUENCE: 16
cgctggagat ctctttccag acacaac                                              27

<210> SEQ ID NO 17
<211> LENGTH: 24
<212> TYPE: DNA
<213> ORGANISM: Homo sapiens
<220> FEATURE:
<221> NAME/KEY: misc_feature
<223> OTHER INFORMATION: Forward sense primer

<400> SEQUENCE: 17
tctctcactg gattggtgcc acct                                                 24

<210> SEQ ID NO 18
<211> LENGTH: 22
<212> TYPE: DNA
<213> ORGANISM: Homo sapiens
<220> FEATURE:
<221> NAME/KEY: misc_feature
<223> OTHER INFORMATION: Reverse anti-sense primer

<400> SEQUENCE: 18
catgcctggg cactcgctct ct                                                   22

<210> SEQ ID NO 19
<211> LENGTH: 24
<212> TYPE: DNA
<213> ORGANISM: Homo sapiens
<220> FEATURE:
<221> NAME/KEY: misc_feature
<223> OTHER INFORMATION: Forward sense primer

<400> SEQUENCE: 19
ccaagcctcc gataagctcc tcca                                                 24

<210> SEQ ID NO 20
<211> LENGTH: 22
<212> TYPE: DNA
<213> ORGANISM: Homo sapiens
<220> FEATURE:
<221> NAME/KEY: misc_feature
<223> OTHER INFORMATION: Reverse anti-sense primer
```

-continued

<210> SEQ ID NO 20
<211> LENGTH: 22
<212> TYPE: DNA
<213> ORGANISM: Homo sapiens
<220> FEATURE:
<221> NAME/KEY: misc_feature
<223> OTHER INFORMATION: Forward sense primer

<400> SEQUENCE: 20
catgcctggg cactcgctct ct                                          22

<210> SEQ ID NO 21
<211> LENGTH: 26
<212> TYPE: DNA
<213> ORGANISM: Homo sapiens
<220> FEATURE:
<221> NAME/KEY: misc_feature
<223> OTHER INFORMATION: Forward sense primer

<400> SEQUENCE: 21
tgaaggtcgg agtcaacgga tttggt                                      26

<210> SEQ ID NO 22
<211> LENGTH: 23
<212> TYPE: DNA
<213> ORGANISM: Homo sapiens
<220> FEATURE:
<221> NAME/KEY: misc_feature
<223> OTHER INFORMATION: Reverse anti-sense primer

<400> SEQUENCE: 22
ctgcaaatga gccccagcct tct                                         23

<210> SEQ ID NO 23
<211> LENGTH: 10
<212> TYPE: PRT
<213> ORGANISM: Artificial Sequence
<220> FEATURE:
<223> OTHER INFORMATION: Homo sapiens peptide

<400> SEQUENCE: 23

Glu Leu Ala Gly Ile Gly Ile Leu Thr Val
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Homo sapiens peptide

<400> SEQUENCE: 24

Gly Leu Tyr Asp Gly Met Glu His Leu
1               5

<210> SEQ ID NO 25
<211> LENGTH: 9
<212> TYPE: PRT
<213> ORGANISM: Artificial Sequence
<220> FEATURE:
<223> OTHER INFORMATION: Homo sapiens peptide

<400> SEQUENCE: 25

Ser Leu Leu Met Trp Ile Thr Gln Cys
1               5

<210> SEQ ID NO 26
<211> LENGTH: 1175
<212> TYPE: DNA
<213> ORGANISM: Homo sapiens
<220> FEATURE:
<221> NAME/KEY: misc_feature
<223> OTHER INFORMATION: Melan-A/MART-1 promoter

<400> SEQUENCE: 26

```
agatcctgcc actgcactcc agcctgggcg acagagtgag tctccatctc agaaaaaaaa    60
aatgtgtttg agcctagtta taatgattta aaattcatgg tccgacaccg caattacttt   120
tgcaccaacc taattgatgt ctaagtaggt catattctac ctgcaaaaag aaaatttcat   180
ctatcccttt cacatagatg gaaacccact atctccagtg gacagttaac accaaaggca   240
tcacagagaa ctcatggagc tcagctgagg aggtttcagg gattttttcta tttccttttc   300 ttgattatga gagtctggga ctagatgctc tccagacctg tgcctaaaga ctcttcaacc   360
ctttgagatg gagatgaggg agggaatagg gaacccagtt tagtttggat ttcagatcct   420
tttgtgggtc ataagcgtga tgattgggtt tccatgttca cgtgtgagat atgcctccct   480
caaaccttgt tacaatgaca tgggcacctt acctatctga catgagaaaa acaaatgtgg   540
atttcagata aacaaaaaat aactcttttta gtgtatatgt cccatagaat atgtggacat   600
atttatccta aaaatattgt atgggacata gttgtattaa gaaactgttc attgtttatc   660
tgaagttcaa atttaactgg gcatcctcct cagctgagct ccatgagttc tctgtgatgc   720
ctttggtgtt aactgtccac tggagatagt gggtttccat ctatgtgaaa gggatagatg   780
aaattttctt tttgcaggta gaatatgacc tacttagaca tcaattaggt tggtgcaaaa   840
gtaattgtgg tgtcggacca tgaattttaa atcattataa ctaggctcat gtcatatttt   900
atgtgacatg gcaatcctat ggaggaggga ccaacattta aaataaatgg cttccctagg   960
atagagcact gggactgggg aaaacagagg ccacagtcag ctgtgactttt tgaaggaag  1020 gaataaagtt ggtttctttc atgccaattt agcaattaca gacgaccccg tcagaaatct  1080
aaacccgtga ctatcatggg actcaaaacc aggaaaaaaa ataagtcaaa acgattaaga  1140
gccagagaag cagtcttcat acacgcggcc agcca                             1175
```

<210> SEQ ID NO 27
<211> LENGTH: 720
<212> TYPE: DNA
<213> ORGANISM: Artificial Sequence
<220> FEATURE:
<223> OTHER INFORMATION: Green Fluorescent Protein derived from Aequorea
      victoria

<400> SEQUENCE: 27

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actctcggca tggacgagct gtacaagtaa   720
```

<210> SEQ ID NO 28
<211> LENGTH: 222
<212> TYPE: DNA

```
<213> ORGANISM: Simian virus 40
<220> FEATURE:
<221> NAME/KEY: misc_feature
<223> OTHER INFORMATION: SV40 late polyA signal

<400> SEQUENCE: 28
cagacatgat aagatacatt gatgagtttg gacaaaccac aactagaatg cagtgaaaaa    60
aatgctttat ttgtgaaatt tgtgatgcta ttgctttatt tgtaaccatt ataagctgca   120
ataaacaagt taacaacaac aattgcattc attttatgtt tcaggttcag ggggaggtgt   180
gggaggtttt ttaaagcaag taaaacctct acaaatgtgg ta                      222

<210> SEQ ID NO 29
<211> LENGTH: 166
<212> TYPE: PRT
<213> ORGANISM: Homo sapiens
<220> FEATURE:
<221> NAME/KEY: misc_feature
<223> OTHER INFORMATION: beta-interferon-1a

<400> SEQUENCE: 29

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 30
<211> LENGTH: 165
<212> TYPE: PRT
<213> ORGANISM: Artificial Sequence
<220> FEATURE:
<223> OTHER INFORMATION: beta-interferon-1b

<400> SEQUENCE: 30

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Gln
        35                  40                  45

Phe Gln Lys Glu Asp Ala Ala Leu Thr Ile Tyr Glu Met Leu Gln Asn
    50                  55                  60
```

```
Ile Phe Ala Ile Phe Arg Gln Asp Ser Ser Ser Thr Gly Trp Asn Glu
 65              70                  75                  80

Thr Ile Val Glu Asn Leu Leu Ala Asn Val Tyr His Gln Ile Asn His
             85                  90                  95

Leu Lys Thr Val Leu Glu Glu Lys Leu Glu Lys Glu Asp Phe Thr Arg
            100                 105                 110

Gly Lys Leu Met Ser Ser Leu His Leu Lys Arg Tyr Tyr Gly Arg Ile
            115                 120                 125

Leu His Tyr Leu Lys Ala Lys Glu Tyr Ser His Cys Ala Trp Thr Ile
        130                 135                 140

Val Arg Val Glu Ile Leu Arg Asn Phe Tyr Phe Ile Asn Arg Leu Thr
145                 150                 155                 160

Gly Tyr Leu Arg Asn
                165
```